United States Patent
Shepherd et al.

(10) Patent No.: US 10,400,219 B2
(45) Date of Patent: *Sep. 3, 2019

(54) ENGINEERED LIVER TISSUES, ARRAYS THEREOF, AND METHODS OF MAKING THE SAME

(71) Applicant: Organovo, Inc., San Diego, CA (US)

(72) Inventors: Benjamin R. Shepherd, San Diego, CA (US); Justin B. Robbins, San Diego, CA (US); Vivian A. Gorgen, San Diego, CA (US); Sharon C. Presnell, San Diego, CA (US)

(73) Assignee: Organovo, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/166,006

(22) Filed: May 26, 2016

(65) Prior Publication Data

US 2016/0272946 A1 Sep. 22, 2016

Related U.S. Application Data

(62) Division of application No. 13/841,430, filed on Mar. 15, 2013, now Pat. No. 9,442,105.

(51) Int. Cl.
| | |
|---|---|
| *C12N 5/071* | (2010.01) |
| *G01N 33/50* | (2006.01) |
| *C12N 5/077* | (2010.01) |

(52) U.S. Cl.
CPC ......... *C12N 5/0697* (2013.01); *C12N 5/0656* (2013.01); *C12N 5/0671* (2013.01); *G01N 33/5008* (2013.01); *G01N 33/5088* (2013.01); *C12N 2502/14* (2013.01); *C12N 2502/28* (2013.01); *C12N 2533/30* (2013.01); *C12N 2535/10* (2013.01)

(58) Field of Classification Search
CPC .. C12N 5/0697; C12N 5/0656; C12N 5/0671; C12N 2502/14; C12N 2502/28; C12N 2533/30; C12N 2535/10; G01N 33/5008; G01N 33/5088
See application file for complete search history.

(56) References Cited

U.S. PATENT DOCUMENTS

| | | |
|---|---|---|
| 4,759,764 A | 7/1988 | Fawcett et al. |
| 4,808,435 A | 2/1989 | Cropp et al. |
| 5,099,090 A | 3/1992 | Allan et al. |
| 6,315,469 B1 | 11/2001 | Alvarez et al. |
| 6,401,795 B1 | 6/2002 | Cesarano, III et al. |
| 6,454,972 B1 | 9/2002 | Morisette et al. |
| 6,520,997 B1 | 2/2003 | Pekkarinen |
| 6,537,567 B1 | 3/2003 | Niklason et al. |
| 6,561,607 B1 | 5/2003 | Lubinsky et al. |
| 6,642,243 B1 | 11/2003 | Imanzahrai |
| 6,713,772 B2 | 3/2004 | Goodman et al. |
| 6,939,489 B2 | 9/2005 | Moszner et al. |
| 6,942,830 B2 | 9/2005 | Mülhaupt et al. |
| 6,979,670 B1 | 12/2005 | Lyngstadaas et al. |
| 6,986,739 B2 | 1/2006 | Warren et al. |
| 7,051,654 B2 | 5/2006 | Boland et al. |
| 7,196,842 B2 | 3/2007 | Weigl et al. |
| 7,484,837 B2 | 2/2009 | Koga et al. |
| 7,625,198 B2 | 12/2009 | Lipson et al. |
| 7,651,665 B2 | 1/2010 | Gonzalez et al. |
| 7,680,555 B2 | 3/2010 | Dunn et al. |
| 7,767,446 B2 | 8/2010 | Robbins et al. |
| 8,143,055 B2 | 3/2012 | Forgacs et al. |
| 8,241,905 B2 | 8/2012 | Forgacs et al. |
| 8,343,740 B2 | 1/2013 | Gonda et al. |
| 8,580,546 B2 | 11/2013 | Gonda et al. |
| 8,728,807 B2 | 5/2014 | Forgacs et al. |
| 8,747,880 B2 | 6/2014 | Forgacs et al. |
| 8,852,932 B2 | 10/2014 | Forgacs et al. |
| 8,931,880 B2 | 1/2015 | Murphy et al. |
| 2001/0042942 A1 | 11/2001 | Hizumi et al. |
| 2002/0171178 A1 | 11/2002 | Dean et al. |
| 2002/0182633 A1 | 12/2002 | Chen et al. |
| 2002/0188349 A1 | 12/2002 | McAllister et al. |
| 2003/0049839 A1 | 3/2003 | Romero-Ortega et al. |
| 2003/0096411 A1 | 5/2003 | Michalopoulos et al. |
| 2003/0149505 A1 | 8/2003 | Mogensen |
| 2003/0153078 A1 | 8/2003 | Libera et al. |
| 2003/0175410 A1 | 9/2003 | Campbell et al. |

(Continued)

FOREIGN PATENT DOCUMENTS

| | | |
|---|---|---|
| CA | 2306346 | 1/1999 |
| EP | 2090584 | 8/2009 |

(Continued)

OTHER PUBLICATIONS

Chang, R., et al., "Biofrabrication of a three-dimensional liver micro-organ as in in vitro drug metabolism model," *Biofabrication* 2:1-11, 11 pages, IOP Publishing Ltd., United Kingdom (2010).

Guillotin, B. and Guillemot, F., "Cell patterning technologies for organtypic tissue fabrication," *Trends in Biotechnology* 29(4):183-190, Elsevier Science Publishers B.V., Netherlands (2011).

Murphy, S.V. and Atala, A., "3D bioprinting of tissues and organs," *Nature Biotechnology* 32(8):773-785, Nature America Publishing, United States (2014).

Ohashi, K., et al., "Engineering functional two- and three-dimensional liver systems in vivo using hepatic tissue sheets," *Nature Medicine* 13(7):880-885, Nature Publishing Group, England (2007).

(Continued)

*Primary Examiner* — Titilayo Moloye
(74) *Attorney, Agent, or Firm* — Sterne, Kessler, Goldstein & Fox P.L.L.C.

(57) ABSTRACT

Engineered, living, three-dimensional liver tissue constructs including: one or more layers, wherein each layer contains one or more liver cell types, the one or more layers cohered to form a living, three-dimensional liver tissue construct free of pre-formed scaffold. Also disclosed are arrays and methods of making the same.

20 Claims, 20 Drawing Sheets

(56) References Cited

U.S. PATENT DOCUMENTS

| | | |
|---|---|---|
| 2003/0236588 A1 | 12/2003 | Jang et al. |
| 2004/0006405 A1 | 1/2004 | Chen et al. |
| 2004/0132184 A1 | 7/2004 | Dennis et al. |
| 2004/0197367 A1 | 10/2004 | Rezania et al. |
| 2004/0219133 A1 | 11/2004 | Lyles |
| 2004/0237822 A1 | 12/2004 | Boland et al. |
| 2004/0253365 A1 | 12/2004 | Warren et al. |
| 2005/0009178 A1 | 1/2005 | Yost et al. |
| 2005/0169962 A1 | 8/2005 | Bhatia et al. |
| 2005/0226856 A1 | 10/2005 | Ahlfors |
| 2005/0276791 A1 | 12/2005 | Hansford et al. |
| 2006/0099287 A1 | 5/2006 | Kim et al. |
| 2006/0198918 A1 | 9/2006 | Koyagi et al. |
| 2006/0237880 A1 | 10/2006 | Wicher et al. |
| 2006/0270032 A1* | 11/2006 | Bhatia .................. C12N 5/0671 435/325 |
| 2007/0142916 A1 | 6/2007 | Olson, Jr. |
| 2007/0200276 A1 | 8/2007 | Mackey et al. |
| 2007/0231787 A1 | 10/2007 | Voelker |
| 2007/0299508 A1 | 12/2007 | Morrison et al. |
| 2008/0027114 A1 | 1/2008 | Funke et al. |
| 2008/0070304 A1 | 3/2008 | Forgacs et al. |
| 2008/0097575 A1 | 4/2008 | Cottone |
| 2008/0192074 A1 | 8/2008 | Dubois et al. |
| 2008/0193910 A1 | 8/2008 | Larkin et al. |
| 2009/0076531 A1 | 3/2009 | Richardson et al. |
| 2009/0117087 A1 | 5/2009 | Carroll et al. |
| 2009/0142307 A1 | 6/2009 | Athanasiou et al. |
| 2009/0206522 A1 | 8/2009 | Hein et al. |
| 2009/0208466 A1 | 8/2009 | Yoo |
| 2009/0208577 A1 | 8/2009 | Xu et al. |
| 2009/0239302 A1 | 9/2009 | Decher et al. |
| 2009/0248145 A1 | 10/2009 | Chan |
| 2009/0263849 A1 | 10/2009 | Sun et al. |
| 2009/0267269 A1 | 10/2009 | Lim et al. |
| 2010/0041134 A1 | 2/2010 | Forgacs et al. |
| 2010/0056390 A1 | 3/2010 | Fischbach |
| 2010/0160183 A1 | 6/2010 | Xu et al. |
| 2010/0190246 A1 | 7/2010 | Hase |
| 2010/0191360 A1 | 7/2010 | Napadensky et al. |
| 2010/0254900 A1 | 10/2010 | Campbell et al. |
| 2011/0064784 A1 | 3/2011 | Mullens et al. |
| 2011/0172611 A1 | 7/2011 | Yoo et al. |
| 2011/0180914 A1 | 7/2011 | Do et al. |
| 2011/0212501 A1 | 9/2011 | Yoo |
| 2011/0250688 A1 | 10/2011 | Hasan |
| 2012/0045770 A1 | 2/2012 | Pongracz et al. |
| 2012/0089238 A1 | 4/2012 | Kang et al. |
| 2012/0116568 A1* | 5/2012 | Murphy .................. B41J 3/407 700/118 |
| 2012/0196343 A1 | 8/2012 | Forgacs et al. |
| 2012/0288938 A1 | 11/2012 | Forgacs et al. |
| 2013/0108726 A1 | 5/2013 | Uckelmann et al. |
| 2013/0164339 A1 | 6/2013 | Murphy et al. |
| 2013/0190210 A1 | 7/2013 | Murphy et al. |
| 2013/0193619 A1 | 8/2013 | Church et al. |
| 2013/0236431 A1 | 9/2013 | Gourdie et al. |
| 2013/0236879 A1 | 9/2013 | Berry et al. |
| 2013/0345794 A1 | 12/2013 | Khatiwala et al. |
| 2014/0012225 A1 | 1/2014 | Yoo et al. |
| 2014/0012407 A1 | 1/2014 | Murphy et al. |
| 2014/0044822 A1 | 2/2014 | Mulliken |
| 2014/0093932 A1 | 4/2014 | Murphy et al. |
| 2014/0099709 A1 | 4/2014 | Presnell et al. |
| 2014/0131313 A1 | 5/2014 | Wakamatsu et al. |
| 2014/0220685 A1 | 8/2014 | Forgacs et al. |
| 2014/0265049 A1 | 9/2014 | Burris et al. |
| 2014/0287960 A1 | 9/2014 | Shepherd et al. |
| 2014/0358273 A1 | 12/2014 | LaBossiere et al. |
| 2015/0004273 A1 | 1/2015 | Forgacs et al. |
| 2015/0037445 A1 | 2/2015 | Murphy et al. |
| 2015/0057786 A1 | 2/2015 | Murphy et al. |

FOREIGN PATENT DOCUMENTS

| | | | |
|---|---|---|---|
| JP | 2001038981 | 2/2001 | |
| JP | 2005031144 | 2/2005 | |
| JP | 2006159117 | 6/2006 | |
| JP | 2010-057439 | 3/2010 | |
| KR | 20090087748 A | 8/2009 | |
| RU | 2330675 C2 | 8/2008 | |
| RU | 2371758 | 10/2009 | |
| WO | WO-1999-01538 | 1/1999 | |
| WO | WO-2001-68811 | 9/2001 | |
| WO | WO-2004-108418 | 12/2004 | |
| WO | WO-2005025493 A2 | 3/2005 | |
| WO | WO-2005-081970 | 9/2005 | |
| WO | WO-2007-076272 | 7/2007 | |
| WO | WO-2007-115336 A2 | 10/2007 | |
| WO | WO-2007-115337 A2 | 10/2007 | |
| WO | WO-2007-124023 | 11/2007 | |
| WO | WO-2007/125893 | 11/2007 | |
| WO | WO-2007126411 A2 | 11/2007 | |
| WO | WO-2007136936 A2 | 11/2007 | |
| WO | WO-2009-102484 A2 | 8/2009 | |
| WO | WO-2009-154466 | 12/2009 | |
| WO | WO-2010-008905 | 1/2010 | |
| WO | WO-2011-038373 | 3/2011 | |
| WO | WO-2011088213 | 7/2011 | |
| WO | WO-2011-097330 | 8/2011 | |
| WO | WO-2011-107599 | 9/2011 | |
| WO | WO-2011-119059 A1 | 9/2011 | |
| WO | WO-2012-54195 | 9/2011 | |
| WO | WO-2012-003465 | 1/2012 | |
| WO | WO-2012131000 A1 | 10/2012 | |
| WO | WO 2013/040078 A2 | 3/2013 | |
| WO | WO 2013/040078 A3 | 3/2013 | |
| WO | WO-2013130823 A1 * | 9/2013 | ........... C12N 5/0012 |
| WO | WO-2013192290 A1 | 12/2013 | |
| WO | WO 2015066705 A1 | 5/2015 | |

OTHER PUBLICATIONS

Organovo, Press Release, "Organovo Describes First Fully Cellular 3D Bioprinted Liver Tissue," Apr. 22, 2013, 2 pages.
Sakai, Y., "Toward engineering of vascularized three-dimensional liver tissue equivalents possessing a clinically significant mass," *Biochemical Engineering Journal* 48:348-361, Elsevier B.V., Netherlands (2009).
Tsuda, Y., "Preparation of temperature-reactivity patterned culture plate and construction of high-functional patterned co-cultivated cell sheets," *Journal of Life Support Engineering* 16(1):38-39, JStage, Japan (2004).
Office Action, dated Mar. 16, 2016 in Japanese Application No. Tokugan2016-502212, Japanese Patent Office, 9 pages.
English language translation of NPL7, Tsuda, Y., "Preparation of temperature-reactivity patterned culture plate and construction of high-functional patterned co-cultivated cell sheets," *Journal of Life Support Engineering* 16(1):38-39, JStage, Japan (2004).
Partial English language translation of Japanese Publication No. JP 2010-057439 (cited as document FP2 on accompanying IDS SB0SA form).
Kano, K., et al., "Long-term maintenance of function of liver cells laminated on vascular endothelial cell sheet using cell sheet engineering," *Regenerative Therapy* 5:209, abstract No. P-114, The Japanese Society for Regenerative Medicine, Japan (Supplement 2006).
English language translation of document NPL11, Kano, K., et al., "Long-term maintenance of function of liver cells laminated on vascular endothelial cell sheet using cell sheet engineering," *Regenerative Therapy* 5:209, abstract No. P-114, The Japanese Society for Regenerative Medicicine, Japan (Supplement 2006).
Co-pending U.S. Appl. No. 14/933,822, filed Nov. 5, 2015.
Co-pending U.S. Appl. No. 14/936,580, filed Nov. 9, 2015.
Co-pending U.S. Appl. No. 14/950,567, filed Nov. 24, 2015.
Cui et al. Direct Human Cartilage Repair Using Three-Dimensional Bioprinting Technology. Tissue Engineering Part A 18(11-12):1304-1312 (2012).

(56) References Cited

OTHER PUBLICATIONS

Fujita et al. Fabrication of scaffold-free contractile skeletal muscle tissue using magnetite-incorporated myogenic C2C12 cells. J Tissue Eng Regen Med. 4(6):437-443 (2010).
Hierlihy et al. The post-natal heart contains a myocardial stem cell population. FEBS Letters 530:239-243 (2002).
Liu et al. Design and Development of Three-Dimensional Scaffolds For Tissue Engineering. Chemical Engineering Researh and Design 85(7):1051-1064 (2007).
Pearson Education. Human Heart Illustration (2004).
Tanaka et al. A Valved Hepatic Portoduodenal Intestinal Conduit for Biliary Atresia. Ann. Surg. 213(3):230-235 (1991).
Tsang et al. Fabrication of 3D hepatic tissues by additive photopatterning of cellular hydrogels. The FASEB Journal 21(3):790-801 (2007).
U.S. Appl. No. 13/612,778 Office Action dated Nov. 17, 2015.
U.S. Appl. No. 14/244,679 Office Action dated Oct. 23, 2015.
ATCC Product Catalog MCF7 (ATCC® HTB-22TM) https://www.atcc.org/products/all/HTB-22.aspx?slp=1#generalinformation, retrieved Sep. 18, 2015.
ATCC Product catalog Primary Subcutaneous Pre-adipocytes; Normal, Human (ATCC® PCS-210-01OTM) https://www.atcc.org/Products/All/PCS-210-010.aspx?slp=1, retrieved Sep. 18, 2015.
Co-pending U.S. Appl. No. 14/827,152, filed Sep. 14, 2015.
Co-pending U.S. Appl. No. 14/876,659, filed Oct. 6, 2015.
Dirat et al. Cancer-associated adipocytes exhibit an activated phenotype and contribute to breast cancer invasion. Cancer Res. 71(7):2455-2465 (2011).
Egebald et al. Tumors as organs: complex tissues that interface with the entire organism, Dev Cell. 18(6):884-901 (2010).
Grange et al. Isolation and characterization of human breast tumor-derived endothelial cells. Oncol Rep. 15(2):381-386 (2006).
PCT/US2014/026679 International Preliminary Report on Patentability dated Sep. 24, 2015.
U.S. Appl. No. 13/634,863 Office Action dated Sep. 8, 2015.
U.S. Appl. No. 13/794,368 Office Action dated Sep. 23, 2015.
U.S. Appl. No. 14/295,226 Office Action dated Sep. 9, 2015.
U.S. Appl. No. 14/678,392 Office Action dated Oct. 8, 2015.
U.S. Appl. No. 14/678,392 Office Action dated Sep. 24, 2015.
U.S. Appl. No. 14/796,910 Office Action dated Sep. 25, 2015.
Zhang et al. Characterization of printable cellular micro-fluidic channels for tissue engineering. Biofabrication 5:025004 (2013).
Bunnel et al. Adipose-derived Stem Cells: Isolation, Expansion and Differentiation. Methods 45(2):115-120 (2008).
Constans, Body by Science, The Scientist 17(19):34-37 http://www.the-scientist.com/article/display/141541 (2003).
Co-pending U.S. Appl. NO. 14/678,392, filed Apr. 3, 2015.
Co-pending U.S. Appl. No. 14/796,910, filed Jul. 10, 2015.
Forgacs et al. Biological Relevance of Tissue Liquidity and Viscoelasticity Eds. A. Deutsch, M. Falcke, J. Howard and W. Zimmermann. Birkhauser, pp. 269-277 (2004).
Izaguirre et al. CompuCell, a multi-model framework for simulation of morphogenesis. Bioinformatics 20(7):1129-1137 (2004).
Jakab et al. Organ printing: fiction or science. Biorheology 43(3-4):371-375 (2004).
Jakab et al. Three-dimensional tissue constructs built by bioprinting. Biorheology 43(3-4):509-513 (2006).
Khatiwala et al. 3D Cell Bioprinting for Regenerative Medicine Research and Therapies. Gene Therapy and Regulation 7(1):1-19 (2012).
King et al. Development of 3D bioprinted human breast cancer for in vitro screening of therapeutics targeted against cancer progression. IEEE The American Society for Cell biology. 2013 ascb annual meeting, New Orleans: IEEE Dec. 14-18, 2013.
Mironov et al. Organ printing: self-assembling cell aggregates as a "bioink". Science and Medicine 9:69-71 (2003).
Neagu et al. Role of physical mechanisms in biological self-organization. Phys RevLett 95(17):178104 (2005).
Newman et al. Before programs: the physical origination of multicellular forms. Int J Dev Biol. 50(2-3):289-299 (2006).

PCT/US2014/041419 International Search Report and Written Opinion dated Jan. 2, 2015.
Riken, Self-healing hydrogeis ease into production, Research Highlights: Materials, Downloaded from the Riken website: <http://www.riken.jp/en/research/rikenresearch/highlights/7543/> (Nov. 1, 2013) [accessed Apr. 27, 2015].
Shafrir et al. Mechanotransduction through the cytoskeleton. American Journal of Physiology 282:479-486 (2002).
Sheehan et al. Recent Patents and Trends in Bioprinting. Recent Patents on Biomedical Engineering 4:26-32 (2011).
U.S. Appl. No. 13/612,768 Office Action dated Jul. 30, 2015.
U.S. Appl. No. 13/794,368 Office Action dated May 8, 2015.
U.S. Appl. No. 13/801,780 Office Action dated Jun. 5, 2015.
U.S. Appl. No. 14/295,226 Office Action dated May 7, 2015.
U.S. Appl. No. 14/447,412 Office Action dated Jul. 15, 2015.
U.S. Appl. No. 14/530,499 Office Action dated May 14, 2015.
Xu et al. A three-dimensional in vitro ovarian cancer coculture model using a high-throughput cell patterning platform. Biotechnology Journal 6(2):204-212 (2011).
Tao et al. Bio-printing of living organized tissues using an inkjet technology. Database Accession No. PREV200700335042; FASEB Journal 23(5):A636 (2007).
Xu et al. In vivo generation of functional tissues using the inkjet printing technology, Tissue Engineering 13(7):1713-1714 (2007).
Moon et al. Layer by Layer Three-dimensional Tissue Epitaxy by Cell-Laden Hydrogel Droplets. Tissue Engineering Part C: Methods 16(1): 157-166 (2010).
Fuellhase et al. 264 Generation Of Organized Bladder Tissue Constructs Using A Novel Hybrid Printing System. European Urology Supplements 8(4):186 (2009).
Kasko. Degradable Poly(ethylene glycol) Hydrogels for 2D and 3D Cell Culture. Aldrich Materials Science, pp. 67-75 (no date available).
PCT/US2013/046519 International Preliminary Report on Patentability dated Dec. 23, 2014.
Smith. A direct-write three-dimensional Bioassembly tool for regenerative medicine. The University of Arizona, Nov. 1, 2005, pp. 1-291.
U.S. Appl. No. 13/246,428 Office Action dated Jan. 14, 2015.
U.S. Appl. No. 13/794,368 Office Action dated Nov. 26, 2014.
U.S. Appl. No. 13/634,863 Office Action dated Jan. 28, 2015.
U.S. Appl. No. 14/447,412 Office Action dated Mar. 3, 2015.
PCT/US2014/048962 International Search Report and Written Opinion dated Nov. 10, 2014.
U.S. Appl. No. 13/612,768 Office Action dated Nov. 17, 2014.
U.S. Appl. No. 13/801,780 Office Action dated Nov. 14, 2014.
Halley et al. Growing Organs In the Lab, Longevity, 1-7, Jun. 2009.
PCT/US2005/05735 International Preliminary Report on Patentability dated Mar. 3, 2009.
PCT/US2009/48530 International Preliminary Report on Patentability dated Jan. 13, 2011.
PCT/US2012/054923 International Preliminary Report on Patentability dated Mar. 20, 2014.
PCT/US2013/036479 International Preliminary Report on Patentability dated Oct. 21, 2014.
PCT/US2014/026679 International Search Report and Written Opinion dated Jul. 22, 2014.
Shim et al. Bioprinting of a mechanically enhanced three-dimensional dual cell-laden construct for osteochondral tissue engineering using a multi-head tissue/organ building system. J of Micromechanics and Microengineering. 22(Article No. 085014):1-11, 2012.
U.S. Appl. No. 13/612,778 Office Action dated Nov. 7, 2014.
U.S. Appl. No. 13/246,428 Office Action dated Aug. 26, 2014.
U.S. Appl. No. 14/295,226 Office Action dated Oct. 8, 2014.
CN201180020669.1 Office Action dated Jun. 4, 2014.
U.S. Appl. No. 13/968,313 Office Action dated Jun. 26, 2014.
Bioscaffolder 2008, www.syseng.de, SYSENG Dipl.-Ing. Hendrik John.
Boland et al, Application of inkjet printing to tissue engineering, Biotech J. 1:910-917 (2006).

(56) References Cited

OTHER PUBLICATIONS

Federovich et al, Distinct Tissue Formation by Heterogeneous Printing of Osteo- and Endothelial Progenitor Cells, Tissue Engineering: Part A, 17(15-16):2113-2123 2011.
Federovich et al, Three-Dimensional Fiber Deposition of Cell-Laden, Viable Patterned Constructs for Bone Tissue Printing, Tissue Engineering: Part A, 14(1):127-135 (2008).
Ghorbanian et al., Microfluidic direct writer with integrated declogging mechanism for fabricating cell-laden hydrogel constructs, Biomed Microdevices, Mar. 4, 2014, 9 pgs.
Gruene et al, Laser Printing of Stem Cells for Biofabrication of Scaffold-Free Autologous Grafts, Tissue Engineering: Part C, 17(1):79-89 (2011).
Guillemot et al, High-throughput laser printing of cells and biomaterials for tissue engineering, Acta biomaterialia, 6:2494-2500 (2010).
KR 10-2012-7026891 Office Action Feb. 18, 2014.
Larkin et al, Structure and Functional Evaluation of Tendon-Skeletal Muscle Constructs Engineered in Vitro, Tissue Eng. 12(11):3149-3158 Nov. 2006.
McGuigan et al, Vascularized organoid engineered by modular assembly enables blood perfusion, PNAS, 103(31):11461-11466 (2006).
Mehesz et al, Scalable robotic biofabrication of tissue spheroids, Biofabrication, 3:1-8 2011.
Pathology Outlines: Bladder, Normal Histology. 2011 pp. 1-4.
PCT/US2011/023520 IPRP and Written Opinion dated Aug. 16, 2013.
PCT/US2012/054935 IPRP and Written Opinion dated Mar. 20, 2014.
Skardal et al, Bioprinting vessel-like constructs using hyaluronan hydrogels crosslinked with tetrahedral polyethylene glycol tetracrylates, Biomaterials. 31:6173-6181 (2010).
Smith et al, Characterizing Environment Factors that Impact the Viability of Tissue-Engineered Constructs Fabricated by a Direct-Write Bioassembly Tool, Tissue Engineering, 13(2): 373-385 (2007).
U.S. Appl. No. 13/612,768 Office Action dated May 30, 2014.
U.S. Appl. No. 13/612,778 Office Action dated Apr. 28, 2014.
Wake Forest Baptist Medical Center (Wake Forest Physician Reports First Human Recipients of Laboratory-Grown Organs. 2006 pp. 1-2).
AU2011212998 Examination Report dated Jul. 26, 2013.
AU2011227282 First Examination Report dated Jan. 9, 2013.
AU2009271223 Examination Report dated Sep. 5, 2013.
AU2011318437 Examination Report dated Dec. 10, 2013.
Baltich, J., et al., "Development of a scaffoldless Three-dimensional Engineered Nerve Using a Nerve-Fibroblast Co-Culture," In Vitro Cell. Dev. Biol.—Animal, 2010, pp. 438-444, vol. 46.
Boland et al., "Cell and Organ Printing 2: Fusion of Cell Aggregates in Three-Dimensional Gels," The Anatomical Record, Part A, 2003, vol. 272A, pp. 497-502.
CA2729559 Office Action dated Dec. 10, 2013.
CA2793205 Office Action dated Nov. 7, 2013.
Chaterji, Somali et al. "Scaffold-Free In Vitro Arterial Mimetics: The Importance of Smooth Muscle-Endothelium Contact", Tissue Engineering Part A, Mar. 8, 2010 (Mar. 8, 2010), pp. 1901-1912.
CN200980131924 Office action dated Jan. 14, 2013.
CN201180017227.1 Office Action dated Nov. 15, 2013.
Constans, A., "*Body by Science,*" The Scientist, Oct. 6, 2003, vol. 17, No. 19, http://www.the-scientist._com/article/display/141541, 7 pages.
Dai, W., et al., "Fibroblast Aggregation by suspension with Conjugates of Poly(ethylene glycol) and RGD," Biotechnology and Bioengineering, May 20, 1996, pp. 349-356, vol. 50, No. 4.
Dominici, M., et al., "Minimal criteria for defining multipotent mesenchymal stromal cells," International Society for Cellular Therapy position statement, Cytotherapy (2006), vol. 8, No. 4, 315-317.
Edelman, E.R. "Vascular Tissue Engineering: Designer Arteries." Circ Res, 1999, 85(12):1115-1117.

Eisenberg, C. A., et al., "Bone Marrow Cells Transdifferentiate to Cardiomyocytes When Introduced into the Embryonic Heart," Stem Cells, 2006, pp. 1236-1245, vol. 24.
EP09798534.5 Extended European Search Report dated Jan. 10, 2013.
EP11740319.6 European Search Report dated Jul. 16, 2013.
EP117566951.7 Extended European Search Report Jan. 20, 2014.
Forgacs, G., et al., "Viscoelastic Properties of Living Embryonic Tissues: A Quantitative Study," Biophysical Journal, May 1998, pp. 2227-2234, vol. 74, No. 5.
Foty, R. A., et al., "Surface Tensions of Embryonic Tissues Predict Their Mutual Envelopment Behavior," Development, 1996, pp. 1611-1620, vol. 122, No. 5.
Foty, R. A., et al., "The Differential Adhesion Hypothesis: A Direct Evaluation," Developmental Biology, 2005, pp. 255-263, vol. 278, vol. 1.
Frisman, I., et al, "Nanostructuring of PEG-fibrinogen polymeric scaffolds," Acta Biomaterialia, 2009, pp. 2518-2524, vol. 6(7).
Furukawa, et al. "Scaffold-free cartilage tissue by mechanical stress loading for tissue engineering." In Tissue Engineering, ed by Daniel Eberli. InTech 2010, P. 409-428.
Furukawa, K. S., et al., "Formation of Human Fibroblast Aggregates (Spheroids) by Rotational Culture," Cell Transplantation, 2001, pp. 441-445, vol. 10, No. 4-5.
Furukawa K. S., et al., "Tissue-engineered Skin Using Aggregates of Normal Human Skin Fibroblasts and Biodegradable Material," J. MK Organs, 2001, pp. 353-356, vol. 4.
GB 1008781.5 Examination Report dated Sep. 22, 2010.
GB 1203622.4 Examination Report dated Jul. 16, 2012.
Glazier, J. A., et al., "Simulation of the Differential Adhesion Driven Rearrangement of Biological Cells," Physical Review E, Mar. 1993, pp. 2128-2154, vol. 47, No. 3.
Glicklis, R., et al., "Modeling Mass Transfer in Hepatocyte Spheroids Via Cell Viability, Spheroid Size, and Hepatocellular Functions," Biotechnology and Bioengineering, Jun. 20, 2004, pp. 672-680, vol. 86, No. 6.
Graner, F., et al., "Simulation of Biological Cell Sorting Using a Two-Dimensional Extended Potts Model," Physical Review Letters, Sep. 28, 1992, pp. 2013-2016, vol. 69, No. 13.
Gruene, et al. "Laser printing of three-dimensional multicellular arrays for studies of cell-cell and cell-environment interactions," Tissue Eng Part C Methods, Oct. 2011;17(10):973-82.
Guenard, V., et al., "Syngeneic Schwann Cells Derived from Adult Nerves Seeded in Semipermeable Guidance Channels Enhance Peripheral Nerve Regeneration," The Journal of Neuroscience, Sep. 1992, pp. 3310-3320, vol. 12, No. 9.
Hadlock, T., et al., "A Polymer Foam Conduit Seeded with Schwann Cells Promotes Guided Peripheral Nerve Regeneration," Tissue Engineering, 2000, pp. 119-127, vol. 6, No. 2.
Harvey et al., Schwann cells and fetal tectal tissue cografted to the midbrain of newborn rats: fate of Schwann cells and their influence on host retinal innervation of grafts, Exp Neurol. Aug. 1995;134(2):179-91.
Hockaday, I., et al. "Rapid 3D printing of anatomically accurate and mechanically heterogeneous aortic valve hydrogel scaffolds," Biofabrication, 2012 pp. 1-12, vol. 4(3).
Hubbard, B. A., et al., "Bioengineered, Autologous, Scaffold-free Nerve Conduit for Peripheral Nerve Repair," Abstract, AAHS/ASPN/ASRM 2011, Annual Scientific Meetings Program Book, Jan. 12-18, 2011, pp. 140 and 159.
Ito, Akira et al. "Novel Methodology for Fabrication of Tissue-Engineered Tubular Constructs Using Magnetite Nanoparticles and Magnetic Force", Tissue Engineering, Larchmont, NY, US, vol. 11, No. 9-10, Sep. 2005 (2005-09), pp. 1553-1561.
Iwasaki et al. "Bioengineered Three-layered Robust and Elastic Artery Using Hemodynamically-Equivalent Pulsatile Bioreactor," Circulation, 18 (14) Suppl, 2008, S53-S57.
Jakab et al. "Engineering Biological Structures of Prescribed Shape Using Self-assembling Multicellular Systems." *Proc. Natl. Acad. Sci.* USA, 2004, 101:2864-2869.
Jakab, et al. "Tissue Engineering by Self-Assembly and Bio-printing of living cells." Biofabrication, Jun. 2, 2010, vol. 2, No. 2, p. 022001 (pp. 1-14).

(56) References Cited

OTHER PUBLICATIONS

Jakab, K., et al., "Relating Cell and Tissue Mechanics: Implications and Applications," Developmental Dynamics, 2008, pp. 2438-2449, vol. 237.
Jakab, K., et al., "Tissue Engineering by Self-Assembly of Cells Printed into Topologically Defined Structures," Tissue Engineering: Part A, Nov. 3, 2008, pp. 413-421, vol. 14.
JP2011-516626 Office Action dated Feb. 4, 2014.
Kelm, J. M., et al., "Design of Custom-Shaped Vascularized Tissues Using Microtissue Spheriods as Minimal Building Units," Tissue Engineering, 2006, pp. 2151-2160, vol. 12, No. 8.
Kelm, J. M., et al., "Microscale Tissue Engineering Using Gravity-Enforced Cell Assembly," Trends in Biotechnology, Apr. 2004, pp. 195-202, vol. 22, No. 4.
Koibuchi, N., et al., "Behavior of Cells in Artificially Made Cell Aggregates and Tissue Fragments after Grafting to Developing Hind Limb Buds in Xenopus laevis," The International Journal of Developmental Biology, 1999, pp. 141-148, vol. 43, No. 2.
Korff, T., et al., "Blood Vessel Maturation in a 3-Dimensional Spheroidal Coculture Model: Direct Contact with Smooth Muscle Cells Regulates Endothelial Cell Quiescence and Abrogates VEGF Responsiveness," The FASEB Journal, Feb. 2001, pp. 447-457, vol. 15.
KR 10-2012-7026891 Office Action Jan. 18, 2014.
L'Heureux et al. "A completely biological tissue-engineered human blood vessel," The FASEB Journal, 12 (1), 1998, 47-56.
L'Heureux et al. "Human tissue-engineered blood vessels for adult arterial revascularization," Nature Medicine, 12 (3), 2006, 361-365.
L'Heureux et al. "Sheet-Based Tissue Engineering From Bench Top to the First Clinical Use of a Completely Biological Tissue Engineered Vessel," The FASEB Journal, 12 (1), 2006, 47-56 (Abstract).
Lee et al. "Multi-layered Culture of Human Skin Fibroblasts and Keratinocytes Through Three-dimensional Freeform Fabrication." *Biomaterials*.2009, 30:1587-1595.
Luo et al. "Three-dimensional microtissue assay for high-throughput cytotoxicity of nanoparticles." Anal Chem. Aug. 7, 2012;84(15):6731-8.
Marga et al. "Toward Engineering Functional Organ Modules by Additive Manufacturing." *Biofabrication*, 2012, 4:022001, 12 pages.
Marga, F. S. et al., "Construction of a Bioprinted Fully Biological Nerve Graft," Abstract, Biophysical Journal, Feb. 2009, p. 643a, Vol. 96, No. 3, Supplement 1.
Marga, F., et al., "Bioprint Engineered Fully Biological Nerve Graft," Poster Presentation, TERMIS, Dec. 5-8, 2010, Orlando, Florida, 1 page.
Marga, F., et al., "Developmental Biology and Tissue Engineering," Birth Defects Research (Part C), 2007, pp. 320-328, vol. 81.
Marga, F., et al., "Engineered Fully Biological Nerve Graft," Poster Presentation, Biophysical Society Meeting, Mar. 4, 2009, 1 page.
Martin, I., et al., "Computer-Based Technique for Cell Aggregation Analysis and Cell Aggregation in In Vitro Chondrogenesis," Cytometry, 1997, pp. 141-146, vol. 28, No. 2.
Mironov et al. "Bioprinting Living Structures." *J. Mat. Chem.*, 2007, 17:2054-2060.
Mironov, V., et al., "Organ Printing: Computer-Aided Jet-Based 3D Tissue Engineering," Trends in Biotechnology, Apr. 2003, pp. 157-161, vol. 21, No. 4.
Mironov, V., et al., "Organ Printing: Self-Assembling Cell Aggregates as 'Bioink'," Science & Medicine, Apr. 2003, pp. 69-71, vol. 9, No. 2.
Mironov, V., et al., "Organ Printing: Tissue Spheroids as Building Blocks," Biomaterials, 2009, pp. 2164-2174, vol. 30.
Mizumoto, H., et al., "Formation of Cylindrical Multicellular Aggregate (Cylindroid) and Express of Liver Specific Functions of Primary Rat Hepatocytes," Cytotechnology, 1999, pp. 69-75, vol. 31.
Mombach, J. C. M., et al., "Quantitative Comparison Between Differential Adhesion Models and Cell Sorting in the Presence and Absence of Fluctuations," Physical Review Letters, Sep. 11, 1995, pp. 2244-2247, vol. 75, No. 11.

Mroue et al. "Three-dimensional cultures of mouse mammary epithelial cells." Methods Mol Biol. 2013;945:221-50.
Panagiotis, et al. 2001. "A unique aged human retinal pigmental epithelial cell line useful for studying lens differentiation in vitro," International Journal of Developmental Biology, vol. 45, pp. 753-758.
Paul et al., "How to improe R&D productivity: the pharmaceutical industry's grand challenge", Nature Reviews Drug Discovery 9(3):203-214 (2010).
Nickerson, C. A., et al., "Three-Dimensional Tissue Assemblies: Novel Models for the Study of *Salmonella enterica* Serovar Typhimurium Pathogenesis," Infection and Immunity, Nov. 2001, pp. 7106-7120, vol. 69, No. 11.
Niklason and Langer, "Advances in Tissue Engineering of Blood Vessels and Other Tissues." *Transpl. Immunol.*, 1997, 5(4):303-306.
Norottec et al. "Scaffold-free vascular tissue engineering using bioprinting," Biomaterials, 30, 2009, 5910-5917.
PCT/US2011/023520 International Search dated Oct. 31, 2011.
PCT/US2011/028713 International Search Report dated Nov. 30, 2011.
PCT/US2011/028713 IPRP and Written Opinion dated Sep. 18, 2012.
PCT/US2011/053515 International Search Report and Written Opinion dated May 1, 2012.
PCT/US2011/053515 IPRP and Written Opinion dated May 3, 2013.
PCT/US2013/036479 International search report dated Jul. 25, 2013.
PCT/US05/05735 International Search Report dated Dec. 7, 2007.
PCT/US09/48530 International Search Report dated Mar. 15, 2010.
PCT/US2012/054923 International Search Report dated Feb. 26, 2013.
PCT/US2012/054935 International Search Report dated Feb. 28, 2013.
PCT/US2013/046519 International Search Report dated Sep. 5, 2013.
Perez-Pomares and Foty. "Tissue Fusion and Cell Sorting in Embryonic Development and Disease: Biomedical Implications." *Bioessays*, 2006, 28:809-821.
Remuzzi, A., et al., "Vascular Smooth Muscle Cells on Hyaluronic Acid: Culture and Mechanical Characterization of an Engineered Vascular Construct," Tissue Engineering, 2004, pp. 699-710, vol. 10, No. 516.
RU 2012142992 Office Action dated Aug. 1, 2013.
Ryan, P. L., et al., "Tissue Spreading on Implantable Substrates is a Competitive Outcome of Cell-Cell vs. Cell-Substranum Adhesivity," Proceedings of the National Academy of Sciences, Apr. 10, 2001, pp. 4323-4327, vol. 98, No. 8.
Schuster et al., "Why Drugs Fail—A Study on Side Effects in New Chemical Entities," Curr. Pharm. Des. 2005, 11:3545.
"*Sciperio, Inc. 2003 R&D 100 Award Winner ,*" Sciperio, http://www.sciperio.com/news/20031016.asp, accessed on Feb. 1, 2005, 2 pages.
Siemionow, M., et al., "Current Techniques and Concepts in Peripheral Nerve Repair," Chapter 8, International Review of Neurobiology, 2009, pp. 141-172, Vol. 87.
Smith et al., "Three-Dimensional BioAssembly Tool for Generating Viable Tissue-Engineered Constructs," Tissue Engineering, vol. 10, No. 9/10, pp. 1566-1576 (2004).
Steinberg, M. S., "Does Differential Adhesion Govern Self-Assembly Processes in Histogenesis? Equilibrium Configurations and the Emergence of a Hierarchy Among Populations of Embryonic Cells," The Journal of Experimental Zoology, Apr. 1970, pp. 395-433, vol. 173, No. 4.
Steinberg, M. S., et al., "Liquid Behavior of Embryonic Tissues," Cell Behaviour, 1982, pp. 583-697.
Stiles, E., "*UA Wins R & D 100 Award for Machine that Prints Tissue Cell-by-Cell ,*" UANews, Dec. 2, 2003, http://uanews.org/cgi-binfflebObjects/UANews.woa/wa/goPrint?ArticleID)=8305, accessed on Feb. 1, 2005, 2 pages.
Tang, M. D., et al., "Molding of Three-Dimensional Microstructures of Gels,"Journal of the American Chemical Society, Oct. 29, 2003, pp. 12988-12989, vol. 125, No. 43.

(56) References Cited

OTHER PUBLICATIONS

Timmins, N. E., et al., "hanging-Drop Multicellular Spheriods as a Model of Tumour Angiogenesis,"Angiogenesis, 2004, pp. 97-103, vol. 7, No. 2.
Tsang, Advanced drug delivery reviews 2004, vol. 56 (11), pp. 1635-1647.
U.S. Appl. No. 10/590,446 Office action dated Jan. 6, 2011.
U.S. Appl. No. 10/590,446 Office action dated Sep. 1, 2011.
U.S. Appl. No. 13/529,172 Office action dated Sep. 24, 2013.
U.S. Appl. No. 10/666,836 Office action dated Oct. 28, 2004.
U.S. Appl. No. 11/227,489 Office action dated Dec. 10, 2008.
U.S. Appl. No. 11/227,489 Office action dated Jul. 8, 2009.
U.S. Appl. No. 13/020,000 Office action dated Dec. 31, 2012.
U.S. Appl. No. 13/020,000 Office action dated Jul. 3, 2013.
U.S. Appl. No. 13/402,215 Office Action dated Mar. 19, 2013.
U.S. Appl. No. 13/612,768 Office Action dated Oct. 1, 2013.
Wang, et al, "Bone marrow mesenchymal stem cells promote cell proliferation and neurotrophic function of Schwann cells in vitro and in vivo, " Brain Research, 2009, pp. 7-15, vol. 1262.
Yamauchi, N., et al., "A Three-Dimensional Cell Culture Model for Bovine endometrium: Regeneration of a Multicellular Spheroid Using Ascorbate," Placenta, 2003, pp. 258-269, Volume 24.
Office Action dated May 9, 2017, in U.S. Appl. No. 13/612,768, Murphy, K. et al., filed Sep. 12, 2012, 15 pages.
Office Action dated Jul. 24, 2017, in U.S. Appl. No. 13/612,768, Murphy, K. et al., filed Sep. 12, 2012, 25 pages.
Office Action dated Feb. 2, 2016, in U.S. Appl. No. 13/801,780, Presnell, S.C. et al., filed Mar. 13, 2013, 15 pages.
Office Action dated Sep. 7, 2016, in U.S. Appl. No. 13/801,780, Presnell, S.C. et al., filed Mar. 13, 2013, 12 pages.
Amendment and Reply Under 37 C.F.R. § 1.114 with Declaration Under 37 C.F.R. § 1.132 and Exhibit A filed Dec. 7, 2016, in U.S. Appl. No. 13/801,780, Presnell, S.C. et al., filed Mar. 13, 2013, 21 pages.
Office Action dated Aug. 14, 2017, in U.S. Appl. No. 13/801,780, Presnell, S.C. et al., filed Mar. 13, 2013, 12 pages.
Pampaloni, F. And Stelzer, E.H.K., "Three-Dimensional Cell Cultures in Toxicology," *Biotechnology and Genetic Engineering Reviews* 26:117-138, Taylor & Francis, England (2009).

* cited by examiner

ENGINEERED LIVER TISSUES, ARRAYS THEREOF, AND METHODS OF MAKING THE SAME

CROSS-REFERENCE TO RELATED APPLICATIONS AND INCORPORATION BY REFERENCE

This application is a divisional of U.S. application Ser. No. 13/841,430, filed Mar. 15, 2013, now U.S. Pat. No. 9,442,105, issued Sep. 13, 2016, which is incorporated by reference herein in its entirety.

BACKGROUND OF THE INVENTION

A number of pressing problems confront the healthcare industry. As of June 2012 there were 114,636 patients registered by United Network for Organ Sharing (UNOS) as needing an organ transplant. According to UNOS, between January and March 2012 only 6,838 transplants were performed. Each year more patients are added to the UNOS list than transplants are performed, resulting in a net increase in the number of patients waiting for a transplant.

Additionally, the research and development cost of a new pharmaceutical compound is approximately $1.8 billion. See Paul, et al. (2010). How to improve R&D productivity: the pharmaceutical industry's grand challenge. *Nature Reviews Drug Discovery* 9(3):203-214. Drug discovery is the process by which drugs are discovered and/or designed. The process of drug discovery generally involves at least the steps of: identification of candidates, synthesis, characterization, screening, and assays for therapeutic efficacy. Despite advances in technology and understanding of biological systems, drug discovery is still a lengthy, expensive, and inefficient process with low rate of new therapeutic discovery.

SUMMARY OF THE INVENTION

The invention relates to the field of regenerative medicine and tissue and/or organ engineering. More particularly, the invention relates to engineered liver tissue constructs, arrays thereof, and methods of fabrication.

In one aspect, disclosed herein are engineered, living, three-dimensional liver tissue constructs, the construct comprising at least one compartment defining a planar geometry, the compartment comprising an interior defined by a border, the interior comprising parenchymal cells, the border comprising non-parenchymal cells; the cells cohered to form a living, three-dimensional liver tissue construct; provided that at least one component of the construct was bioprinted and the construct is substantially free of pre-formed scaffold at the time of use. In some embodiments, the construct further comprises an extrusion compound, the extrusion compound improving the suitability of the cells for bioprinting. In some embodiments, the parenchymal cells are derived from one or more of the following sources: adult mammalian liver tissue; fetal mammalian liver tissue; established liver-derived cell lines or strains, embryonic stem cells (ESC); ESC-derived hepatocyte-like cells, induced pluripotent stem cells (IPSC); IPSC-derived hepatocyte-like cells; adult stem/progenitor cells derived from the liver; and adult stem/progenitor cells derived from a tissue other than liver. In some embodiments, the non-parenchymal cells comprise one or more of: vascular cells, endothelial cells, fibroblasts, mesenchymal cells, immune cells, Kupffer cells, stellate cells, biliary epithelial cells, biliary epithelial-like cells, sinusoidal endothelial cells, liver-derived stem/progenitor cells, and non-liver-derived stem/progenitor cells. In some embodiments, the construct comprises stem/progenitor cells that were exposed to one or more differentiation signals. In further embodiments, the differentiation signal comprises one or more of: biomechanical signals, soluble signals, and physical signals. In further embodiments, the stem/progenitor cells were exposed to one or more differentiation signals before fabrication of the construct. In further embodiments, the stem/progenitor cells were exposed to one or more differentiation signals during fabrication of the construct. In further embodiments, the stem/progenitor cells were exposed to one or more differentiation signals after fabrication of the construct. In some embodiments, the construct comprises one or more layers. In further embodiments, the construct comprises a plurality of layers, at least one layer compositionally or architecturally distinct from at least one other layer to create a laminar geometry. In some embodiments, the construct is for use in in vitro assays. In some embodiments, the construct is for use in one or more of: drug discovery; drug testing; preclinical research; toxicity testing; absorption, distribution, metabolism, and excretion testing (ADME); drug metabolism and pharmacokinetics testing (DMPK); disease modeling; infectious disease modeling; host disease modeling; three-dimensional biology studies; and cell-based screening. In some embodiments, the construct is for use in cell-based screening, wherein the screening is for one or more infectious diseases, liver fibrosis (e.g., cirrhosis), liver cancer, liver steatosis (e.g., fatty liver), one or more metabolic deficiencies, or one or more protein deficiencies. In further embodiments, the infectious diseases include viral infection or parasitic infection (e.g., *plasmodium* infection, etc.). In some embodiments, the construct is for use in long-term tissue toxicity studies, wherein analyses are conducted for periods >3 days and up to 6 months. In some embodiments, the construct is for use in the augmentation of one or more liver functions in humans. In further embodiments, the construct is for implantation in a subject at a site of injury, disease, or degeneration. In further embodiments, the construct is for clinical use in extracorporeal devices designed to augment or restore one or more liver functions. In some embodiments, the construct is non-innervated.

In another aspect, disclosed herein are engineered, living, three-dimensional liver tissue constructs comprising: one or more layers, each layer comprising one or more liver cell types, the one or more layers cohered to form a living, three-dimensional liver tissue construct, the construct characterized by having at least one of: at least one layer comprising a plurality of cell types, the cell types spatially arranged relative to each other to create a planar geometry; and a plurality of layers, at least one layer compositionally or architecturally distinct from at least one other layer to create a laminar geometry. In some embodiments, at least one component of the construct was bioprinted. In some embodiments, each layer of the engineered liver tissue comprises multiple cells in the X, Y, and Z axes. In further embodiments, each layer of the engineered liver tissue is at least about 50 microns in thickness in the X, Y, and Z axes. In further embodiments, the construct further comprises an extrusion compound, the extrusion compound improving the suitability of the cells for bioprinting. In some embodiments, the construct is substantially free of pre-formed scaffold at the time of use. In some embodiments, the liver cells are derived from one or more of the following sources: adult mammalian liver tissue; fetal mammalian liver tissue; embryonic stem cells (ESC); ESC-derived hepatocyte-like cells, induced pluripotent stem cells (IPSC); IPSC-derived hepatocyte-like cells; adult stem/progenitor cells derived from the liver; and adult stem/progenitor cells derived from a tissue other than liver. In some embodiments, the construct further comprises one or more of the following cell types: vascular cells, endothelial cells, parenchymal cells, non-parenchymal cells, fibroblasts, mesenchymal cells, immune cells, cancer cells, Kupffer cells, stellate cells, biliary cells, sinusoidal endothelial cells, liver-derived stem/progenitor cells, and non-liver-derived stem/progenitor cells. In some embodiments, the construct comprises stem/progenitor cells that were exposed to one or more differentiation signals. In further embodiments, the differentiation signal comprises one or more of: biomechanical signals, soluble signals, and physical signals. In further embodiments, the stem/progenitor cells were exposed to one or more differentiation signals before fabrication of the construct. In further embodiments, the stem/progenitor cells were exposed to one or more differentiation signals during fabrication of the construct. In further embodiments, the stem/progenitor cells were exposed to one or more differentiation signals after fabrication of the construct. In some embodiments, the construct is for use in in vitro assays. In further embodiments, the construct is for use in one or more of: drug discovery; drug testing; preclinical research; toxicity testing; absorption, distribution, metabolism, and excretion testing (ADME); drug metabolism and pharmacokinetics testing (DMPK); disease modeling; infectious disease modeling; host disease modeling; three-dimensional biology studies; and cell-based screening. In some embodiments, the construct is for use in cell-based screening, wherein the screening is for one or more infectious diseases, liver fibrosis (e.g., cirrhosis), liver cancer, liver steatosis (e.g., fatty liver), one or more metabolic deficiencies, or one or more protein deficiencies. In further embodiments, the infectious diseases include viral infection or parasitic infection (e.g., *plasmodium* infection, etc.). In some embodiments, the construct is for use in long-term tissue toxicity studies, wherein analyses are conducted for periods >3 days and up to 6 months. In some embodiments, the construct is for use in the augmentation of one or more liver functions in humans. In further embodiments, the construct is for implantation in a subject at a site of injury, disease, or degeneration. In further embodiments, the construct is for clinical use in extracorporeal devices designed to augment or restore one or more liver functions. In some embodiments, the construct is non-innervated.

In another aspect, disclosed herein are engineered, living, three dimensional liver tissue constructs comprising: a plurality of layers, each layer comprising cylindrical bio-ink, the bio-ink axially-aligned substantially in parallel, the bio-ink comprising parenchymal liver cells; and optionally, non-parenchymal cells within or among the cylindrical bio-ink; and optionally, void spaces among the cylindrical bio-ink. In some embodiments, at least one component of the construct was bioprinted. In further embodiments, the construct further comprises an extrusion compound, the extrusion compound improving the suitability of the cells for bioprinting. In some embodiments, the parenchymal cells are derived from one or more of the following sources: adult mammalian liver tissue; fetal mammalian liver tissue; embryonic stem cells (ESC); ESC-derived hepatocyte-like cells, induced pluripotent stem cells (IPSC); IPSC-derived hepatocyte-like cells; adult stem/progenitor cells derived from the liver; and adult stem/progenitor cells derived from a tissue other than liver. In some embodiments, the non-parenchymal cells comprise one or more of: vascular cells, endothelial cells, fibroblasts, mesenchymal cells, immune cells, Kupffer cells, stellate cells, biliary epithelial cells, biliary epithelial-like cells, sinusoidal endothelial cells, liver-derived stem/progenitor cells, and non-liver-derived stem/progenitor cells. In some embodiments, the construct comprises one or more layers. In further embodiments, the construct comprises a plurality of layers, at least one layer compositionally or architecturally distinct from at least one other layer to create a laminar geometry. In some embodiments, the construct is for use in the augmentation of one or more liver functions in humans. In further embodiments, the construct is for implantation in a subject at a site of injury, disease, or degeneration. In further embodiments, the construct is for clinical use in extracorporeal devices designed to augment or restore one or more liver functions. In some embodiments, the construct is non-innervated.

In another aspect, disclosed herein are arrays of engineered living, three-dimensional liver tissue constructs, each construct comprising: one or more layers, each layer comprising one or more liver cell types, the one or more layers cohered to form a living, three-dimensional liver tissue construct, each construct characterized by having at least one of: at least one layer comprising a plurality of cell types, the cell types spatially arranged relative to each other to create a planar geometry; and a plurality of layers, at least one layer compositionally or architecturally distinct from at least one other layer to create a laminar geometry. In some embodiments, at least one component of each construct was bioprinted. In further embodiments, each construct further comprises an extrusion compound, the extrusion compound improving the suitability of the cells for bioprinting. In some embodiments, each construct is substantially free of pre-formed scaffold at the time of use. In some embodiments, the liver cells are derived from one or more of the following sources: adult mammalian liver tissue; fetal mammalian liver tissue; embryonic stem cells (ESC); ESC-derived hepatocyte-like cells, induced pluripotent stem cells (IPSC); IPSC-derived hepatocyte-like cells; adult stem/progenitor cells derived from the liver; and adult stem/progenitor cells derived from a tissue other than liver. In some embodiments, each construct comprises stem/progenitor cells that were exposed to one or more differentiation signals. In further embodiments, the differentiation signal comprises one or more of: biomechanical signals, soluble signals, and physical signals. In further embodiments, the stem/progenitor cells were exposed to one or more differentiation signals before fabrication of the construct. In further embodiments, the stem/progenitor cells were exposed to one or more differentiation signals during fabrication of the construct. In further embodiments, the stem/progenitor cells were exposed to one or more differentiation signals after fabrication of the construct. In some embodiments, each construct further comprises one or more of the following cell types: vascular cells, endothelial cells, parenchymal cells, non-parenchymal cells, fibroblasts, mesenchymal cells, immune cells, cancer cells, Kupffer cells, stellate cells, biliary cells, sinusoidal endothelial cells, liver-derived stem/progenitor cells, and non-liver-derived stem/progenitor cells. In some embodiments, the array is for use in in vitro assays. In further embodiments, the array is for use in one or more of: drug discovery; drug testing; preclinical research; toxicity testing; absorption, distribution, metabolism, and excretion testing (ADME); drug metabolism and pharmacokinetics testing (DMPK); disease modeling; infectious disease modeling; host disease modeling; three-dimensional biology studies; and cell-based screening. In some embodiments, the array is for use in cell-based screening, wherein the screening is for one or more infectious diseases, liver fibrosis (e.g., cirrhosis), liver cancer, liver steatosis (e.g., fatty liver), one or more metabolic deficiencies, or one or more protein deficiencies. In further embodiments, the infectious diseases include viral infection or parasitic infection (e.g., *plasmodium* infection, etc.). In some embodiments, the array is for use in long-term tissue toxicity studies, wherein analyses are conducted for periods >3 days and up to 6 months.

In another aspect, disclosed herein are arrays of engineered living, three-dimensional tissue constructs, wherein at least one of the constructs is a liver tissue construct, each liver tissue construct comprising: one or more layers, each layer comprising one or more liver cell types, the one or more layers cohered to form a living, three-dimensional liver tissue construct, the liver tissue construct characterized by having at least one of: at least one layer comprising a plurality of cell types, the cell types spatially arranged relative to each other to create a planar geometry; and a plurality of layers, at least one layer compositionally or architecturally distinct from at least one other layer to create a laminar geometry. In some embodiments, at least one component of each liver tissue construct was bioprinted. In further embodiments, each liver tissue construct further comprises an extrusion compound, the extrusion compound improving the suitability of the cells for bioprinting. In some embodiments, each liver construct was substantially free of pre-formed scaffold at the time of use. In some embodiments, the liver cells are derived from one or more of the following sources: adult mammalian liver tissue; fetal mammalian liver tissue; embryonic stem cells (ESC); ESC-derived hepatocyte-like cells, induced pluripotent stem cells (IPSC); IPSC-derived hepatocyte-like cells; adult stem/progenitor cells derived from the liver; and adult stem/progenitor cells derived from a tissue other than liver. In some embodiments, each liver tissue construct comprises stem/progenitor cells that were exposed to one or more differentiation signals. In further embodiments, the differentiation signal comprises one or more of: biomechanical signals, soluble signals, and physical signals. In further embodiments, the stem/progenitor cells were exposed to one or more differentiation signals before fabrication of the construct. In further embodiments, the stem/progenitor cells were exposed to one or more differentiation signals during fabrication of the construct. In further embodiments, the stem/progenitor cells were exposed to one or more differentiation signals after fabrication of the construct. In some embodiments, each liver tissue construct further comprises one or more of the following cell types: vascular cells, endothelial cells, parenchymal cells, non-parenchymal cells, fibroblasts, mesenchymal cells, immune cells, cancer cells, Kupffer cells, stellate cells, biliary cells, sinusoidal endothelial cells, liver-derived stem/progenitor cells, and non-liver-derived stem/progenitor cells. In some embodiments, the array is for use in in vitro assays. In further embodiments, the array is for use in one or more of the following: tissue-tissue interactions; drug discovery; drug testing; pre-clinical research; toxicity testing; absorption, distribution, metabolism, and excretion testing (ADME); drug metabolism and pharmacokinetics testing (DMPK); disease modeling; infectious disease modeling; host disease modeling; three-dimensional biology studies; and cell-based screening. In some embodiments, the array is for use in cell-based screening, wherein the screening is for one or more infectious diseases, liver fibrosis (e.g., cirrhosis), liver cancer, liver steatosis (e.g., fatty liver), one or more metabolic deficiencies, or one or more protein deficiencies. In further embodiments, the infectious diseases include viral infection or parasitic infection (e.g., *plasmodium* infection, etc.). In some embodiments, the array is for use in long-term tissue toxicity studies, wherein analyses are conducted for periods >3 days and up to 6 months.

In another aspect, disclosed herein are methods of fabricating a living, three-dimensional liver tissue construct comprising: preparing one or more bio-inks comprising non-parenchymal cells; preparing one or more bio-inks comprising parenchymal cells; depositing the bio-inks onto a support; and incubating the deposited bio-inks for a duration of about 1 hour to about 30 days to form a living, three-dimensional liver tissue construct comprising at least one compartment, the compartment comprising an interior comprising parenchymal cells confined by a border comprising non-parenchymal cells. In some embodiments, the non-parenchymal cells comprise one or more of: vascular cells, endothelial cells, fibroblasts, mesenchymal cells, immune cells, cancer cells, Kupffer cells, stellate cells, biliary epithelial cells, biliary epithelial-like cells, sinusoidal endothelial cells, liver-derived stem/progenitor cells, and non-liver-derived stem/progenitor cells. In some embodiments, the parenchymal cells are derived from one or more of the following sources: adult mammalian liver tissue; fetal mammalian liver tissue; embryonic stem cells (ESC); ESC-derived hepatocyte-like cells, induced pluripotent stem cells (IPSC); IPSC-derived hepatocyte-like cells; adult stem/progenitor cells derived from the liver; and adult stem/progenitor cells derived from a tissue other than liver. In some embodiments, at least one component of the construct is bioprinted. In further embodiments, the construct further comprises an extrusion compound, the extrusion compound improving the suitability of the cells for bioprinting. In some embodiments, the construct is substantially free of any pre-formed scaffold at the time of use. In some embodiments, the construct is non-innervated.

In another aspect, disclosed herein are methods of fabricating an engineered living, three-dimensional liver tissue construct comprising: preparing one or more bio-inks comprising liver cells; depositing the one or more bio-inks onto a support; and incubating the one or more deposited bio-inks for a duration of about 1 hour to about 30 days; wherein the construct comprises one or more layers, each layer comprising one or more cell types, the one or more layers cohered to form a living, three-dimensional liver tissue construct. In some embodiments, the liver cells are derived from one or more of the following sources: adult mammalian liver tissue; fetal mammalian liver tissue; embryonic stem cells (ESC); ESC-derived hepatocyte-like cells, induced pluripotent stem cells (IPSC); IPSC-derived hepatocyte-like cells; adult stem/progenitor cells derived from the liver; and adult stem/progenitor cells derived from a tissue other than liver. In some embodiments, the construct further comprising one or more of the following cell types: vascular cells, endothelial cells, parenchymal cells, non-parenchymal cells, fibroblasts, mesenchymal cells, immune cells, cancer cells, Kupffer cells, stellate cells, biliary cells, sinusoidal endothelial cells, liver-derived stem/progenitor cells, and non-liver-derived stem/progenitor cells. In some embodiments, the construct is characterized by having at least one of: at least one layer comprising a plurality of cell types, the cell types spatially arranged relative to each other to create a planar geometry; and a plurality of layers, at least one layer compositionally or architecturally distinct from at least one other layer to create a laminar geometry. In some embodiments, at least one component of the construct is bioprinted. In further embodiments, the construct further comprises an extrusion compound, the extrusion compound improving the suitability of the cells for bioprinting. In some embodiments, the construct is substantially free of any pre-formed scaffold at the time of use. In some embodiments, the construct is non-innervated.

In another aspect, disclosed herein are methods of constructing a living, three-dimensional liver tissue construct comprising: preparing one or more cohered multicellular aggregates comprising mammalian liver cells; placing said one or more cohered multicellular aggregates onto a support to form at least one of: at least one layer comprising a plurality of cell types, the cell types spatially arranged relative to each other to create a planar geometry; and a plurality of layers, at least one layer compositionally or architecturally distinct from at least one other layer to create a laminar geometry; and incubating said one or more multicellular aggregates for a duration of about 1 hour to about 30 days to allow them to cohere and to form a living, three-dimensional liver tissue construct. In some embodiments, the liver cells are derived from one or more of the following sources: adult mammalian liver tissue; fetal mammalian liver tissue; embryonic stem cells (ESC); ESC-derived hepatocyte-like cells, induced pluripotent stem cells (IPSC); IPSC-derived hepatocyte-like cells; adult stem/progenitor cells derived from the liver; and adult stem/progenitor cells derived from a tissue other than liver. In some embodiments, the liver tissue construct further comprises one or more of the following cell types: vascular cells, endothelial cells, parenchymal cells, non-parenchymal cells, fibroblasts, mesenchymal cells, immune cells, cancer cells, Kupffer cells, stellate cells, biliary cells, sinusoidal endothelial cells, liver-derived stem/progenitor cells, and non-liver-derived stem/progenitor cells. In some embodiments, at least one component of the construct was bioprinted. In some embodiments, the construct further comprises an extrusion compound, the extrusion compound improving the suitability of the cells for bioprinting. In some embodiments, the construct is free of any pre-formed scaffold at the time of bioprinting or the time of use. In some embodiments, the construct is non-innervated.

In another aspect, disclosed herein are methods of fabricating a living, three-dimensional liver tissue construct comprising incubating one or more bio-inks comprising non-parenchymal cells and one or more bio-inks comprising parenchymal cells deposited onto a support for a duration of about 1 hour to about 30 days to form a living, three-dimensional liver tissue construct, the construct comprising at least one compartment, the compartment comprising an interior comprising parenchymal cells confined by a border comprising non-parenchymal cells.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
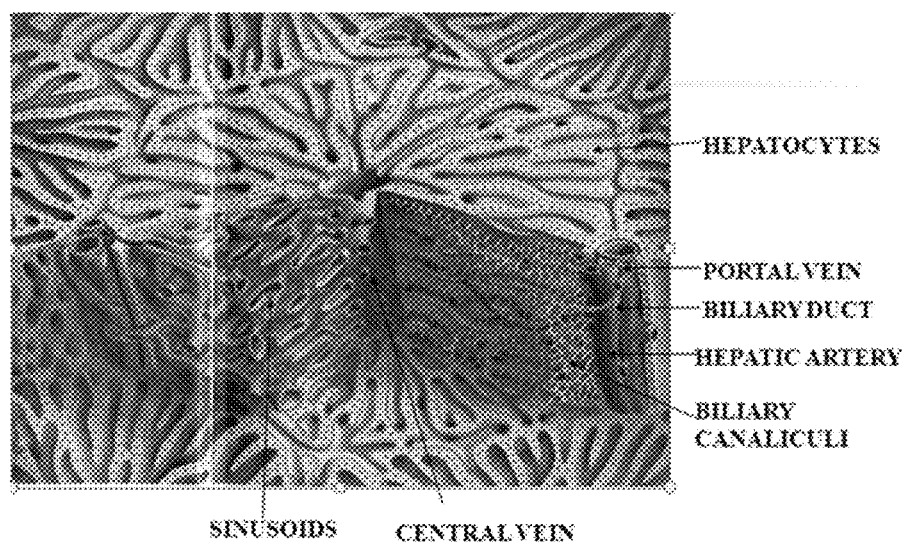
FIG. 1 is a non-limiting, exemplary illustration of native liver tissue geometry.

For many patients with liver failure, restoration of even partial liver mass through the delivery of healthy cells or tissue can have a meaningful impact on survival and liver function. According to the 2011 UNOS database, there were >10,000 patients awaiting a liver transplant in the US, with <50% of those patients actually receiving a transplanted liver. Far more patients could benefit from a transplanted liver than make it onto the transplant list, which is typically reserved for the sickest patients. Furthermore, many individuals suffer from chronic degenerative diseases for which transplantation is not a current healthcare paradigm. Thus, living, functional liver tissues would be of great clinical value. Segmental, or partial liver transplants are now performed routinely in the US, wherein a single organ is divided into 2-3 sections, or lobes, with each piece transplanted into a wait-listed patient. Because healthy liver tissue has a unique ability to grow and accommodate an individual according to their size and metabolic needs, the approach of partial-mass transplant is clinically viable.

Furthermore, many compounds fail in late-stage clinical trials or post-market due to unpredicted toxicity, which accounts for 35% of compound failures in Phase III (Curr. Pharm. Des. 2005 11:3545). Unpredicted liver toxicity accounts for the majority of those failures, followed by cardiotoxicity and renal toxicity. Thus, better systems are needed to provide a more accurate prediction of human in vivo performance.

There is a need for materials, tools, and techniques that substantially increase the number and quality of innovative, cost-effective new medicines, without incurring unsustainable R&D costs. Accordingly, the inventors describe herein engineered liver tissue constructs, arrays thereof, and methods of making the same that have utility in tissue and organ engineering, in vitro assays, drug discovery, and other areas.

Previous models of liver tissue have been focused on providing engineered tissue constructs by seeding cells onto a three-dimensional scaffold material that is pre-formed and shaped to accommodate the intended application, or by allowing liver cells to form multicellular spheroids via random assembly, wherein a spherical aggregate of cells is generated but there is no directed architecture within the aggregate. Cells seeded onto scaffold materials have been primary cells, cell lines, engineered cells, and/or stem/ progenitor cells. When multipotential stem or progenitor cells are utilized, they have either undergone a differentiation program in two-dimensional monolayer culture prior to seeding on a three-dimensional scaffold material, or they have first been seeded onto a scaffold material and then been subjected to a differentiation program, in situ or in vitro, to generate the desired tissue. The traditional approach is both laborious and inefficient in terms of cell yield, the time required for terminal differentiation of the cells within the construct, and the overall cellularity and architecture of the resulting three-dimensional structure.

Disclosed herein, in certain embodiments, are engineered, living, three-dimensional liver tissue constructs, the construct comprising at least one compartment defining a planar geometry, the compartment comprising an interior defined by a border, the interior comprising parenchymal cells, the border comprising non-parenchymal cells; the cells cohered to form a living, three-dimensional liver tissue construct; provided that at least one component of the construct was bioprinted and the construct is substantially free of pre-formed scaffold at the time of use.

Also disclosed herein, in certain embodiments, are engineered, living, three-dimensional liver tissue constructs comprising: one or more layers, each layer comprising one or more liver cell types, the one or more layers cohered to form a living, three-dimensional liver tissue construct, the construct characterized by having at least one of: at least one layer comprising a plurality of cell types, the cell types spatially arranged relative to each other to create a planar geometry; and a plurality of layers, at least one layer compositionally or architecturally distinct from at least one other layer to create a laminar geometry.

Also disclosed herein, in certain embodiments, are engineered, living, three dimensional liver tissue constructs comprising: a plurality of layers, each layer comprising cylindrical bio-ink, the bio-ink axially-aligned substantially in parallel, the bio-ink comprising parenchymal liver cells; and optionally, non-parenchymal cells within or among the cylindrical bio-ink; and optionally, void spaces among the cylindrical bio-ink.

Also disclosed herein, in certain embodiments, are arrays of engineered living, three-dimensional liver tissue constructs, each construct comprising: one or more layers, each layer comprising one or more liver cell types, the one or more layers cohered to form a living, three-dimensional liver tissue construct, each construct characterized by having at least one of: at least one layer comprising a plurality of cell types, the cell types spatially arranged relative to each other to create a planar geometry; and a plurality of layers, at least one layer compositionally or architecturally distinct from at least one other layer to create a laminar geometry.

Also disclosed herein, in certain embodiments, are arrays of engineered living, three-dimensional tissue constructs, wherein at least one of the constructs is a liver tissue construct, each liver tissue construct comprising: one or more layers, each layer comprising one or more liver cell types, the one or more layers cohered to form a living, three-dimensional liver tissue construct, the liver tissue construct characterized by having at least one of: at least one layer comprising a plurality of cell types, the cell types spatially arranged relative to each other to create a planar geometry; and a plurality of layers, at least one layer compositionally or architecturally distinct from at least one other layer to create a laminar geometry.

Also disclosed herein, in certain embodiments, are methods of fabricating a living, three-dimensional liver tissue construct comprising: preparing one or more bio-inks comprising non-parenchymal cells; preparing one or more bio-inks comprising parenchymal cells; depositing the bio-inks onto a support; and incubating the deposited bio-inks for a duration of about 1 hour to about 30 days to form a living, three-dimensional liver tissue construct comprising at least one compartment, the compartment comprising an interior comprising parenchymal cells confined by a border comprising non-parenchymal cells.

Also disclosed herein, in certain embodiments, are methods of fabricating an engineered living, three-dimensional liver tissue construct comprising: preparing one or more bio-inks comprising liver cells; depositing the one or more bio-inks onto a support; and incubating the one or more deposited bio-inks for a duration of about 1 hour to about 30 days; wherein the construct comprises one or more layers, each layer comprising one or more cell types, the one or more layers cohered to form a living, three-dimensional liver tissue construct.

Also disclosed herein, in certain embodiments, are methods of constructing a living, three-dimensional liver tissue construct comprising: preparing one or more cohered multicellular aggregates comprising mammalian liver cells; placing said one or more cohered multicellular aggregates onto a support to form at least one of: at least one layer comprising a plurality of cell types, the cell types spatially arranged relative to each other to create a planar geometry; and a plurality of layers, at least one layer compositionally or architecturally distinct from at least one other layer to create a laminar geometry; and incubating said one or more multicellular aggregates for a duration of about 1 hour to about 30 days to allow them to cohere and to form a living, three-dimensional liver tissue construct.

Also disclosed herein, in certain embodiments, are methods of fabricating a living, three-dimensional liver tissue construct comprising incubating one or more bio-inks comprising non-parenchymal cells and one or more bio-inks comprising parenchymal cells deposited onto a support for a duration of about 1 hour to about 30 days to form a living, three-dimensional liver tissue construct, the construct comprising at least one compartment, the compartment comprising an interior comprising parenchymal cells confined by a border comprising non-parenchymal cells.

Certain Definitions

Unless otherwise defined, all technical and scientific terms used herein have the same meaning as commonly understood by one of ordinary skill in the art to which this invention belongs.

As used in this specification and the appended claims, the singular forms "a," "an," and "the" include plural references unless the context clearly dictates otherwise. Thus, for example, references to "a nucleic acid" includes one or more nucleic acids, and/or compositions of the type described herein which will become apparent to those persons skilled in the art upon reading this disclosure and so forth. Any reference to "or" herein is intended to encompass "and/or" unless otherwise stated.

As used herein, "array" means a scientific tool including an association of multiple elements spatially arranged to allow a plurality of tests to be performed on a sample, one or more tests to be performed on a plurality of samples, or both.

As used herein, "assay" means a procedure for testing or measuring the presence or activity of a substance (e.g., a chemical, molecule, biochemical, protein, hormone, or drug, etc.) in an organic or biologic sample (e.g., cell aggregate, tissue, organ, organism, etc.).

As used herein, "biocompatible" means posing limited risk of injury or toxicity to cells. As presented in the specification and claims, "biocompatible multi-well containers" and "biocompatible membranes" pose limited risk of injury or toxicity to mammalian cells, but the definition does not extend to imply that these biocompatible elements could be implanted in vivo into a mammal.

As used herein, "bio-ink" means a liquid, semi-solid, or solid composition for use in bioprinting. In some embodiments, bio-ink comprises cell solutions, cell aggregates, cell-comprising gels, multicellular bodies, or tissues. In some embodiments, the bio-ink additionally comprises support material. In some embodiments, the bio-ink additionally comprises non-cellular materials that provide specific biomechanical properties that enable bioprinting. In some embodiments the bio-ink comprises an extrusion compound.

As used herein, "bioprinting" means utilizing three-dimensional, precise deposition of cells (e.g., cell solutions, cell-containing gels, cell suspensions, cell concentrations, multicellular aggregates, multicellular bodies, etc.) via methodology that is compatible with an automated or semi-automated, computer-aided, three-dimensional prototyping device (e.g., a bioprinter).

As used herein, "cohere," "cohered," and "cohesion" refer to cell-cell adhesion properties that bind cells, cell aggregates, multicellular aggregates, multicellular bodies, and/or layers thereof. The terms are used interchangeably with "fuse," "fused," and "fusion."

As used herein, "cylindrical" means having substantially the form of a cylinder. In various embodiments, cylindrical bio-ink has substantially the form of a cylinder and is about 99, 98, 97, 96, 95, 94, 93, 92, 91, 90, 85, 80, 75, 70, 65, or 60 percent, including increments therein, cylindrical in form. In further various embodiments, cylindrical bio-ink has substantially the form of a cylinder along about 99, 98, 97, 96, 95, 94, 93, 92, 91, 90, 85, 80, 75, 70, 65, 60, 55, or 50 percent, including increments therein, of its length. In some embodiments, "cylindrical" means having substantially the form of a cylinder at the time of fabrication.

As used herein, "laminar" means a multi-layered bioprinted tissue in which two or more planar layers are combined to increase the overall thickness of the tissue in the Z-plane. In some embodiments, each planar layer is substantially similar in architecture and/or composition. In other embodiments, each planar layer is substantially distinct in architecture and/or composition.

As used herein, "layer" means an association of cells in X and Y planes that is multiple cells thick. In some embodiments, the engineered liver tissues describe herein include one layer. In other embodiments, the engineered liver tissues describe herein include a plurality of layers. In various embodiments, a layer forms a contiguous, substantially contiguous, or non-contiguous sheet of cells. In some embodiments, each layer of an engineered liver tissue described herein comprises multiple cells in the X, Y, and Z axes. In further embodiments, each layer of the engineered liver tissue is at least about 50 microns in thickness in the X, Y, and Z axes.

As used herein, "multi-layered" means being comprised of two or more layers of tissue, wherein each tissue layer is one or more cell-layers in thickness. In some embodiments, layers of tissue are deposited one at a time. In other embodiments, multiple layers are deposited simultaneously. Optionally, each layer is comprised of multiple cell types.

Further, the multiple cell types within each layer are optionally arranged relative to each other in a spatially-defined architecture in the X-Y planes (i.e., horizontal planes). Furthermore, addition of layers in the Z-plane (i.e., vertical plane), in some cases, results in controlled spatial positioning of the cells within the layers relative to each other so that a spatially-defined architecture is continued in the Z-plane.

As used herein, "multi-potent cells" refers to cells that are capable of undergoing differentiation to two or more cell types. Multi-potent cells include, for example, mesenchymal stem/stromal cells, induced pluripotent stem cells, and embryonic stem cells.

As used herein, "parenchymal cells" refers to hepatocytes or hepatocyte-like cells;

whereas, "non-parenchymal cells" refers to liver cells that are not hepatocytes or hepatocyte-like cells.

As used herein, "planar" means a layer of multicellular bioprinted tissue in which multiple bio-ink compositions and/or void spaces are spatially arranged into a defined pattern relative to each other substantially within the X-Y plane of the tissue layer. See, e.g., FIGS. 18A-E. In various embodiments, a planar layer is substantially planar, for example, about 99, 98, 97, 96, 95, 94, 93, 92, 91, 90, 85, 80, 75, 70, 65, or 60 percent, including increments therein, spatially arranged into a defined pattern within the X-Y plane of the tissue layer.

As used herein, "scaffold" refers to synthetic scaffolds such as polymer scaffolds and porous hydrogels, non-synthetic scaffolds such as pre-formed extracellular matrix layers, dead cell layers, and decellularized tissues, and any other type of pre-formed scaffold that is integral to the physical structure of the engineered tissue and/or organ and not able to be removed from the tissue and/or organ without damage/destruction of said tissue and/or organ. In further embodiments, decellularized tissue scaffolds include decellularized native tissues or decellularized cellular material generated by cultured cells in any manner; for example, cell layers that are allowed to die or are decellularized, leaving behind the ECM they produced while living. The term "scaffoldless," therefore, is intended to imply that scaffold is not an integral part of the engineered tissue at the time of use, either having been removed or remaining as an inert component of the engineered tissue. "Scaffoldless" is used interchangeably with "scaffold-free" and "free of pre-formed scaffold."

As used herein, "subject" means any individual, which is a human, a non-human animal, any mammal, or any vertebrate. The term is interchangeable with "patient," "recipient" and "donor."

As used herein, "support" means any biocompatible surface capable of receiving deposited bio-ink.

As used herein, "tissue" means an aggregate of cells. Examples of tissues include, but are not limited to, connective tissue (e.g., areolar connective tissue, dense connective tissue, elastic tissue, reticular connective tissue, and adipose tissue), muscle tissue (e.g., skeletal muscle, smooth muscle and cardiac muscle), genitourinary tissue, gastrointestinal tissue, pulmonary tissue, bone tissue, nervous tissue, and epithelial tissue (e.g., simple epithelium and stratified epithelium), endoderm-derived tissue, mesoderm-derived tissue, and ectoderm-derived tissue.

Tissue Engineering

Tissue engineering is an interdisciplinary field that applies and combines the principles of engineering and life sciences toward the development of biological substitutes that restore, maintain, or improve tissue function through augmentation, repair, or replacement of an organ or tissue. The basic approach to classical tissue engineering is to seed living cells into a biocompatible and eventually biodegradable environment (e.g., a scaffold), and then culture this construct in a bioreactor so that the initial cell population expands further and matures to generate the target tissue upon implantation. With an appropriate scaffold that mimics the biological extracellular matrix (ECM), the developing tissue, in some cases, adopts both the form and function of the desired organ after in vitro and in vivo maturation. However, achieving high enough cell density with a native tissue-like architecture is challenging due to the limited ability to control the distribution and spatial arrangement of the cells throughout the scaffold. These limitations often result in tissues or organs with poor mechanical properties and/or insufficient function. Additional challenges exist with regard to biodegradation of the scaffold, entrapment of residual polymer, and industrial scale-up of manufacturing processes. Scaffoldless approaches have been attempted. Current scaffoldless approaches are subject to several limitations:

Complex planar and/or laminar geometries, such as multi-layered structures wherein one or more layers is compositionally or architecturally distinct from other layers or wherein one or more layers comprise multiple cell types in spatially-defined positions relative to each other, often require definitive, high-resolution placement of cell types within a specific architecture to reproducibly achieve a native tissue-like outcome.

Scale and geometry are limited by diffusion and/or the requirement for functional vascular networks for nutrient supply.

The viability of the tissues is, in some cases, compromised by confinement material that limits diffusion and restricts the cells' access to nutrients.

Disclosed herein, in certain embodiments, are engineered mammalian tissues, engineered liver tissues/constructs, arrays thereof, and methods of fabrication. The tissue engineering methods disclosed herein have the following advantages:

They are capable of producing cell-comprising tissues and/or organs.

They mimic the environmental conditions found within the development, homeostasis, and/or pathogenesis of natural tissues by re-creating native tissue-like intercellular interactions.

They optionally achieve living, three-dimensional tissues and compound tissues with a broad array of complex topologies and geometries (e.g., multilayered structures, segments, sheets, tubes, sacs, etc.).

They are compatible with automated or semi-automated means of manufacturing and are scalable.

Bioprinting enables improved methods of generating micro-scale tissue analogues including those useful for in vitro assays (see below).

Bioprinting

In some embodiments, at least one component of the engineered liver tissues/constructs, and arrays thereof is bioprinted. In further embodiments, bioprinted constructs are made with a method that utilizes a rapid prototyping technology based on three-dimensional, automated, computer-aided deposition of cells, including cell solutions, cell suspensions, cell-comprising gels or pastes, cell concentrations, multicellular bodies (e.g., cylinders, spheroids, ribbons, etc.), and, optionally, confinement material onto a biocompatible support surface (e.g., composed of hydrogel and/or a porous membrane) by a three-dimensional delivery device (e.g., a bioprinter). As used herein, in some embodiments, the term "engineered," when used to refer to tissues and/or organs means that cells, cell solutions, cell suspensions, cell-comprising gels or pastes, cell concentrates, multicellular aggregates, and layers thereof are positioned to form three-dimensional structures by a computer-aided device (e.g., a bioprinter) according to a computer script. In further embodiments, the computer script is, for example, one or more computer programs, computer applications, or computer modules. In still further embodiments, three-dimensional tissue structures form through the post-printing fusion of cells or multicellular bodies which, in some cases, is similar to self-assembly phenomena in early morphogenesis.

Figure 9:
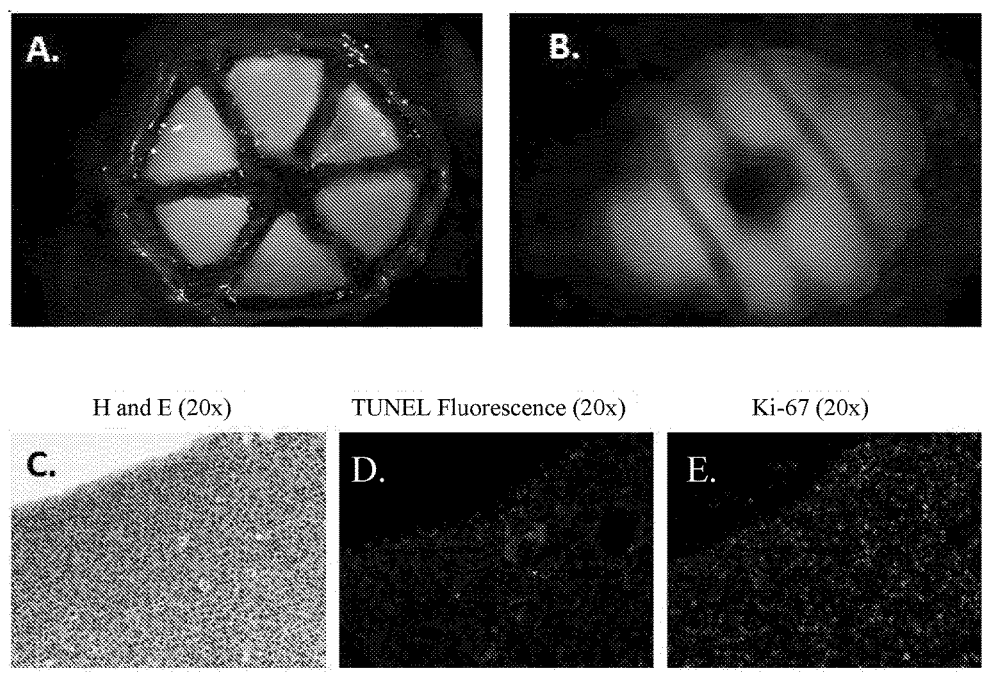
FIG. 9 is a non-limiting example of a co-printed mold (4% Gelatin and 2% Alginate) bio-printed using a Syringe Deposition Module (SDM) of a MMX Bioprinter produces constructs (A) that fuse and mature into hepatic tissues 72 hours post print (B). In this example, the bio-printed tissue is dense demonstrated by the H and E staining (C) and viable as demonstrated by relatively fewer TUNEL stained cells (D) compared to proliferating cells (E).

While a number of methods are available to arrange cells, multicellular aggregates, and/or layers thereof on a biocompatible surface to produce a three-dimensional structure including manual placement, positioning by an automated, computer-aided machine such as a bioprinter is advantageous. Advantages of delivery of cells or multicellular bodies with this technology include rapid, accurate, and reproducible placement of cells or multicellular bodies to produce constructs exhibiting planned or pre-determined orientations or patterns of cells, multicellular aggregates and/or layers thereof with various compositions. Advantages also include assured high cell density, while minimizing cell damage. Parenchymal cells of the liver are particularly susceptible to damage by shear force and other biomechanical stress; thus the combined use of bio-ink and the bioprinting process described herein provides a distinct advantage over alternative technologies as highlighted by the favorable viability of the parenchymal cells after bioprinting as highlighted in FIG. 9.

In some embodiments, the method of bioprinting is continuous and/or substantially continuous. A non-limiting example of a continuous bioprinting method is to dispense bio-ink (i.e., cells, cells combined with an excipient or extrusion compound, or aggregates of cells) from a bioprinter via a dispense tip (e.g., a syringe, needle, capillary tube, etc.) connected to a reservoir of bio-ink. In further non-limiting embodiments, a continuous bioprinting method is to dispense bio-ink in a repeating pattern of functional units. In various embodiments, a repeating functional unit has any suitable geometry, including, for example, circles, squares, rectangles, triangles, polygons, and irregular geometries, thereby resulting in one or more tissue layers with planar geometry achieved via spatial patterning of distinct bio-inks and/or void spaces. In further embodiments, a repeating pattern of bioprinted function units comprises a layer and a plurality of layers are bioprinted adjacently (e.g., stacked) to form an engineered tissue or organ with laminar geometry. In various embodiments, 2, 3, 4, 5, 6, 7, 8, 9, 10, 11, 12, 13, 14, 15, or more layers are bioprinted adjacently (e.g., stacked) to form an engineered tissue or organ. In further embodiments, one or more layers of a tissue with laminar geometry also has planar geometry.

In some embodiments, a functional unit consists of a number of fused or cohered tubular structures which are arranged in both the horizontal and vertical dimensions to form a contiguous liver tissue structure that contains void spaces or channels at regular intervals which allows perfusion across and/or through the engineered liver tissue. See FIGS. 17 and 19.

In some embodiments, a bioprinted functional unit repeats in a tessellated pattern. A "tessellated pattern" is a plane of figures that fills the plane with no overlaps and no gaps. FIG. 6A shows an example of a functional unit that is optionally repeated to produce the tessellation pattern depicted in FIGS. 6B-D and 7. Advantages of continuous and/or tessellated bioprinting includes, by way of non-limiting example, increased productivity of bioprinted tissue. Another non-limiting, exemplary advantage is eliminating the need to align the bioprinter with previously deposited elements of bio-ink. In some embodiments, continuous bioprinting facilitates printing larger tissues from a large reservoir of bio-ink, optionally using a syringe mechanism. Continuous bioprinting is also a convenient way to co-print spatially-defined boundaries, using an extrusion compound, a hydrogel, a polymer, bio-ink, or any printable material that is capable of retaining its shape post-printing; wherein the boundaries that are created are optionally filled in via the bioprinting of a one or more bio-inks, thereby creating a mosaic tissue with spatially-defined planar geometry, see for example, the embodiments illustrated in FIGS. 3A, 5A, 5B, 6, 8, and 11.

In some embodiments, methods in continuous bioprinting involve optimizing and/or balancing parameters such as print height, pump speed, robot speed, or combinations thereof independently or relative to each other. In certain cases, the bioprinter head speed for deposition was 3 mm/s, with a dispense height of 0.5 mm for the first layer and dispense height was increased 0.4 mm for each subsequent layer. In some embodiments, the dispense height is approximately equal to the diameter of the bioprinter dispense tip. Without limitation a suitable and/or optimal dispense distance does not result in material flattening or adhering to the dispensing needle. In various embodiments, the bioprinter dispense tip has an inner diameter of about, 20, 50, 100, 150, 200, 250, 300, 350, 400, 450, 500, 550, 600, 650, 700, 750, 800, 850, 900, 950, 1000 µm, or more, including increments therein. In various embodiments, the bio-ink reservoir of the bioprinter has a volume of about 0.05, 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100 cubic centimeters, or more, including increments therein. The pump speed is, in some cases, suitable and/or optimal when the residual pressure build-up in the system is low. Favorable pump speeds, in some cases, depend on the ratio between the cross-sectional areas of the reservoir and dispense needle with larger ratios requiring lower pump speeds. In some embodiments, a suitable and/or optimal print speed enables the deposition of a uniform line without affecting the mechanical integrity of the material.

The inventions disclosed herein include business methods. In some embodiments, the speed and scalability of the techniques and methods disclosed herein are utilized to design, build, and operate industrial and/or commercial facilities for production of engineered liver tissues and/or organs for implantation or use in generation of cell-based tools for research and development, such as in vitro assays. In further embodiments, the engineered liver tissues and/or organs and arrays thereof are produced, stored, distributed, marketed, advertised, and sold as, for example, cellular arrays (e.g., microarrays or chips), tissue arrays (e.g., microarrays or chips), and kits for biological assays and high-throughput drug screening. In other embodiments, the engineered liver tissues and/or organs and arrays thereof are produced and utilized to conduct biological assays and/or drug screening as a service.

Engineered Liver Tissues

Referring to FIG. 1, native liver tissue is comprised of multiple cell types, arranged in a distinct, spatially-patterned architecture relative to each other. Each liver lobule constitutes an operating functional unit of liver and is roughly hexagonal in shape. Parenchymal cells, or hepatocytes, largely constitute the lobules with various non-parenchymal cells (bile duct cells, sinusoidal endothelial cells, stellate cells, and Kupffer cells) in adjunct positions surrounding the lobule and radiating between the portal veins and bile ducts (along the periphery of the lobule) toward the central vein (in the center of the lobule). The positioning of non-parenchymal cells and the flow of blood and bile along the sinusoids and bile canaliculi, respectively, act together to form the proper micro-environment for the hepatocytes and thus influence the state of health and function of those cells. Various pathological conditions, like cirrhosis or fibrosis in the liver, lead to loss of critical metabolic functions as the hepatocyte microenvironment is disrupted and the architecture of the liver is progressively destroyed due to overproduction of extracellular matrix, inflammation, and production of pathogenic cytokines and growth factors.

Bioprinting enables compartmentalized liver tissue to be generated from multiple cellular inputs in 3D, thus recapitulating key elements of native tissue architecture and function. Lobulated tissues can be generated per the examples provided herein, wherein the parenchymal and non-parenchymal cells are spatially arranged relative to each other, creating a planar geometry within each layer of tissue that is fabricated. Subsequent layers can be added that either reproduce the geometry of the first layer precisely, or introduce additional features such as void spaces or channels or additional biological elements, such as tumor cells or other biological or biochemical components associated with pathogenic or reparative/regenerative processes. In addition to lobulated patterns, one can utilize the accompanying diagrams to appreciate that bioprinted tissue could be generated that reproduces specific spatial relationships within tissues, including but not limited to: vascular/parenchymal; vascular/hepatocyte; hepatocyte/bile duct; fibrotic tissue/vasculature; fibrotic tissue/hepatocyte; hepatocyte/immune cells; parenchymal/non-parenchymal, hepatic sinusoid/blood or blood surrogate. In further embodiments, the liver tissue analogues comprise: hepatocytes or hepatocyte-like cells and optionally bile duct epithelial cells and optionally, non-parenchymal cell types including, but not limited to, stellate cells, endothelial cells, kupffer cells, immune cells, or myofibroblasts.

Also disclosed herein, in certain embodiments, are engineered liver tissues comprising cohered, mammalian cells, and further comprising one or more layers of mammalian cells, wherein at least one component of the tissue was bioprinted. In some embodiments, one or more of the tissue layers is characterized by a planar geometry, wherein multiple cell types or bio-ink types and/or void spaces exist in spatially-defined positions in the X-Y planes. In some embodiments, the tissues are multi-layered wherein at least one of the layers is architecturally or compositionally distinct from the other layers, giving the tissue a characteristic laminar geometry. In further embodiments, the layers are of similar thickness in the Z-plane. In still further embodiments, the layers are of variable thickness in the Z-plane. In further embodiments, any single layer is one cell layer in thickness. In some embodiments, the tissues are liver analogues. In further embodiments, the liver tissue analogues comprise: hepatocytes or hepatocyte-like cells and optionally bile duct epithelial cells and optionally, non-parenchymal cell types including, but not limited to, stellate cells, endothelial cells, kupffer cells, immune cells, or myofibroblasts. In some embodiments, the resulting liver tissue constructs are at least about 50 microns in thickness in the x, y, and z planes.

In some embodiments, the engineered liver tissues/constructs, are bioprinted, a methodology described herein. In further embodiments, at least one component of the engineered tissue is bioprinted. In still further embodiments, additional components of the tissue are bioprinted. In some embodiments, the tissues are free of any pre-formed scaffold as described further herein at the time of manufacture or at the time of use. In some embodiments, as a result of being fabricated by tissue engineering techniques, including bioprinting, the tissues of the present invention are further distinguished from tissues developed in vivo, as part of an organism.

In some embodiments, the engineered liver tissue includes any type of mammalian cell. In various further embodiments, the engineered liver tissue includes 1, 2, 3, 4, 5, 6, 7, 8, 9, 10, 11, 12, 13, 14, 15, 16, 17, 18, 19, 20 or more cell types. In some embodiments, the cells of the engineered liver tissue are "cohered" or "adhered" to one another. In further embodiments, cohesion or adhesion refers to cell-cell adhesion properties that bind cells, multicellular aggregates, multicellular bodies, and/or layers thereof.

In some embodiments, the engineered liver tissues/constructs, include one or more layers of cells. In further embodiments, one or more of the layers is characterized by having a planar geometry. In still further embodiments, multiple layers of the engineered tissue have a planar geometry; wherein the planar geometries are variable among layers or are the same. In still further embodiments, planar geometries (X-Y planes) in individual layers are aligned in the Z-plane during fabrication so that additional geometry is created in the Z-plane in the composite tissue. In some embodiments, one or more of the layers within the multi-layered architecture is characterized further by having planar geometry.

In some embodiments, a layer of cells comprises one or more sheets of cells. In various embodiments, a sheet of cells is about 1, 2, 3, 4, 5, 6, 7, 8, 9, 10, 20, 30, 40, 50, 60, 70, 80, 90, 100 or more cells thick, including increments therein. In other various embodiments, a sheet of cells is about 3, 5, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more µm thick, including increments therein. In some embodiments, a layer of tissue comprises fused aggregates of cells. In further embodiments, prior to fusion, the aggregates of cells have, by way of non-limiting examples, a defined shape and/or architecture, being substantially spherical, elongate, substantially cylindrical and ribbon-like shape. In various embodiments, fused aggregates of cells form a layer about 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more µm thick, including increments therein.

In some embodiments, the one or more layers include any type of mammalian cell. In various further embodiments, each layer includes 1, 2, 3, 4, 5, 6, 7, 8, 9, 10, 11, 12, 13, 14, 15, 16, 17, 18, 19, 20 or more cell types. In some embodiments, the engineered liver tissues/constructs include one or more layers of endothelial cells on one or more surfaces. In other embodiments, the engineered liver tissues/constructs include one or more layers of epithelial cells on one or more surfaces.

The engineered liver tissues, in various embodiments, are any suitable size. In some embodiments, the size of bioprinted liver tissue, change over time. In further embodiments, an engineered liver tissue shrinks or contracts after bioprinting due to, for example, cell migration, cell death, intercellular interactions, contraction, or other forms of shrinkage. In other embodiments, an engineered liver tissue grows or expands after bioprinting due to, for example, cell migration, cell growth and proliferation, production of extracellular matrix or other cell-produced components of native tissue, cell/tissue maturation or other forms of expansion.

In some embodiments, the physical dimensions of the engineered liver tissues are limited by the capacity for nutrients, including oxygen, to diffuse into the interior of the construct. In various embodiments, the engineered liver tissues/constructs are at least about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 950, or 1000 µm in their smallest dimension at the time of bioprinting. In various embodiments, the engineered liver tissues are at least about 0.25, 0.5, 0.75, 1.0, 1.25, 1.5, 1.75, 2.0, 2.25, 2.5, 2.75, 3.0, 3.25, 3.5, 3.75, 4.0, 4.25, 4.5, 4.75, or 5.0 mm in their smallest dimension at the time of bioprinting. In further embodiments, the engineered liver tissues/constructs are between about 25 µm and about 500 µm in their smallest dimension at the time of bioprinting.

The engineered liver tissues, in various embodiments, are any suitable shape. In some embodiments, the shape is selected to mimic a particular natural tissue or organ. In further embodiments, the shape is selected to mimic a particular pathology, condition, or disease state. In some embodiments, the engineered liver tissues have a shape that is substantially planar. In further embodiments, planar tissues have any suitable planar geometry including, by way of non-limiting examples, square, rectangle, polygon, circle, oval, or irregular. In some embodiments, a planar geometry is generated in an engineered liver tissue by positioning specific cellular or bio-ink components and/or void spaces in the X-Y planes relative to each other.

In some embodiments, the engineered liver tissues/constructs are secured to a containment vessel by a means suitable to fix the position of the tissue in space relative to the containment vessel. In some embodiments, the engineered liver tissues are confined by a biocompatible material that provides physical support on one or more sides and constrains the space that the engineered liver tissue occupies. In further embodiments, the engineered liver tissues are affixed to a surface. In further embodiments, the engineered liver tissues are affixed to a biocompatible surface. In still further embodiments, a plurality of tissues are associated by affixation to a surface and spatially arranged to form an array, as described herein. In some embodiments, engineered liver tissues are subjected to shear force, caused by fluid flow, on one or more sides. In further embodiments, application of shear force serves to facilitate the maturation and development of a tissue and/or facilitate the migration, differentiation, proliferation, deposition of extracellular matrix, or transport of proteins or molecules into or out of cells within the tissue. In other embodiments, the engineered liver tissues are subjected to continuous or periodic perfusion, recirculation, or agitation of liquid nutrients on one or more surfaces. In other embodiments, the engineered liver tissues and arrays thereof are housed in a multi-well bioreactor that provides continuous or periodic recirculation of the liquid culture media for each construct.

Tissue Geometries

Native tissues are characterized by the presence of spatial and compositional patterns driven by the cellular and extracellular (i.e., void spaces, extracellular matrices, proteinaceous matter, etc.) components of a tissue. Inherent challenges to tissue engineering strategies that deploy synthetic scaffolding to achieve three-dimensionality is the inability to reproduce both the geometric and biologic attributes of native tissue. To date, attempts to create native tissue-like laminar or planar geometry within a scaffold structure while also enabling the incorporation of cells at a density that mimics native tissue have been hampered by technical limitations. Bioprinting overcomes both inherent challenges (planar/laminar geometry and cell density) through the spatially-defined deposition of bio-ink comprised of cells, according to the examples illustrated in FIGS. 18A-E. In some embodiments, planar geometries are created from multiple bio-ink formulations, whereby two or more tissue components (i.e., stromal, epithelial, vascular, bone, cartilage, parenchymal, cortical, medullary, papillary, lobular, etc.) are fabricated in a manner that positions each tissue component/cell population/bio-ink formulation in a defined position relative to each other in the X, Y, and/or Z planes. In some embodiments, the planar geometry incorporates void spaces. In further embodiments, the void spaces within the planar geometry accommodate fluids that mimic at least one element of bodily fluids, such as blood, lymph, bile, urine, secretions, and the like. In further embodiments, the void spaces optionally contain non-adherent cell types or bodily-fluid-derived components (e.g., blood cells, marrow cells, lymphatic cells, immune cells, cancer cells, platelets, proteins, etc.). In still further embodiments, non-adherent cell types of bodily-fluid-derived components optionally exist as a component of non-void spaces having been introduced into the cell-comprising components of the planar geometry before, during, or after fabrication. In still further embodiments, non-adherent cellular components or bodily-fluid-derived components are recruited from void spaces into cell-comprising spaces within the planar geometry as a result of intercellular interactions or response to secreted factors.

In some embodiments, fluid flow or perfusion is optionally initiated through the void spaces within a geometry. In some embodiments, planar geometries enable the generation of tissue-tissue or tissue-liquid interfaces. In further embodiments, the tissues are fabricated into containers that are optically clear to enable real-time observation of cells at the interface(s) created by the geometry.

In some embodiments, tissues comprise multiple layers wherein at least one of the layers is architecturally or compositionally distinct from other layers within the construct, thereby creating a laminar architecture in the Z-plane. Examples of laminar architecture include barrier tissues that possess an endothelial or epithelial barrier to an underlying interstitial tissue as depicted by the examples shown in FIG. 18F. In some embodiments, one or more layers of a tissue incorporate vascular or microvascular components. In further embodiments, the incorporation of vascular or microvascular components leads to the formation of microvascular or pseudovascular networks within one or more components of the engineered tissue. In some embodiments, one or more components of the tissue with laminar geometry are bioprinted. In some embodiments, one or more tissues with laminar geometry are fabricated adjacent to each other, thereby creating a tissue interface.

Figure 18:
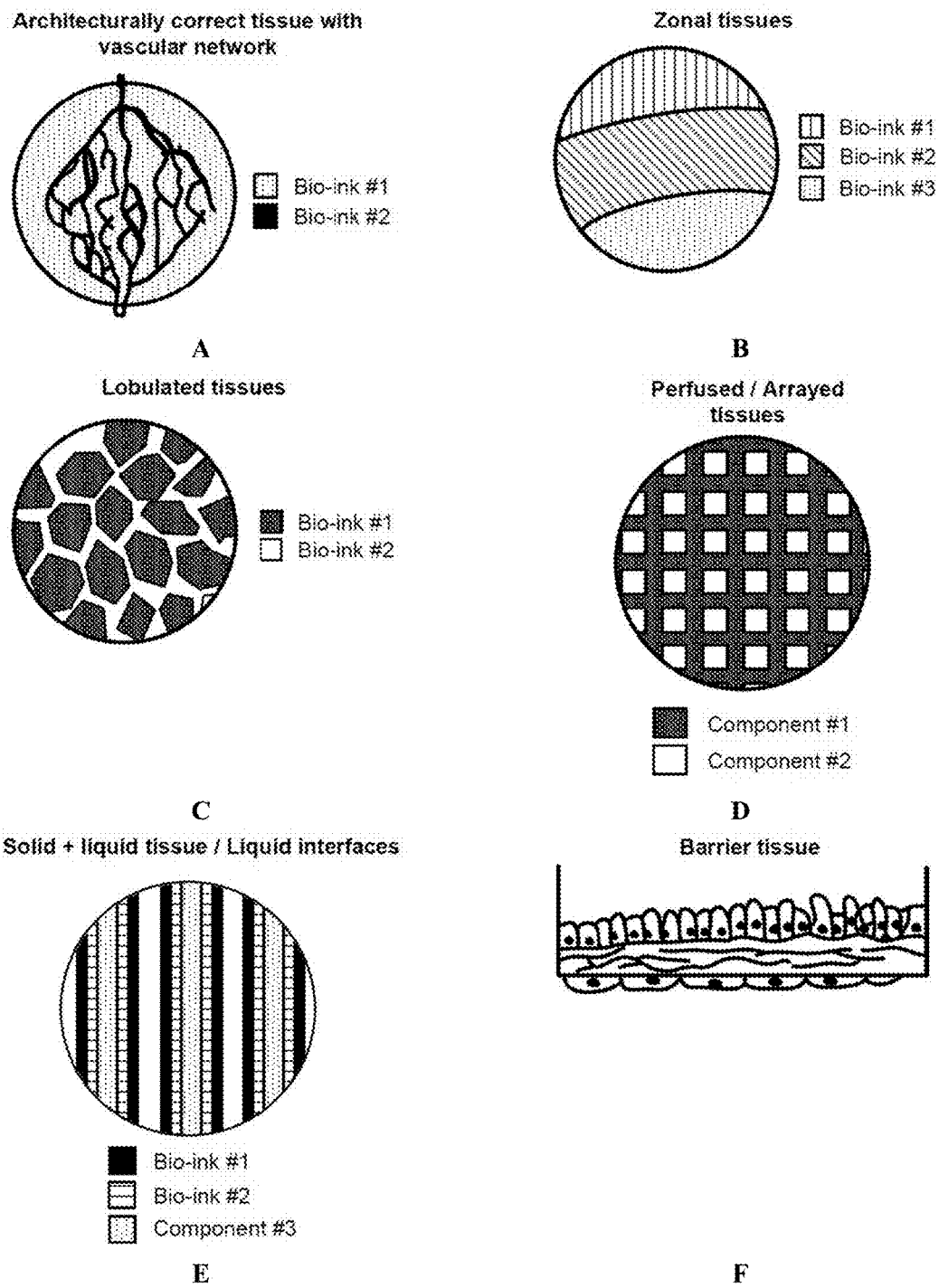
FIG. 18 is a series of non-limiting examples of planar and laminar geometries, including combinations thereof that are compatible with the methods of construction described herein, and reproduce architectural or spatial elements of native tissue architecture and biology. Exemplary geometries include an architecturally correct tissue with a vascular network (A), a zonal tissue (B), a lobulated tissue (C), a perfused/arrayed tissue (D), a tissue with a solid+liquid/liquid interface (E), a barrier tissue (F), and a layered tissue with laminar geometry (G).
Figure 18:
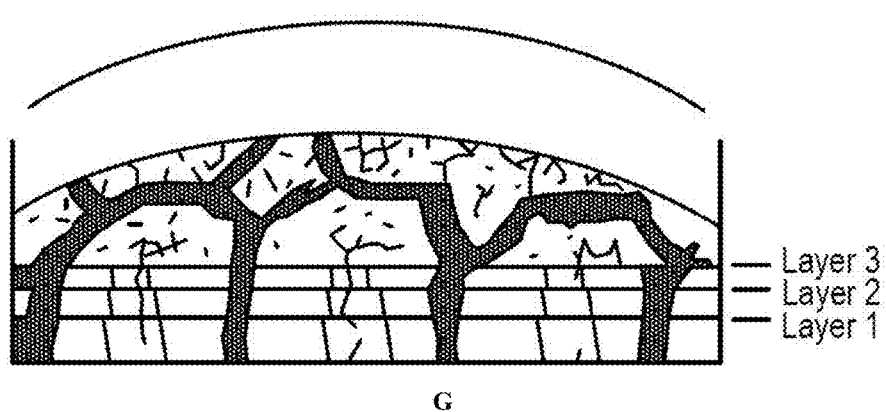

In some embodiments, one or more layers of a multi-layered engineered tissue with laminar geometry also comprise planar geometry, according to the non-limiting examples set forth in FIG. 18G. In some embodiments, the same planar geometry is continued in each layer, resulting in a three-dimensional tissue with continuous architecture in the X, Y, and Z planes. In some embodiments, the composition or planar geometry of one or more laminar layers is varied, such that the resulting three-dimensional tissue possesses a complex architecture in the X, Y and Z planes.

Referring to FIG. 18A, in a particular embodiment, an engineered liver tissue is fabricated with a planar geometry representing an architecturally-correct tissue with a vascular network. In this embodiment, an engineered liver tissue is fabricated with a first bio-ink including parenchymal cells, such as liver cells. Each layer of parenchymal cells optionally includes any planar pattern. In this embodiment, an engineered liver tissue is fabricated with a second bio-ink including vascular-related cells, such as endothelial cells, smooth muscle cells, and fibroblast to form a vascular network. Optionally, this architecture may be created by first bioprinting and establishing the vascular network, and then fabricating liver tissue surrounding that network in a second step.

Referring to FIG. 18B, in a particular embodiment, an engineered liver tissue is fabricated with a planar geometry representing a tissue zonal junction. This could be utilized, for example, to replicate the three specific zones of the hepatic acinus from the periportal region to the centrilobular region.

Referring to FIG. 18C, in a particular embodiment, an engineered liver tissue is fabricated with a planar geometry representing a lobulated tissue. In this embodiment, an engineered liver tissue is fabricated with a first bio-ink including liver cells to form lobules. Each geometric lobule optionally includes a spatially-directed architecture within its boundaries. In this embodiment, an engineered liver tissue is fabricated with a second bio-ink including stromal/vascular cells to form borders around the lobules.

Referring to FIG. 18D, in a particular embodiment, an engineered liver tissue is fabricated with a planar geometry representing a perfused/arrayed tissue. In this embodiment, a first component forms channels, vessels, or tubes with lumens. In this embodiment, a second component forms tissue patches that are optionally the same size/shape or different sizes/shapes, optionally include one cell type or a plurality of cell types, and optionally include one or more spatial patterns achieved by directed patterning in the X, Y, and or Z planes.

Referring to FIG. 18E, in a particular embodiment, an engineered liver tissue is fabricated with a planar geometry representing a solid+liquid/liquid tissue interface. In this embodiment, a first bio-ink forms the outer wall of a luminal structure, a second bio-ink forms the inner wall of a luminal structure where required, and third component is optionally a fluid containing cells or other biologically relevant components.

Referring to FIG. 18F, in a particular embodiment, an engineered liver tissue is fabricated with a laminar geometry representing a barrier tissue. In this embodiment, a barrier layer is optionally endothelial or epithelial and an interstitial layer forms the wall and/or surface of a luminal tissue, which rests upon a porous mesh or membrane.

Referring to FIG. 18G, in a particular embodiment, an engineered liver tissue is fabricated with a plurality of layers, each with a planar geometry and stacked to form a tissue with a laminar geometry. In this embodiment, the planar geometry of the X and Y axes is continued through the Z-axis into the fabricated tissue. Features of the geometry optionally include contiguous channels or cellular compartments.

Cells

Disclosed herein, in some embodiments, are engineered liver tissues (e.g., liver analogues) comprising one or more types of mammalian cells. In further embodiments, the engineered liver tissues comprise hepatocytes or hepatocyte-like cells. In still further embodiments, suitable hepatocytes or hepatocyte-like cells include, but are not limited to, primary hepatocytes, cell lines such as HepG2 cells, tissue-specific progenitors such as HepaRG cells, or combinations thereof. In further embodiments, the engineered liver tissues comprise bile duct epithelial or bile duct epithelial-like cells. In further embodiments, the engineered liver tissues comprise non-parenchymal cells. In still further embodiments, suitable non-parenchymal cells include, but are not limited to, vascular cells, endothelial cells, fibroblasts, myofibroblasts, adipocytes, adipogenic cells, mesenchymal cells, immune cells, Kupffer cells, stellate cells, biliary epithelial cells, biliary epithelial-like cells, sinusoidal endothelial cells, liver-derived stem/progenitor cells, non-liver-derived stem/progenitor cells, and combinations thereof.

In some embodiments, any mammalian cell is suitable for inclusion in the engineered liver tissues and arrays thereof. In further embodiments, at least one component of the engineered liver tissues is an adherent cell type. In further embodiments, the mammalian cells are, by way of non-limiting examples, liver cells, parenchymal cells, non-parenchymal cells, contractile or muscle cells (e.g., smooth muscle cells, and myoblasts), connective tissue cells (e.g., fibroblasts), bone marrow cells, endothelial cells, epithelial cells, vascular cells, blood cells, lymph cells, pericytes, mesothelial cells, stromal cells, undifferentiated cells (e.g., embryonic cells, stem cells, and progenitor cells), endoderm-derived cells, mesoderm-derived cells, ectoderm-derived cells, and combinations thereof.

In some embodiments, the engineered liver tissues include endothelial cells, such as human endothelial cells. In some embodiments, suitable endothelial cells originate from tissue including, by way of non-limiting example, liver tissue, blood, blood vessel, lymphatic vessel, tissue of the digestive tract, tissue of the genitourinary tract, adipose tissue, tissue of the respiratory tract, tissue of the reproductive system, bone marrow, and umbilical tissue.

In some embodiments, the cells are adult, differentiated cells. In further embodiments, "differentiated cells" are cells with a tissue-specific phenotype consistent with, for example, a hepatocyte or an endothelial at the time of isolation, wherein tissue-specific phenotype (or the potential to display the phenotype) is maintained from the time of isolation to the time of use. In other embodiments, the cells are adult, non-differentiated cells. In further embodiments, "non-differentiated cells" are cells that do not have, or have lost, the definitive tissue-specific traits. In some embodiments, non-differentiated cells include stem cells. In further embodiments, "stem cells" are cells that exhibit potency and self-renewal. Stem cells include, but are not limited to, totipotent cells, pluripotent cells, multipotent cells, oligopotent cells, unipotent cells, and progenitor cells. In various embodiments, stem cells are embryonic stem cells, adult stem cells, amniotic stem cells, and induced pluripotent stem cells. In yet other embodiments, the cells are a mixture of adult, differentiated cells and adult, non-differentiated cells.

In some embodiments, the engineered liver tissues include parenchymal cells are derived from multi-potent stem/progenitor cells. In various embodiments, the parenchymal cells are suitably derived from fetal mammalian liver tissue; embryonic stem cells (ESC); induced pluripotent stem cells (IPSC); adult stem/progenitor cells derived from the liver; and adult stem/progenitor cells derived from a tissue other than liver. In some embodiments, engineered liver tissues are derived from multi-potent stem/progenitor cells that have been either partially or fully differentiated into endodermal or hepatic phenotype prior to use in the fabrication of liver tissue constructs.

In some embodiments, the construct comprises stem/progenitor cells that have been exposed to one or more differentiation signals. In further embodiments, the differentiation signal comprises one or more of: biomechanical signals, soluble signals (e.g., a biochemical signal), and physical signals. Stem/progenitor cells are suitably exposed to one or more differentiation signals at many time points in the engineered liver tissue fabrication process. In some embodiments, the stem/progenitor cells were exposed to one or more differentiation signals before fabrication of the construct. In other embodiments, the stem/progenitor cells were exposed to one or more differentiation signals during fabrication of the construct. In yet other embodiments, the stem/progenitor cells were exposed to one or more differentiation signals after fabrication of the construct.

In various embodiments, the cell types and/or source of the cells are selected, configured, treated, or modulated based on a specific research goal or objective. In some embodiments, one or more specific cell types are selected, configured, treated, or modulated to facilitate investigation of a particular disease or condition. In some embodiments, one or more specific cell types are selected, configured, treated, or modulated to facilitate investigation of a disease or a condition of a particular subject. In some embodiments, one or more specific cell types are derived from two or more distinct human donors. In some embodiments, one or more specific cell types are derived from a particular vertebrate subject. In further embodiments, one or more specific cell types are derived from a particular mammalian subject. In still further embodiments, one or more specific cell types are derived from a particular human subject. In further embodiments, one or more specific cell types are derived from a particular subject with a specific phenotype associated with disease or tissue functionality. In still further embodiments, the subject-specific cells are isolated from the target tissue of interest by way of biopsy or tissue sampling. In further embodiments, the subject-specific cells are utilized to fabricate tissue immediately after isolation. In other embodiments, the subject-specific cells are manipulated in vitro prior to use in the fabrication of three-dimensional tissues; wherein the manipulation includes one or more of: expansion, differentiation, directed differentiation, proliferation, exposure to proteins or nucleic acids, incorporation of genetic vectors, incorporation of genetic or non-genetic cell-tracing moieties, de-differentiation (i.e., generation of induced pluripotent stem cells or equivalents), cryopreservation. In some embodiments, subject-specific cells are isolated from a tissue other than the target tissue. In further embodiments, the subject-specific cells require differentiation into cell types of interest within the target tissue. In still further embodiments, subject-specific cells that require differentiation are differentiated prior to, during, or after fabrication into a three-dimensional structure.

Methods of Culturing Cells

The cell types used in the engineered liver tissues of the invention are suitably cultured in any manner known in the art. Methods of cell and tissue culturing are known in the art, and are described, for example, in Freshney, R., *Culture of Animal Cells: A Manual of Basic Techniques*, Wiley (1987), the contents of which are incorporated herein by reference for such information. General mammalian cell culture techniques, cell lines, and cell culture systems suitably used in conjunction with the present invention are also described in Doyle, A., Griffiths, J. B., Newell, D. G., (eds.) *Cell and*

*Tissue Culture: Laboratory Procedures*, Wiley (1998), the contents of which are incorporated herein by reference for such information.

Appropriate growth conditions for mammalian cells in culture are well known in the art. Cell culture media generally include essential nutrients and, optionally, additional elements such as growth factors, salts, minerals, vitamins, platelet-rich plasma, etc., that are optionally selected according to the cell type(s) being cultured. In some embodiments, particular ingredients are selected to enhance cell growth, differentiation, secretion of specific proteins, etc. In general, standard growth media include Dulbecco's Modified Eagle Medium (DMEM) with 4 g/L glucose, supplemented with 1-20% fetal bovine serum (FBS), calf serum, or human serum, insulin (4 micrograms/mL), dexamethasone (1.0 micromolar), amphotericin B (0.25 micrograms/mL) and Glutamax (1×). Williams E media supplemented with insulin (1 g/L), sodium selenite (0.0067 g/L), transferrin (0.55 g/L), dexamethasone (1 micromolar), penicillin (100 U/mL), streptomycin (0.1 mg/mL), amphotericin B (0.25 micrograms/mL) and Glutamax (1×), or various other media known in the art. Preferably cells are cultured under sterile conditions in an atmosphere of 1-21% $O_2$ and preferably 3-5% $CO_2$, at a temperature at or near the body temperature of the animal of origin of the cell. For example, human cells are preferably cultured at approximately 37° C.

The cells are optionally cultured with cellular differentiation agents to induce differentiation of the cell along the desired line. For instance, cells are optionally cultured with growth factors, cytokines, etc. In some embodiments, the term "growth factor" refers to a protein, a polypeptide, or a complex of polypeptides, including cytokines that are produced by a cell and affect itself and/or a variety of other neighboring or distant cells. Typically growth factors affect the growth and/or differentiation of specific types of cells, either developmentally or in response to a multitude of physiological or environmental stimuli. Some, but not all, growth factors are hormones. Exemplary growth factors are insulin, insulin-like growth factor (IGF), nerve growth factor (NGF), vascular endothelial growth factor (VEGF), keratinocyte growth factor (KGF), fibroblast growth factors (FGFs), including basic FGF (bFGF), platelet-derived growth factors (PDGFs), including PDGF-AA and PDGF-AB, hepatocyte growth factor (HGF), transforming growth factor alpha (TGF-α), transforming growth factor beta (TGF-β), including TGFβ1 and TGFβ3, epidermal growth factor (EGF), granulocyte-macrophage colony-stimulating factor (GM-CSF), granulocyte colony-stimulating factor (G-CSF), interleukin-6 (IL-6), IL-8, and the like. Growth factors are discussed in, among other places, *Molecular Cell Biology*, Scientific American Books, Darnell et al., eds., 1986; *Principles of Tissue Engineering*, 2d ed., Lanza et al., eds., Academic Press, 2000. The skilled artisan will understand that any and all culture-derived growth factors in the conditioned media described herein are within the scope of the invention.

Bio-Ink and Multicellular Aggregates

Disclosed herein, in certain embodiments, are three-dimensional living tissues, including liver tissues/constructs, arrays thereof, and methods that comprise bioprinted cells. In some embodiments, cells are bioprinted by depositing or extruding bio-ink from a bioprinter. In some embodiments, "bio-ink" includes liquid, semi-solid, or solid compositions comprising a plurality of cells. In some embodiments, bio-ink comprises liquid or semi-solid cell solutions, cell suspensions, or cell concentrations. In further embodiments, a cell solution, suspension, or concentration comprises a liquid or semi-solid (e.g., viscous) carrier and a plurality of cells. In still further embodiments, the carrier is a suitable cell nutrient media, such as those described herein. In some embodiments, bio-ink comprises a plurality of cells that optionally cohere into multicellular aggregates prior to bioprinting. In further embodiments, bio-ink comprises a plurality of cells and is bioprinted to produce a specific planar and/or laminar geometry; wherein cohesion of the individual cells within the bio-ink takes place before, during and/or after bioprinting. In some embodiments, the bio-ink is produced by 1) collecting a plurality of cells in a fixed volume; wherein the cellular component(s) represent at least about 30% and at most 100% of the total volume. In some embodiments, bio-ink comprises semi-solid or solid multicellular aggregates or multicellular bodies. In further embodiments, the bio-ink is produced by 1) mixing a plurality of cells or cell aggregates and a biocompatible liquid or gel in a pre-determined ratio to result in bio-ink, and 2) compacting the bio-ink to produce the bio-ink with a desired cell density and viscosity. In some embodiments, the compacting of the bio-ink is achieved by centrifugation, tangential flow filtration ("TFF"), or a combination thereof. In some embodiments, the compacting of the bio-ink results in a composition that is extrudable, allowing formation of multicellular aggregates or multicellular bodies. In some embodiments, "extrudable" means able to be shaped by forcing (e.g., under pressure) through a nozzle or orifice (e.g., one or more holes or tubes). In some embodiments, the compacting of the bio-ink results from growing the cells to a suitable density. The cell density necessary for the bio-ink will vary with the cells being used and the tissue or organ being produced. In some embodiments, the cells of the bio-ink are cohered and/or adhered. In some embodiments, "cohere," "cohered," and "cohesion" refer to cell-cell adhesion properties that bind cells, multicellular aggregates, multicellular bodies, and/or layers thereof. In further embodiments, the terms are used interchangeably with "fuse," "fused," and "fusion." In some embodiments, the bio-ink additionally comprises support material, cell culture medium (or supplements thereof), extracellular matrix (or components thereof), cell adhesion agents, cell death inhibitors, anti-apoptotic agents, anti-oxidants, extrusion compounds, and combinations thereof.

In various embodiments, the cells are any suitable cell. In further various embodiments, the cells are vertebrate cells, mammalian cells, human cells, or combinations thereof. In some embodiments, the type of cell used in a method disclosed herein depends on the type of construct or tissue being produced. In some embodiments, the bio-ink comprises one type of cell (also referred to as a "homogeneous" or "monotypic" bio-ink). In some embodiments, the bio-ink comprises more than one type of cell (also referred to as a "heterogeneous" or "polytypic" bio-ink).

Cell Culture Media

In some embodiments, the bio-ink comprises a cell culture medium. The cell culture medium is any suitable medium. In various embodiments, suitable cell culture media include, by way of non-limiting examples, Dulbecco's Phosphate Buffered Saline, Earle's Balanced Salts, Hanks' Balanced Salts, Tyrode's Salts, Alsever's Solution, Gey's Balanced Salt Solution, Kreb's-Henseleit Buffer Modified, Kreb's-Ringer Bicarbonate Buffer, Puck's Saline, Dulbecco's Modified Eagle's Medium, Dulbecco's Modified Eagle's Medium/Nutrient F-12 Ham, Nutrient Mixture F-10 Ham (Ham's F-10), Medium 199, Minimum Essential Medium Eagle, RPMI-1640 Medium, Ames' Media, BGJb Medium (Fitton-Jackson Modification), Click's Medium, CMRL-1066 Medium, Fischer's Medium, Glascow Minimum Essential Medium (GMEM), Iscove's Modified Dulbecco's Medium (IMDM), L-15 Medium (Leibovitz), McCoy's 5A Modified Medium, NCTC Medium, Swim's S-77 Medium, Waymouth Medium, William's Medium E, or combinations thereof. In some embodiments, the cell culture medium is modified or supplemented. In some embodiments, the cell culture medium further comprises albumin, selenium, transferrins, fetuins, sugars, amino acids, vitamins, growth factors, cytokines, hormones, antibiotics, lipids, lipid carriers, cyclodextrins, platelet-rich plasma, or a combination thereof.

Extracellular Matrix

In some embodiments, the bio-ink further comprises one or more components of an extracellular matrix or derivatives thereof. In some embodiments, "extracellular matrix" includes proteins that are produced by cells and transported out of the cells into the extracellular space, where they serve as a support to hold tissues together, to provide tensile strength, and/or to facilitate cell signaling. Examples, of extracellular matrix components include, but are not limited to, collagens, fibronectin, laminins, hyaluronates, elastin, and proteoglycans. For example, in some embodiments, the multicellular aggregates contain various ECM proteins (e.g., gelatin, fibrinogen, fibrin, collagens, fibronectin, laminins, elastin, and/or proteoglycans). The ECM components or derivatives of ECM components are optionally added to the cell paste used to form the multicellular aggregate. The ECM components or derivatives of ECM components added to the cell paste are optionally purified from a human or animal source, or produced by recombinant methods known in the art. Alternatively, the ECM components or derivatives of ECM components are naturally secreted by the cells in the elongate cellular body, or the cells used to make the elongate cellular body are optionally genetically manipulated by any suitable method known in the art to vary the expression level of one or more ECM components or derivatives of ECM components and/or one or more cell adhesion molecules or cell-substrate adhesion molecules (e.g., selectins, integrins, immunoglobulins, and adherins). In some embodiments, the ECM components or derivatives of ECM components promote cohesion of the cells in the multicellular aggregates. For example, gelatin and/or fibrinogen is suitably added to the cell paste, which is used to form multicellular aggregates. The fibrinogen is converted to fibrin by the addition of thrombin.

In some embodiments, the bio-ink further comprises an agent that encourages cell adhesion.

Figure 15:
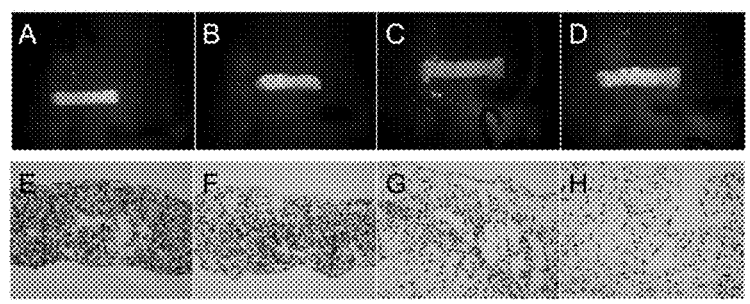
FIG. 15 is a non-limiting example of stimulation of bioprinted hepatic stellate cell tissues with TGF-β1. Incubation of bioprinted hepatic stellate cell sheets with increasing concentrations of TGF-β1 (0, 1, 10, 50 ng/mL), results in changes in gross observation of the bioprinted tissues as increases in cytokine concentration lead to increases in tissue outgrowth formation (A-D, 0-50 ng/mL). Trichrome staining of tissue sections from bioprinted hepatic stellate-containing tissues reveals increases in collagen deposition and construct size and dramatic decreases in cell density (E-H, 0-50 ng/mL).

In some embodiments, the bio-ink further comprises an agent that inhibits cell death (e.g., necrosis, apoptosis, or autophagocytosis). In some embodiments, the bio-ink further comprises an anti-apoptotic agent. Agents that inhibit cell death include, but are not limited to, small molecules, antibodies, peptides, peptibodies, or combination thereof. In some embodiments, the agent that inhibits cell death is selected from: anti-TNF agents, agents that inhibit the activity of an interleukin, agents that inhibit the activity of an interferon, agents that inhibit the activity of an GCSF (granulocyte colony-stimulating factor), agents that inhibit the activity of a macrophage inflammatory protein, agents that inhibit the activity of TGF-B (transforming growth factor B) (see, e.g., FIGS. 15 and 16), agents that inhibit the activity of an MMP (matrix metalloproteinase), agents that inhibit the activity of a caspase, agents that inhibit the activity of the MAPK/JNK signaling cascade, agents that inhibit the activity of a Src kinase, agents that inhibit the activity of a JAK (Janus kinase), or a combination thereof.

In some embodiments, the bio-ink comprises an anti-oxidant. In some embodiments, the bio-ink comprises oxygen-carriers or other cell-specific nutrients.

Extrusion Compounds

In some embodiments, the bio-ink further comprises an extrusion compound (i.e., a compound that modifies the extrusion properties of the bio-ink). Examples of extrusion compounds include, but are not limited to gels, hydrogels, peptide hydrogels, amino acid-based gels, surfactant polyols (e.g., Pluronic F-127 or PF-127), thermo-responsive polymers, hyaluronates, alginates, extracellular matrix components (and derivatives thereof), collagens, gelatin, other biocompatible natural or synthetic polymers, nanofibers, and self-assembling nanofibers. In some embodiments, extrusion compounds are removed after bioprinting by physical, chemical, or enzymatic means.

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums (e.g., tragacanth). In some embodiments, single-phase gels are generally aqueous, but will also be made using alcohols and oils. Two-phase gels consist of a network of small discrete particles.

Gels, in some cases, are classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

Suitable hydrogels include those derived from collagen, hyaluronate, hyaluronan, fibrin, alginate, agarose, chitosan, and combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, the confinement material is selected from: hydrogel, Novo-Gel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, or combinations thereof.

In some embodiments, hydrogel-based extrusion compounds are thermoreversible gels (also known as thermoresponsive gels or thermogels). In some embodiments, a suitable thermoreversible hydrogel is not a liquid at room temperature. In specific embodiments, the gelation temperature (Tgel) of a suitable hydrogel is about 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., including increments therein. In certain embodiments, the Tgel of a suitable hydrogel is about 10° C. to about 40° C. In further embodiments, the Tgel of a suitable hydrogel is about 20° C. to about 30° C. In some embodiments, the bio-ink (e.g., comprising hydrogel, one or more cell types, and other additives, etc.) described herein is not a liquid at room temperature. In some embodiments, a suitable thermoreversible hydrogel is not a liquid at mammalian body temperature. In specific embodiments, the gelation temperature (Tgel) of a suitable hydrogel is about 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 41° C., 43° C., 44° C., 45° C., 46° C., 47° C., 48° C., 49° C., 50° C., 51° C., 52° C., including increments therein. In certain embodiments, the Tgel of a suitable hydrogel is about 22° C. to about 52° C. In further embodiments, the Tgel of a suitable hydrogel is about 32° C. to about 42° C. In some embodiments, the bio-ink (e.g., comprising hydrogel, one or more cell types, and other additives, etc.) described herein is not a liquid at mammalian body temperature. In specific embodiments, the gelation temperature (Tgel) of a bio-ink described herein is about 10° C., about 15° C., about 20° C., about 25° C., about 30° C., about 35° C., about 40° C., about 45° C., about 50° C., about 55° C., including increments therein. In a specific embodiment, the Tgel of a bio-ink described herein is about 10° C. to about 15° C. In another specific embodiment, the Tgel of a bio-ink described herein is about 15° C. to about 20° C. In another specific embodiment, the Tgel of a bio-ink described herein is about 20° C. to about 25° C. In another specific embodiment, the Tgel of a bio-ink described herein is about 25° C. to about 30° C. In another specific embodiment, the Tgel of a bio-ink described herein is about 30° C. to about 35° C. In another specific embodiment, the Tgel of a bio-ink described herein is about 35° C. to about 40° C. In another specific embodiment, the Tgel of a bio-ink described herein is about 40° C. to about 45° C. In another specific embodiment, the Tgel of a bio-ink described herein is about 45° C. to about 50° C.

Polymers composed of polyoxypropylene and polyoxyethylene form thermoreversible gels when incorporated into aqueous solutions. These polymers have the ability to change from the liquid state to the gel state at temperatures maintainable in a bioprinter apparatus. The liquid state-to-gel state phase transition is dependent on the polymer concentration and the ingredients in the solution.

Poloxamer 407 (Pluronic F-127 or PF-127 or Lutrol) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer is optionally further purified by suitable methods that will enhance gelation properties of the polymer. It contains approximately 70% ethylene oxide, which accounts for its hydrophilicity. It is one of the series of poloxamer ABA block copolymers. PF-127 has good solubilizing capacity, low toxicity and is, therefore, considered a suitable extrusion compound.

In some embodiments, the viscosity of the hydrogels and bio-inks presented herein is measured by any means described. For example, in some embodiments, an LVDV-II+CP Cone Plate Viscometer and a Cone Spindle CPE-40 is used to calculate the viscosity of the hydrogels and bio-inks. In other embodiments, a Brookfield (spindle and cup) viscometer is used to calculate the viscosity of the hydrogels and bio-inks. In some embodiments, the viscosity ranges referred to herein are measured at room temperature. In other embodiments, the viscosity ranges referred to herein are measured at body temperature (e.g., at the average body temperature of a healthy human).

In further embodiments, the hydrogels and/or bio-inks are characterized by having a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise.

In some embodiments, the bio-ink comprises cells and extrusion compounds suitable for continuous bioprinting. In specific embodiments, the bio-ink has a viscosity of about 1500 mPa·s. In some embodiments, a mixture of Pluronic F-127 and cellular material is suitable for continuous bioprinting. Such a bio-ink is suitably prepared by dissolving Pluronic F-127 powder by continuous mixing in cold (4° C.) phosphate buffered saline (PBS) over 48 hours to 30% (w/v). Pluronic F-127 is also suitably dissolved in water. In some embodiments, cells are cultivated and expanded using standard sterile cell culture techniques. In further embodiments, the cells are pelleted at 200 g for example, and re-suspended in the 30% Pluronic F-127 and aspirated into a reservoir affixed to a bioprinter where it is, in some embodiments, allowed to solidify at a gelation temperature from about 10 to about 25° C. Gelation of the bio-ink prior to bioprinting is optional. The bio-ink, including bio-ink comprising Pluronic F-127 is optionally dispensed as a liquid.

In various embodiments, the concentration of Pluronic F-127 is any value with suitable viscosity and/or cytotoxicity properties. In some embodiments, a suitable concentration of Pluronic F-127 is able to support weight while retaining its shape when bioprinted. In some embodiments, the concentration of Pluronic F-127 is about 10%, about 15%, about 20%, about 25%, about 30%, about 35%, about 40%, about 45%, or about 50%. In some embodiments, the concentration of Pluronic F-127 is between about 30% and about 40%, or between about 30% and about 35%.

In some embodiments, the concentration of gelatin is 6% and the concentration of alginate is 0.5% in the extrusion compound or excipient. In other embodiments, the concentration of gelatin is 4% and the concentration of alginate is 2% in the extrusion compound or excipient.

In some embodiments, the non-cellular components of the bio-ink (e.g., extrusion compounds, etc.) are removed prior to use. In further embodiments, the non-cellular components are, for example, hydrogels, peptide hydrogels, amino acid-based gels, surfactant polyols, thermo-responsive polymers, hyaluronates, alginates, collagens, or other biocompatible natural or synthetic polymers. In still further embodiments, the non-cellular components are removed by physical, chemical, or enzymatic means. In some embodiments, a proportion of the non-cellular components remain associated with the cellular components at the time of use.

In some embodiments, the cells are pre-treated to increase cellular interaction. For example, cells are suitably incubated inside a centrifuge tube after centrifugation in order to enhance cell-cell interactions prior to shaping the bio-ink.

Exemplary Cell Ratios

In some embodiments, the bio-ink comprises multicellular bodies, which further comprise non-parenchymal liver cells (e.g. endothelial cells, hepatic stellate cells, Kupffer cells). In further embodiments, the ratio of endothelial cells to hepatic stellate cells to Kupffer cells is any suitable ratio. In further embodiments, the ratio of endothelial cells to hepatic stellate cells to Kupffer cells is about 90:10:0 to about 10:90:0. In still further embodiments, the ratio of endothelial cells to hepatic stellate cells to Kupffer cells is 45:45:10.

In some embodiments, the bio-ink comprises multicellular bodies, which further comprise hepatocytes (e.g., primary hepatocytes, HepG2 or HepaRG) and additional cell types at a ratio of 100:0. In further embodiments, the ratio of hepatocytes to additional, non-parenchymal cell types (e.g., endothelial cells) is 95:5. In further embodiments, the ratio of hepatocytes to additional, non-parenchymal cell types (e.g., endothelial cells, stellate cells) is 50:50. In still further embodiments, the ratio of parenchymal to non-parenchymal cells (e.g., endothelial cells, stellate cells, Kupffer cells) is 50:35:10:5).

Self-Sorting of Cells

In some embodiments, multicellular aggregates used to form the construct or tissue comprises all cell types to be included in the engineered tissue (e.g., hepatocytes, endothelial cells, hepatic stellate cells and kupffer cells); in such an example each cell type migrates to an appropriate position (e.g., during maturation) to form the engineered tissue, such as an engineered liver tissue. In other embodiments, the multicellular aggregates used to form the structure comprises fewer than all the cell types to be included in the engineered tissue. In some embodiments, cells of each type are uniformly distributed within a multicellular aggregates, or region or layer of the tissue. In other embodiments, cells of each type localize to particular regions within a multicellular aggregate or layers or regions of the tissue.

For example, in the case of an engineered liver tissue comprising hepatocytes, endothelial cells, hepatic stellate cells and kupffer cells, in a suitable ratio (e.g., 70:15:10:5), neighboring, bioprinted cohered polytypic bio-ink units fuse. During maturation, endothelial cells localize to some extent to both the periphery and core of the construct and organize into microvascular structures. In some embodiments, localization of cell types within a construct mimics the layered structure of in vivo or ex vivo mammalian tissues.

Pre-Formed Scaffold

In some embodiments, disclosed herein are engineered, implantable tissues and organs that are free or substantially free of any pre-formed scaffold. In further embodiments, "scaffold" refers to synthetic scaffolds such as polymer scaffolds and porous hydrogels, non-synthetic scaffolds such as pre-formed extracellular matrix layers, dead cell layers, and decellularized tissues, and any other type of pre-formed scaffold that is integral to the physical structure of the engineered tissue and/or organ and not removed from the tissue and/or organ. In still further embodiments, decellularized tissue scaffolds include decellularized native tissues or decellularized cellular material generated by cultured cells in any manner; for example, cell layers that are allowed to die or are decellularized, leaving behind the ECM they produced while living.

In some embodiments, the engineered liver tissues/constructs and arrays thereof do not utilize any pre-formed scaffold, e.g., for the formation of the tissue, any layer of the tissue, or formation of the tissue's shape. As a non-limiting example, the engineered liver tissues of the present invention do not utilize any pre-formed, synthetic scaffolds such as polymer scaffolds, pre-formed extracellular matrix layers, or any other type of pre-formed scaffold at the time of manufacture or at the time of use. In some embodiments, the engineered liver tissues are substantially free of any pre-formed scaffolds. In further embodiments, the cellular components of the tissues contain a detectable, but trace or trivial amount of scaffold, e.g., less than 2.0%, less than 1.0%, or less than 0.5% of the total composition. In still further embodiments, trace or trivial amounts of scaffold are insufficient to affect long-term behavior of the tissue, or array thereof, or interfere with its primary biological function. In additional embodiments, scaffold components are removed post-printing, by physical, chemical, or enzymatic methods, yielding an engineered tissue that is free or substantially-free of scaffold components.

In some embodiments, the engineered liver tissues free, or substantially free, of pre-formed scaffold disclosed herein are in stark contrast to those developed with certain other methods of tissue engineering in which a scaffolding material is first formed, and then cells are seeded onto the scaffold, and subsequently the cells proliferate to fill and take the shape of the scaffold for example. In one aspect, the methods of bioprinting described herein allow production of viable and useful tissues that are free or substantially free of pre-formed scaffold. In another aspect, the cells of the invention are, in some embodiments, held in a desired three-dimensional shape using a confinement material. The confinement material is distinct from a scaffold at least in the fact that the confinement material is temporary and/or removable from the cells and/or tissue.

Arrays

In some embodiments, disclosed herein are arrays of engineered liver tissues/constructs. In some embodiments, an "array" is a scientific tool including an association of multiple elements spatially arranged to allow a plurality of tests to be performed on a sample, one or more tests to be performed on a plurality of samples, or both. In some embodiments, the arrays are adapted for, or compatible with, screening methods and devices, including those associated with medium- or high-throughput screening. In further embodiments, an array allows a plurality of tests to be performed simultaneously. In further embodiments, an array allows a plurality of samples to be tested simultaneously. In some embodiments, the arrays are cellular microarrays. In further embodiments, a cellular microarray is a laboratory tool that allows for the multiplex interrogation of living cells on the surface of a solid support. In other embodiments, the arrays are tissue microarrays. In further embodiments, tissue microarrays include a plurality of separate tissues or tissue samples assembled in an array to allow the performance of multiple biochemical, metabolic, molecular, or histological analyses.

Figure 16:
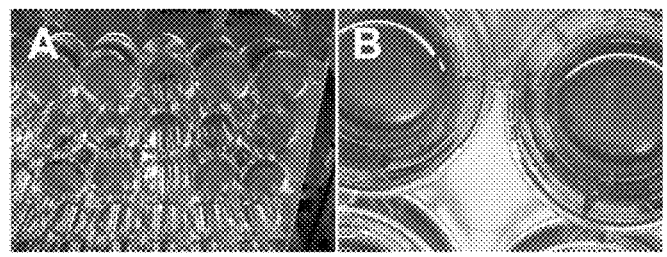
FIG. 16 is a non-limiting example of bioprinting in multi-well formats. Bioprinted tissue constructs are generated in multi-well plates (A) or within multi-well culture inserts (B), which are optionally placed in an appropriate multi-well plate for long-term maintenance and maturation. Here, tissue constructs were bioprinted in a 48-well polystyrene plate (A) and on the porous membrane of a 6-well cell culture insert (B).

In some embodiments, the engineered liver tissues/constructs each exist in a well of a biocompatible multi-well container (see, e.g., FIG. 16). In some embodiments, each tissue is placed into a well. In other embodiments, each tissue is bioprinted into a well. In further embodiments, the wells are coated. In various further embodiments, the wells are coated with one or more of: a biocompatible hydrogel, one or more proteins, one or more chemicals, one or more peptides, one or more antibodies, and one or more growth factors, including combinations thereof. In some embodiments, the wells are coated with NovoGel™. In other embodiments, the wells are coated with agarose. In some embodiments, each tissue exists on a porous, biocompatible membrane within a well of a biocompatible multi-well container. In some embodiments, each well of a multi-well container contains two or more tissues.

In some embodiments, the engineered liver tissues/constructs are secured to a biocompatible surface on one or more sides. Many methods are suitable to secure a tissue to a biocompatible surface. In various embodiments, a tissue is suitably secured to a biocompatible surface, for example, along one or more entire sides, only at the edges of one or more sides, or only at the center of one or more sides. In various further embodiments, a tissue is suitably secured to a biocompatible surface with a holder or carrier integrated into the surface or associated with the surface. In various further embodiments, a tissue is suitably secured to a biocompatible surface with one or more pinch-clamps or plastic nubs integrated into the surface or associated with the surface. In some embodiments, a tissue is suitably secured to a biocompatible surface by cell-attachment to a porous membrane. In some embodiments, the engineered liver tissues/constructs are held in an array configuration by affixation to a biocompatible surface on one or more sides. In further embodiments, the tissue is affixed to a biocompatible surface on 1, 2, 3, 4, or more sides. In some embodiments, the biocompatible surface any surface that does not pose a significant risk of injury or toxicity to the tissue or an organism contacting the tissue. In further embodiments, the biocompatible surface is any surface suitable for traditional tissue culture methods. Suitable biocompatible surfaces include, by way of non-limiting examples, treated plastics, membranes, porous membranes, coated membranes, coated plastics, metals, coated metals, glass, treated glass, and coated glass, wherein suitable coatings include hydrogels, ECM components, chemicals, proteins, etc., and coatings or treatments provide a means to stimulate or prevent cell and tissue adhesion to the biocompatible surface.

In some embodiments, securing of an engineered tissue to a biocompatible surface on one or more sides facilitates subjecting the tissue to shear force, caused by fluid flow. In further embodiments, the engineered liver tissues/constructs, are subjected to shear force, caused by fluid flow. In various embodiments, the engineered liver tissues are subjected to shear force on 1, 2, 3, 4, or more sides. In further embodiments, the engineered liver tissues/constructs are subjected to recirculation, perfusion, or agitation of the liquid nutrients that contact the tissues on one or more exposed surfaces.

In some embodiments, the arrays of engineered tissues, including liver tissues/constructs, comprise an association of two or more elements. In various embodiments, the arrays comprise an association of 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, or 500 elements, including increments therein. In further embodiments, each element comprises one or more cells, multicellular aggregates, tissues, organs, or combinations thereof.

In some embodiments, the arrays of engineered tissues, including liver tissues/constructs, comprise multiple elements spatially arranged in a pre-determined pattern. In further embodiments, the pattern is any suitable spatial arrangement of elements. In various embodiments, patterns of arrangement include, by way of non-limiting examples, a two-dimensional grid, a three-dimensional grid, one or more lines, arcs, or circles, a series of rows or columns, and the like. In further embodiments, the pattern is chosen for compatibility with medium- or high-throughput biological assay or screening methods or devices.

In various embodiments, the cell types and/or source of the cells used to fabricate one or more tissues in an array are selected based on a specific research goal or objective. In further various embodiments, the specific tissues in an array are selected based on a specific research goal or objective. In some embodiments, one or more specific engineered liver tissues are included in an array to facilitate investigation of a particular disease or condition. In some embodiments, one or more specific engineered liver tissues are included in an array to facilitate investigation of a disease or a condition of a particular subject. In further embodiments, one or more specific engineered liver tissues within the array are generated with one or more cell types derived from two or more distinct human donors. In some embodiments, each tissue within the array is substantially similar with regard to cell types, sources of cells, layers of cells, ratios of cells, methods of construction, size, shape, and the like. In other embodiments, one or more of the tissues within the array is unique with regard to cell types, sources of cells, layers of cells, ratios of cells, methods of construction, size, shape, and the like. In various embodiments, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, or more of the tissues within the array, including increments therein, is/are unique. In other various embodiments, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the tissues within the array, including increments therein, is/are unique.

In some embodiments, each tissue within the array is maintained independently in culture. In further embodiments, the culture conditions of each tissue within the array are such that they are isolated from the other tissues and cannot exchange media or factors soluble in the media. In other embodiments, two or more individual tissues within the array exchange soluble factors. In further embodiments, the culture conditions of two or more individual tissues within the array are such that they exchange media and factors soluble in the media with other tissues. In various embodiments, 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, or more of the tissues within the array, including increments therein, exchange media and/or soluble factors. In other various embodiments, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, or 100% of the tissues within the array, including increments therein, exchange media and/or soluble factors.

In Vitro Assays

In some embodiments, the engineered liver tissues and arrays disclosed herein are for use in in vitro assays. In some embodiments, an "assay" is a procedure for testing or measuring the presence or activity of a substance (e.g., a chemical, molecule, biochemical, drug, etc.) in an organic or biologic sample (e.g., cell aggregate, tissue, organ, organism, etc.). In further embodiments, assays include qualitative assays and quantitative assays. In still further embodiments, a quantitative assay measures the amount of a substance in a sample.

In various embodiments, the engineered liver tissues and arrays are for use in, by way of non-limiting examples, image-based assays, measurement of secreted proteins, expression of markers, and production of proteins. In various further embodiments, the engineered liver tissue and arrays are for use in assays to detect or measure one or more of: molecular binding (including radioligand binding), molecular uptake, activity (e.g., enzymatic activity and receptor activity, etc.), gene expression, protein expression, receptor agonism, receptor antagonism, cell signaling, apoptosis, chemosensitivity, transfection, cell migration, chemotaxis, cell viability, cell proliferation, safety, efficacy, metabolism, toxicity, infectivity, and abuse liability.

In some embodiments, the engineered liver tissues and arrays are for use in immunoassays. In further embodiments, immunoassays are competitive immunoassays or noncompetitive immunoassays. In a competitive immunoassay, for example, the antigen in a sample competes with labeled antigen to bind with antibodies and the amount of labeled antigen bound to the antibody site is then measured. In a noncompetitive immunoassay (also referred to as a "sandwich assay"), for example, antigen in a sample is bound to an antibody site; subsequently, labeled antibody is bound to the antigen and the amount of labeled antibody on the site is then measured.

In some embodiments, the engineered liver tissue and arrays are for use in enzyme-linked immunosorbent assays (ELISA). In further embodiments, an ELISA is a biochemical technique used to detect the presence of an antibody or an antigen in a sample. In ELISA, for example, at least one antibody with specificity for a particular antigen is utilized. By way of further example, a sample with an unknown amount of antigen is immobilized on a solid support (e.g., a polystyrene microtiter plate) either non-specifically (via adsorption to the surface) or specifically (via capture by another antibody specific to the same antigen, in a "sandwich" ELISA). By way of still further example, after the antigen is immobilized, the detection antibody is added, forming a complex with the antigen. The detection antibody is, for example, covalently linked to an enzyme, or is itself detected by a secondary antibody that is linked to an enzyme through bioconjugation.

For example, in some embodiments, an array, microarray, or chip of cells, multicellular aggregates, or tissues is used for drug screening or drug discovery. In further embodiments, an array, microarray, or chip of tissues is used as part of a kit for drug screening or drug discovery. In some embodiments, each engineered liver tissue/construct exists within a well of a biocompatible multi-well container, wherein the container is compatible with one or more automated drug screening procedures and/or devices. In further embodiments, automated drug screening procedures and/or devices include any suitable procedure or device that is computer or robot-assisted.

In further embodiments, arrays for drug screening assays or drug discovery assays are used to research or develop drugs potentially useful in any therapeutic area. In still further embodiments, suitable therapeutic areas include, by way of non-limiting examples, infectious disease, hematology, oncology, pediatrics, cardiology, central nervous system disease, neurology, gastroenterology, hepatology, urology, infertility, ophthalmology, nephrology, orthopedics, pain control, psychiatry, pulmonology, vaccines, wound healing, physiology, pharmacology, dermatology, gene therapy, toxicology, and immunology.

In some embodiments, the engineered liver tissue and arrays are for use in cell-based screening. In further embodiments, the cell-based screening is for one or more infectious diseases such as viral infection or parasitic infection (e.g., *plasmodium* infection, etc.). In further embodiments, the cell-based screening is for liver fibrosis (e.g., cirrhosis). In further embodiments, the cell-based screening is for liver cancer. In further embodiments, the cell-based screening is for liver steatosis (e.g., fatty liver). In further embodiments, the cell-based screening is for one or more metabolic deficiencies. In further embodiments, the cell-based screening is for one or more protein deficiencies. In other embodiments, the engineered liver tissues and arrays are for use in the study of cancer initiation, progression, or metastasis. In still further embodiments, the engineered liver tissues and arrays are for use in the study of the interaction of other cell types, such as cancer cells, pathogen-bearing cells, pathogenic cells, immune cells, blood-derived cells, or stem/progenitor cells, with liver tissue and the cells comprising liver tissue.

In some embodiments, the constructs or arrays thereof are for use in assessing the performance of biologics, including antibodies, mammalian cells, bacteria, biologically-active proteins, hormones, etc. In some embodiments the construct or arrays thereof are for use to detect, quantify, and study immunologic sampling by Kupffer and stellate cells, including the effects of gram-negative or gram-positive antigen-stimulated signaling from Kupffer or stellate cells to bordering hepatocytes (e.g., response to lipopolysaccharide (LPS)). In some embodiments, the constructs or arrays thereof are useful for the production of hepatotrophic viruses, including HBV and HCV. In further embodiments, the constructs or arrays thereof are used as a vehicle for production of *Plasmodium* spp. (a parasite) in the exo-erythrocytic form. In still further embodiments, liver construct-derived *Plasmodium* are utilized in comparative in vitro assays to identify effective therapies for exo-erythrocytic forms of the parasite. In other embodiments, the construct or arrays thereof are utilized as anti-host therapies for Hepatitis C Virus (HCV) or *Plasmodium*, including the conduct of anti-host antibody studies. In other embodiments, the liver constructs or arrays thereof are useful in the study of cancer initiation, progression, or metastasis. In other embodiments, the liver constructs or arrays thereof are useful in the study of cell-cell and cell-tissue interactions between the mammalian liver cells/tissue comprising the construct and one or more additional cell types, including but not limited to pathogen-bearing cells, living pathogenic cells, cancer cells, immune cells, blood cells, stem/progenitor cells, or genetically-manipulated cells.

In some embodiments, the array comprises engineered liver tissue constructs and additional tissue constructs. In further embodiments, the liver tissue construct is in direct contact with an additional tissue construct on one or more surfaces. In still further embodiments, the liver tissue is connected to one or more additional tissues constructs or cells via a fluid path or common fluid reservoir. In still further embodiments, the liquid media that contacts the engineered liver tissue construct contains living mammalian cells such as immune cells, blood-derived cells, or tumor-derived cells. In other embodiments, the liquid media that contacts the engineered liver tissue construct contains bacteria, viruses, parasites, or other pathogens. In some embodiments, the engineered liver tissue and arrays are for use as vehicle to propagate hepatotrophic viruses for three dimensional structural studies including X-ray or cryo-EM.

Extracorporeal Support

In some embodiments, the engineered liver tissues comprise a plurality of layers, each layer comprising cylindrical bio-ink, the bio-ink axially-aligned substantially in parallel, the bio-ink comprising parenchymal liver cells; and optionally, non-parenchymal cells among the cylindrical bio-ink; and optionally, void spaces or perfusable channels among the cylindrical bio-ink. In further embodiments, an engineered liver tissue is used to provide extracorporeal support to a subject in need thereof. In still further embodiments, blood is passed over or through the construct to filter the blood and supplement the subjects liver function.

Figure 17:
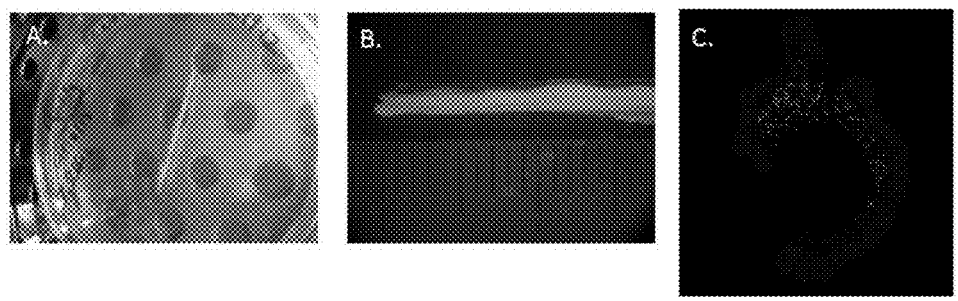
FIG. 17 is a non-limiting example of bio-printed hepatic tubular structure designed and printed for extracorporeal support (A). 40 mm length bio-ink cylinders comprising 70% HepG2/25% HUVEC/5% Hepatic Stellate were bioprinted and conditioned (B). A channel was created in the center of the structure by use of a removable, bio-inert hydrogel (C).

Referring to FIG. 17, in a particular embodiment, a bioprinted liver structure is designed for providing extracorporeal support (A). In this embodiment, a bioprinted liver structure is composed of a plurality of parenchymal cell cylinders (B). The structure also includes non-parenchymal cells and filler bodies to create compartments and/or channels through which perfusion or flow could be achieved (C).

Figure 19:
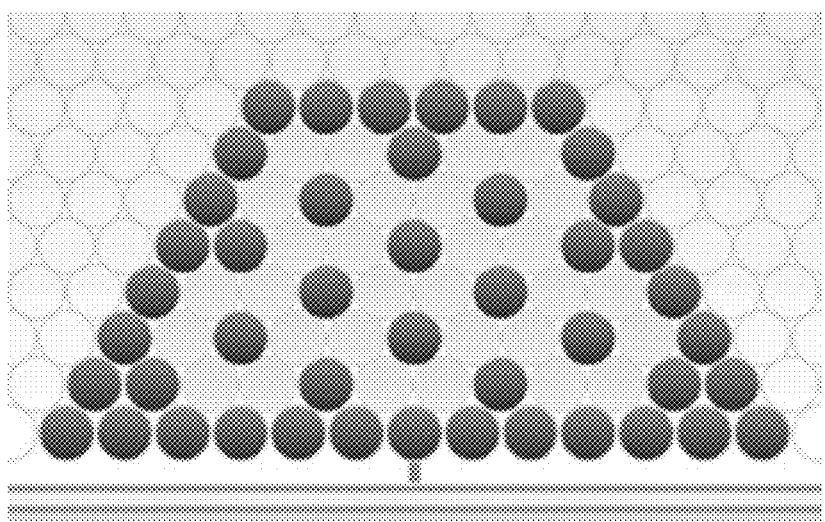
FIG. 19 is a non-limiting schematic representation of an extracorporeal hepatic device containing repeating tubular structures with void spaces (depicted as occupied by temporary filler bodies; dark circles) at regular intervals allowing perfusion across and/or through the engineered liver tissue.

Referring to FIG. 19, in a particular embodiment, a bioprinted liver structure is used as an extracorporeal hepatic device containing repeating tubular structures with void spaces (depicted occupied by temporary filler bodies) at regular intervals allowing perfusion across and/or through the engineered liver tissue.

Methods

Disclosed herein, in some embodiments, are methods for constructing living, three-dimensional liver tissue constructs, the methods comprising the steps of bioprinting bio-ink comprising at least one liver cell type into or onto a form, and fusing of the bio-ink into a living, three-dimensional tissue liver construct. In further embodiments, the tissue construct is for in vitro use.

Also disclosed herein, in some embodiments, are methods of constructing tissues, including engineered liver tissues, comprising the steps of: preparing cohered multicellular aggregates comprising either parenchymal or parenchymal and non-parenchymal cells; placing said cohered multicellular aggregates onto a support; and incubating said multicellular aggregates to allow them to cohere and form an engineered liver tissue; wherein said incubation has a duration of about 1 hours to about 30 days. In some embodiments, the methods utilize bioprinting. In further embodiments, the methods produce engineered liver tissues free or substantially free of any pre-formed scaffold at the time of use.

Also disclosed herein, in some embodiments, are methods of constructing living, three-dimensional liver tissues comprising the steps of: preparing one or more cohered multicellular aggregates comprising mammalian liver cells; placing said one or more cohered multicellular aggregates onto a support; applying, to said one or more cohered multicellular aggregates, one or more of: a layer of a first type of mammalian cells on one or more external surfaces; a layer of a second type of mammalian cells on one or more external surfaces; and incubating said one or more multicellular aggregates to allow them to cohere and to form a tissue; wherein said incubation has a duration of about 1 hour to about 30 days. In some embodiments, the methods utilize bioprinting. In further embodiments, the methods produce engineered liver tissues, free or substantially free of any pre-formed scaffold at the time of use.

Also disclosed herein, in some embodiments, are methods of constructing living, three-dimensional liver tissue constructs comprising the steps of: preparing one or more cohered multicellular aggregates comprising mammalian cells; placing said one or more cohered multicellular aggregates onto a support to form at least one of: at least one layer comprising a plurality of cell types, the cell types spatially arranged relative to each other to create a planar geometry; and/or a plurality of layers, at least one layer compositionally or architecturally distinct from at least one other layer to create a laminar geometry; and incubating said one or more multicellular aggregates to allow them to cohere and to form a living, three-dimensional liver tissue construct.

Preparing Cohered Multicellular Aggregates

In some embodiments, the methods involve preparing cohered multicellular aggregates comprising one or more types of mammalian cells, wherein at least one cellular component represents liver cells. In some embodiments, the methods involve preparing cohered multicellular aggregates comprising liver parenchymal cells. In some embodiments, the methods involve preparing cohered multicellular aggregates further comprising non-parenchymal cells. In some embodiments, the methods involve preparing cohered multicellular aggregates further comprising one or more other cell types, selected from the group: endothelial cells, stellate cells, fibroblasts, Kupffer cells, immune cells, lymphocytes, cancer cells, virus-bearing cells, pathogenic cells, adipocytes, adipogenic cells, smooth muscle cells, or stem/progenitor-derived cells.

There are various ways to make multicellular aggregates having the characteristics described herein. In some embodiments, a multicellular aggregate is fabricated from a cell paste containing a plurality of living cells or with a desired cell density and viscosity. In further embodiments, the cell paste is shaped into a desired shape and a multicellular body formed through maturation (e.g., incubation). In some embodiments, the shape of the multicellular body is determined by the shape of a surrounding mold or frame. In further embodiments, the mold or frame is fabricated by an automated instrument in a defined geometry. In still further embodiments, the mold or frame consists of bio-ink and contains liver-derived cells. In further embodiments, the mold or frame comprises liver-derived non-parenchymal cells and the paste utilized to fill the frame and create the multicellular aggregate comprises parenchymal cells. In some embodiments, the multicellular aggregates are substantially cylindrical. In other embodiments, the multicellular aggregates are hexagonal, square, cuboidal, rectangular, polyhedral. In still further embodiments, multiple multicellular aggregates are formed by fabricating the surrounding mold or frame in a tessellated pattern of repeating geometry and subsequently or simultaneously filling the molds or frames with cell paste. In further embodiments, the cell paste is incubated in a controlled environment to allow the cells to adhere and/or cohere to one another to form the elongate multicellular body. In another particular embodiment, a multicellular body is produced by shaping a cell paste including a plurality of living cells in a device that holds the cell paste in a three-dimensional shape. In further embodiments, the cell paste is incubated in a controlled environment while it is held in the three dimensional shape for a sufficient time to produce a body that has sufficient cohesion to support itself on a flat surface.

In various embodiments, a cell paste is provided by: 1) collecting cells or cell aggregates (of one or more cell types) and a biocompatible gel or liquid, such as cell culture medium (e.g., in a pre-determined ratio) to result in a cell suspension, and 2) compacting the cellular suspension to produce a cell paste with a desired cell density and viscosity. In various embodiments, compacting is achieved by a number of methods, such as by concentrating a particular cell suspension that resulted from cell culture to achieve the desired cell concentration (density), viscosity, and consistency required for the cell paste. In a particular embodiment, a relatively dilute cell suspension from cell culture is centrifuged for a determined time to achieve a cell concentration in the pellet that allows shaping in a mold. Tangential flow filtration ("TFF") is another suitable method of concentrating or compacting the cells. In some embodiments, compounds are combined with the cell suspension to lend the extrusion properties required. Suitable compounds include, by way of non-limiting examples, surfactant polyols, collagens, hydrogels, peptide hydrogels, amino acid-based gels, Matrigel™, nanofibers, self-assembling nanofibers, gelatin, fibrinogen, etc.

In some embodiments, the cell paste is produced by mixing a plurality of living cells with a tissue culture medium, and compacting the living cells (e.g., by centrifugation). One or more ECM components (or derivative of an ECM component) is optionally included by, resuspending the cell pellet in one or more physiologically acceptable buffers containing the ECM component(s) (or derivative(s) of ECM component(s)) and the resulting cell suspension centrifuged again to form a cell paste.

In some embodiments, the cell density of the cell paste desired for further processing varies with cell types. In further embodiments, interactions between cells determine the properties of the cell paste, and different cell types will have a different relationship between cell density and cell-cell interaction. In still further embodiments, the cells are pre-treated to increase cellular interactions before shaping the cell paste. For example, in some cases, cells are incubated inside a centrifuge tube after centrifugation in order to enhance cell-cell interactions prior to shaping the cell paste. In some embodiments, the cell paste is shaped concomitantly with bioprinting; wherein the cohesion of individual cells to each other to form bio-ink occurs during or after bioprinting.

In various embodiments, many methods are used to shape the cell paste. For example, in a particular embodiment, the cell paste is manually molded or pressed (e.g., after concentration/compaction) to achieve a desired shape. By way of a further example, the cell paste is taken up (e.g., aspirated) into an instrument, such as a micropipette or syringe (e.g., a capillary pipette or a glass/plastic syringe), that shapes the cell paste to conform to an interior surface of the instrument. The cross-sectional shape of the micropipette (e.g., capillary pipette) is alternatively circular, square, rectangular, triangular, or other non-circular cross-sectional shape. In some embodiments, the cell paste is shaped by depositing it into a preformed mold, such as a plastic mold, metal mold, or a gel mold. In some embodiments, centrifugal casting or continuous casting is used to shape the cell paste. In some embodiments, the shaping of the bio-ink occurs concomitantly or after bioprinting. In further embodiments, the shaping of the bio-ink occurs as the result of a co-printed mold; wherein the mold is optionally deposited via bioprinting; wherein the mold comprises one or more of: bio-ink, bio-ink that further comprises an extrusion compound, gel, hydrogel, synthetic polymer, carbohydrate, protein, or mammalian cells, or combinations thereof. In still further embodiments, one or more components of the co-printed mold are removed after bioprinting; wherein the removal method is selected from one of: physical means; solubilization with aqueous media; chemical treatment; enzymatic treatment; modulating temperature. In further embodiments, the co-printed mold remains associated with the tissue after fabrication. In still further embodiments, only the cellular component(s) of the co-printed mold remain associated with the tissue after fabrication.

In some embodiments, multicellular aggregates of a defined shape are also suitable to build the engineered liver tissues described herein. Spherical multicellular aggregates are optionally generated by a variety of methods, including, but not limited to, cellular self-assembly, the use of molds, and hanging drop methods. In further embodiments, a method to produce substantially spherical multicellular aggregates comprises the steps of 1) providing a cell paste containing a plurality of pre-selected cells or cell aggregates with a desired cell density and viscosity, 2) manipulating the cell paste into a cylindrical shape, 3) cutting cylinders into equal fragments, 4) optionally letting the fragments round up overnight on a gyratory shaker, and 5) optionally allowing the substantially spherical multicellular aggregates to mature over a period of 1 hour to 7 days. In further embodiments, multicellular aggregates are generated via acoustic focusing methodologies.

In some embodiments, a partially adhered and/or cohered cell paste is used for bioprinting; wherein cohesion and bio-ink formation occurs primarily post-printing. In other embodiments, the cellular paste is shaped in a first step prior to bioprinting. In further embodiments, the cell paste is transferred from the first shaping device (e.g., capillary pipette) to a second shaping device (e.g., a mold) that allows nutrients and/or oxygen to be supplied to the cells while they are retained in the second shaping device for an additional maturation period. One example of a suitable shaping device that allows the cells to be supplied with nutrients and oxygen is a mold for producing a plurality of multicellular aggregates (e.g., substantially identical multicellular aggregates). By way of further example, such a mold includes a biocompatible substrate made of a material that is resistant to migration and ingrowth of cells into the substrate and resistant to adherence of cells to the substrate. In various embodiments, the substrate is suitably be made of Teflon® (PTFE), stainless steel, NovoGel™, agarose, polyethylene glycol, glass, metal, plastic, or gel materials (e.g., agarose or other hydrogels), and similar materials. In some embodiments, the mold is also suitably configured to allow supplying tissue culture media to the cell paste (e.g., by dispensing tissue culture media onto the top of the mold).

Thus, in embodiments where a second shaping device is used, the partially adhered and/or cohered cell paste is transferred from the first shaping device (e.g., a capillary pipette) to the second shaping device (e.g., a mold). In further embodiments, the partially adhered and/or cohered cell paste is transferred by the first shaping device (e.g., the capillary pipette) into the grooves of a mold. In still further embodiments, following a maturation period in which the mold is incubated along with the cell paste retained therein in a controlled environment to allow the cells in the cell paste to further adhere and/or cohere to one another to form the multicellular aggregate, the cohesion of the cells will be sufficiently strong to allow the resulting multicellular aggregate to be picked up with an implement (e.g., a capillary pipette). In still further embodiments, the capillary pipette is suitably be part of a printing head of a bioprinter or similar apparatus operable to automatically place the multicellular aggregate into a three-dimensional construct.

In some embodiments, the cross-sectional shape and size of the multicellular aggregates will substantially correspond to the cross-sectional shapes and sizes of the first shaping device and optionally the second shaping device used to make the multicellular aggregates, and the skilled artisan will be able to select suitable shaping devices having suitable cross-sectional shapes, cross-sectional areas, diameters, and lengths suitable for creating multicellular aggregates having the cross-sectional shapes, cross-sectional areas, diameters, and lengths discussed above.

Placing Cohered Multicellular Aggregates onto a Support

A number of methods are suitable to place multicellular aggregates on a support to produce a desired three-dimensional structure. For example, in some embodiments, the multicellular aggregates are manually placed in contact with one another, deposited in place by extrusion from a pipette, nozzle, or needle, or positioned by an automated, computer-assisted device such as a bioprinter.

As described herein, in various embodiments, multicellular aggregates have many suitable shapes and sizes. In some embodiments, multicellular aggregates are elongate with any of several suitable cross-sectional shapes including, by way of non-limiting example, circular, oval, square, triangular, polygonal, and irregular. In further embodiments, multicellular aggregates are elongate and in the form of a cylinder. In some embodiments, elongate multicellular aggregates are of similar lengths and/or diameters. In other embodiments, elongate multicellular aggregates are of differing lengths and/or diameters. In some embodiments, multicellular aggregates are substantially spherical. In some embodiments, the engineered liver tissues include substantially spherical multicellular aggregates that are substantially similar in size. In other embodiments, the engineered liver tissues include substantially spherical multicellular aggregates that are of differing sizes. In some embodiments, engineered liver tissues of different shapes and sizes are formed by arranging multicellular aggregates of various shapes and sizes.

In some embodiments, the cohered multicellular aggregates are placed onto a support. In various embodiments, the support is any suitable biocompatible surface. In still further embodiments, suitable biocompatible surfaces include, by way of non-limiting examples, polymeric material, porous membranes, plastic, glass, metal, hydrogel, and combinations thereof. In some embodiments, the support is coated with a biocompatible substance including, by way of non-limiting examples, a hydrogel, a protein, a chemical, a peptide, antibodies, growth factors, or combinations thereof. In one embodiment, the support is coated with NovoGel™. In another embodiment, the support is coated with agarose. In one embodiment, the cohered multicellular aggregates are placed into the wells of a biocompatible multi-well container.

Once placement of the cohered multicellular aggregates is complete, in some embodiments, a tissue culture medium is poured over the top of the construct. In further embodiments, the tissue culture medium enters the spaces between the multicellular bodies to support the cells in the multicellular bodies.

Applying a Layer of a First Type of Cells and/or a Layer of a Second Type of Cells A number of methods are suitable to apply one or more layers of cells on one or more external surfaces of the cohered mammalian cell construct. For example, in some embodiments, applying a layer of cells comprises coating one or more surfaces of said cohered multicellular aggregates with a suspension, sheet, monolayer, or fused aggregates of cells. In various embodiments, 1, 2, 3, 4, or more surfaces of the cohered mammalian cell construct are coated.

In some embodiments, applying a layer of cells comprises bioprinting an additional layer of fused multicellular aggregates. In other embodiments, applying a layer of cells comprises bioprinting, spraying, or ink-jetting a solution, suspension, or liquid concentrate of cells. In further embodiments, a suitable cell suspension comprises about $1\times10^4$ to about $1\times10^6$ cells/W. In still further embodiments, a suitable cell suspension comprises about $1\times10^5$ to about $1.5\times10^5$ cells/W. In further embodiments, applying a layer of cells comprises dispensing a suspension of cells directly onto one or more surfaces of the cohered mammalian cell construct as spatially-distributed droplets. In still further embodiments, applying a layer of cells comprises dispensing a suspension of cells directly onto one or more surfaces of the cohered mammalian cell construct as a spray. Layers of cells are, in various embodiments, applied at any suitable time in the construction process. In some embodiments, one or more layers of cells are applied on one or more external surfaces of the cohered mammalian cell construct immediately after bioprinting (e.g., up to 10 min.). In other embodiments, one or more layers are applied after bioprinting (e.g., after 10 min.). In yet other embodiments, one or more layers are applied during maturation of the construct.

In some embodiments, the methods further comprise the step of culturing a layer of cells on a support. In such embodiments, applying a layer of cells, in some cases, comprises placing one or more surfaces of the engineered liver tissue construct in direct contact with an established culture of cells. In further embodiments, the construct is bioprinted directly onto a cultured layer of cells or a monolayer of cells. Any type of cultured cell layer on a biocompatible support is suitable. In some embodiments, multicellular aggregates are bioprinted onto a layer of endothelial cells. In other embodiments, multicellular aggregates are bioprinted onto a layer of non-parenchymal cells. In further embodiments, the layer of cells adheres and/or coheres with the multicellular aggregates of the bioprinted construct. In some embodiments, each layer of a multi-layered structure are bioprinted. In further embodiments, the individual layers comprise variable forms of bio-ink, including but not limited to: cohered cell aggregates, cell paste, cell paste in combination with extrusion compound(s) or other additives, cell monolayers, and cell sheets.

Co-Printed Molds Used to Fabricate Compartmentalized Tissues

In some embodiments, the methods comprise preparing one or more bio-inks comprising non-parenchymal cells; preparing one or more bio-inks comprising parenchymal cells, such as hepatocytes or hepatocyte-like cells; depositing the bio-inks onto a support; and incubating the deposited bio-inks for a duration of about 1 hour to about 30 days to form a living, three-dimensional liver tissue construct comprising at least one compartment, the compartment comprising an interior comprising parenchymal cells confined by a border comprising non-parenchymal cells.

In some embodiments, the methods comprise preparing one or more cohered multicellular aggregates comprising mammalian liver cells; placing the one or more cohered multicellular aggregates onto a support to form at least one of: at least one layer comprising a plurality of cell types, the cell types spatially arranged relative to each other to create a planar geometry; and a plurality of layers, at least one layer compositionally or architecturally distinct from at least one other layer to create a laminar geometry; and incubating said one or more multicellular aggregates for a duration of about 1 hour to about 30 days to allow them to cohere and to form a living, three-dimensional liver tissue construct.

Figure 2:
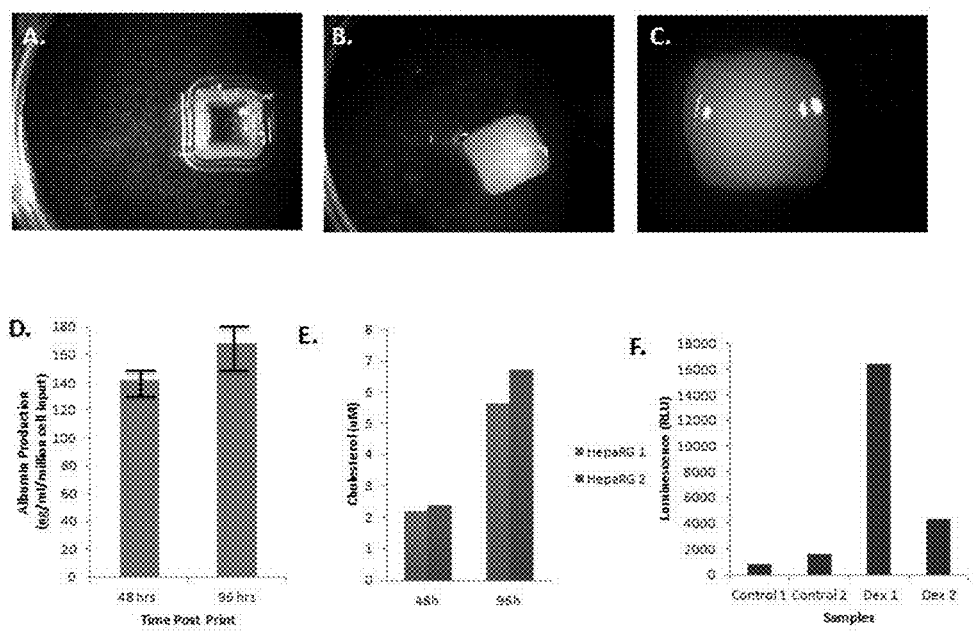
FIG. 2 is a non-limiting, exemplary demonstration of maturation and biochemical characterization of bio-printed liver constructs containing HepaRG cells. HepaRG cells were deposited into the center of the perimeter box, followed by maturation for 96 hours (A-C). Bio-printed liver constructs are metabolically active producing albumin (D) and cholesterol (E) at 96 hours. Following dexamethasone treatment, cytochrome P450 (CYP3A4) activity is more than 5-fold higher than non-treated controls (F).

Referring to FIG. 2, in a particular embodiment, liver constructs containing HepaRG cells were bio-printed, matured, and biochemically characterized. First, a perimeter box with dimensions of 4 mm×4 mm×1 mm was printed with bio-ink containing endothelial cells and hepatic stellates. Second, HepRG cells were deposited into the center of the perimeter box. This was followed by maturation for 96 hours at 37° C. Third, fusion of the bio-printed construct was observed at 20 hours post print. In this embodiment, the bio-printed liver constructs were metabolically active producing albumin and cholesterol at 96 hours.

Figure 3:
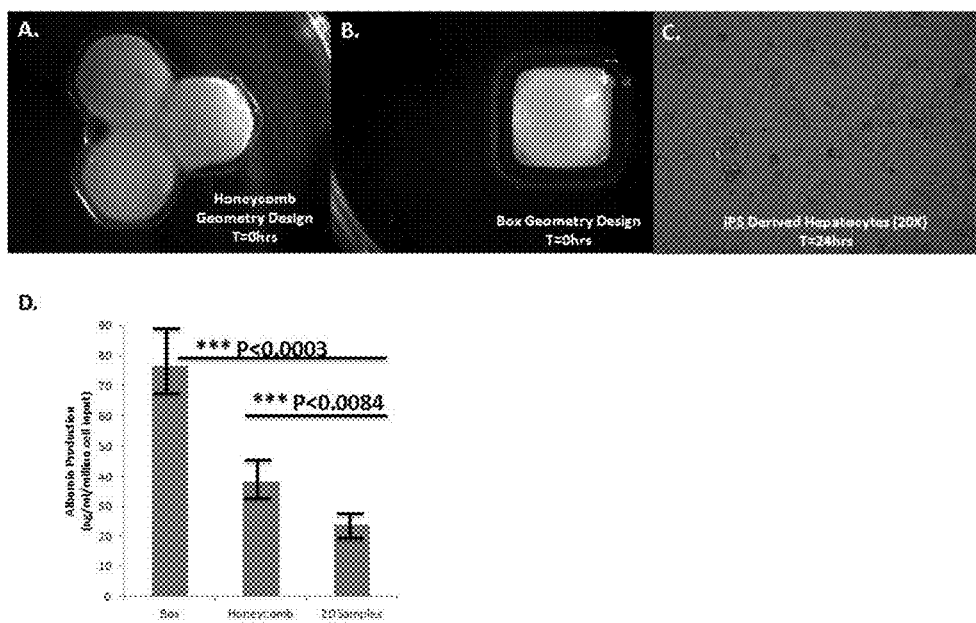
FIG. 3 is a non-limiting, example of bio-printed structures in defined geometric patterns (A, B) containing iPSC-derived hepatocytes (C) that synthesize significantly higher albumin levels (D), per million input cells, in the engineered, bioprinted construct than 2D culture controls.

Referring to FIG. 3, in a particular embodiment, liver constructs are bioprinted with borders of non-parenchymal cells and fills of parenchymal cells each made with an extrusion compound.

Figure 4:
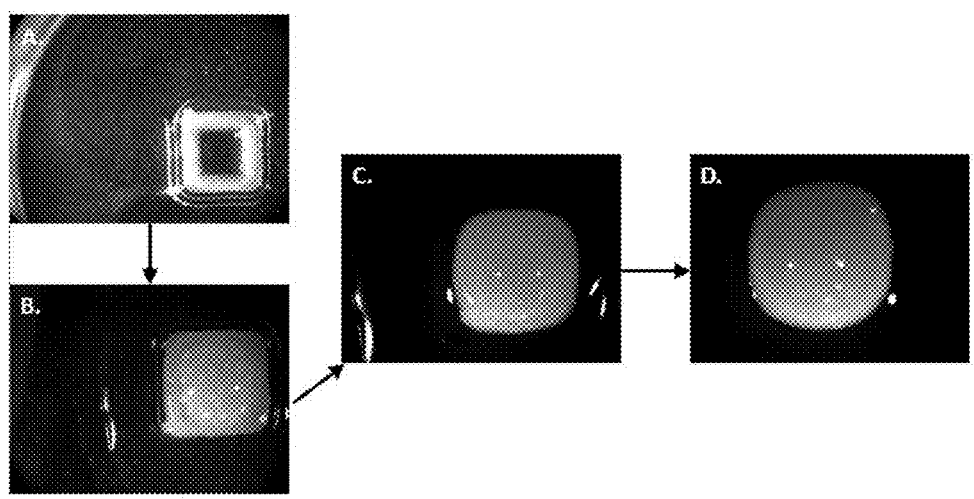
FIG. 4 is a non-limiting, exemplary demonstration of maturation of a bio-printed liver construct (A) containing discrete spheroids of non-parenchymal cells (B). The bio-printed construct remained fused and stable upon incubation for an additional 24 hours (C, D).

Referring to FIG. 4, in a particular embodiment, liver constructs are bioprinted with a border including endothelial cells and hepatic stellates, a fill including primary hepatocytes, and a third compositional component introduced as spatially-dispersed spheroids including endothelial cells and hepatic stellates within the fill.

Figure 5:
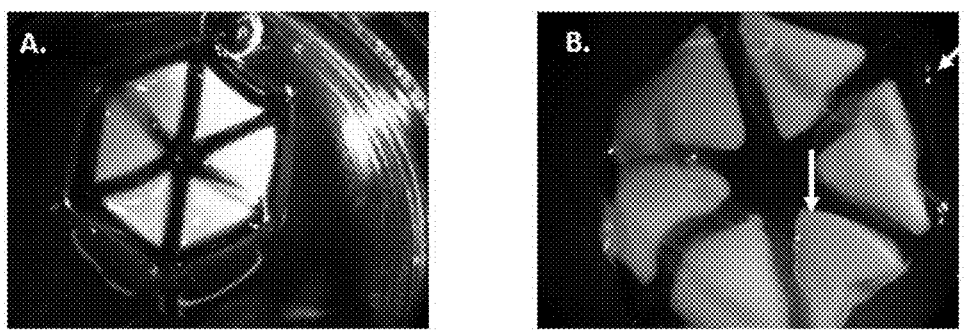
FIG. 5 is a non-limiting, exemplary demonstration of dissolution of the co-printed mold which allows spatial and temporal control over the printing process of the hepatic cells and results in the generation of user-specified compartments of a defined shape and size in the x, y, and z axes. Hepatic tissue is shown after printing (A), arrows indicate regions where the co-printed mold has dissolved 24 hours post print and areas where additional cellular inputs can be added (B).
Figure 6:
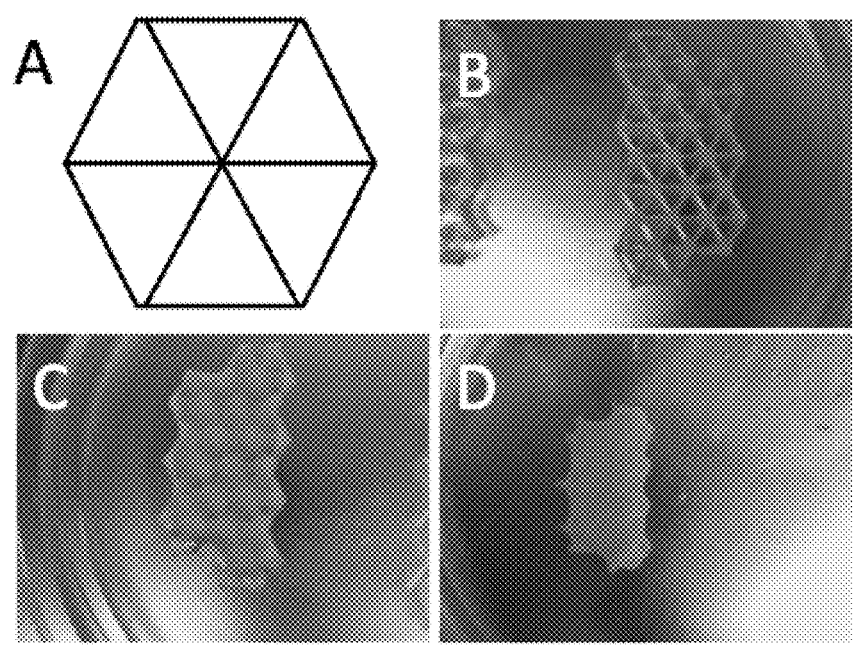
FIG. 6 is a macroscopic image depicting a non-limiting example of an engineered liver tissue, in this case, a multi-layered liver tissue bioprinted using a continuous deposition mechanism using bio-ink composed of multiple liver cell types and a water-soluble extrusion compound (e.g., PF-127). (A) shows a schematic diagram of a single functional unit highlighting the planar geometry created by patterning bio-ink and negative space; (B) tessellated, functional units bioprinted with PF-127 containing $2 \times 10^8$ cells; (C) shows the construct 20 minutes after application of media; and (D) shows the construct 16 hours after application of media to the structure and dissolution of the extrusion compound. Note retention of the planar geometry over time.

Referring to FIG. 5, in a particular embodiment, liver constructs are bioprinted with a co-mold fabricated from a material that does not contain cells (A) and dissolves in an aqueous media (e.g., PF-127) leaving only fills and establishing a negative space (B).

Referring to FIG. 6, in a particular embodiment, liver constructs are bioprinted using a continuous deposition technique using bio-ink composed of multiple liver cell types encapsulated in a water-soluble extrusion compound (e.g., PF-127) to form a tessellated functional unit pattern.

Figure 8:
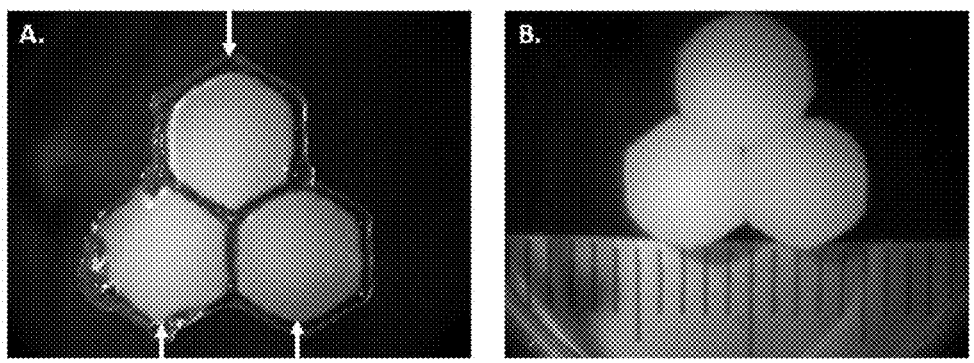
FIG. 8 is a non-limiting example of dissolution of a co-printed mold allowing fusion of distinct compartmentalized hepatic cellular regions (A; marked by arrows). Over time (B; T=24 hours) the regions fuse into a solid bio-printed tissue.

Referring to FIG. 8, in a particular embodiment, compartmentalized liver constructs are bioprinted with a co-printed mold that does not contain cells used to shape multicellular aggregates into hexagons (A). In this embodiment, the non-cellular material disappears to yield a scaffold-free tissue at the time of use (B).

Figure 10:
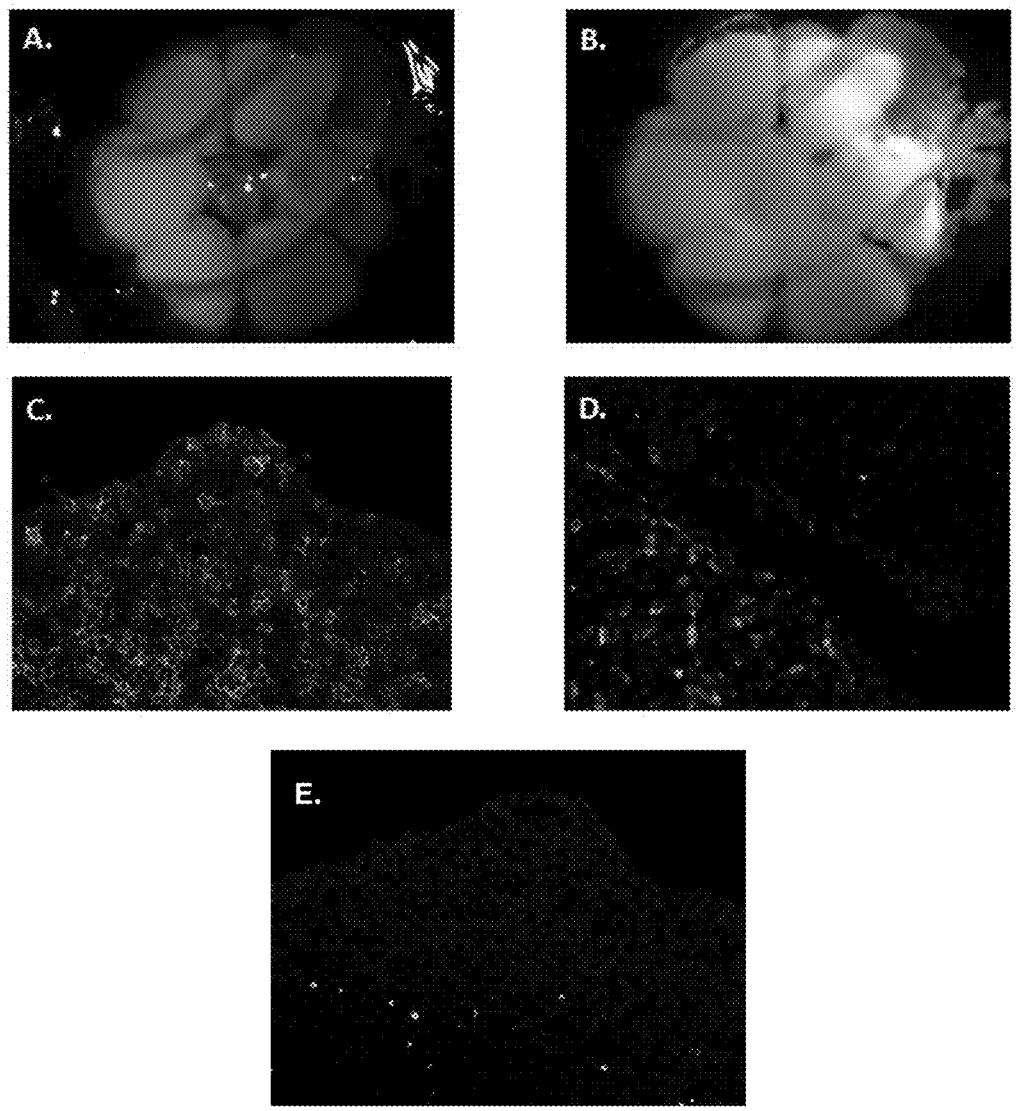
FIG. 10 is a non-limiting example of a co-printed mold (A; 4% Gelatin and 2% Alginate) bioprinted by continuous deposition with a syringe deposition module (SDM) to produce a fused 3D liver tissue construct. Addition of endothelial bio-ink in the center of the structure increases the complexity of the construct (B). E-Cadherin (C) and CD31 (D) staining demonstrate epithelial and endothelial cells present throughout the areas in which they were bioprinted at 144 hours post-print. TUNEL staining demonstrates limited cell death within the core of the engineered liver tissue following 144 h incubation (E).

Referring to FIG. 10, in a particular embodiment, compartmentalized liver constructs are bioprinted with a co-mold used as a border which is filled with HepG2 cells.

Figure 11:
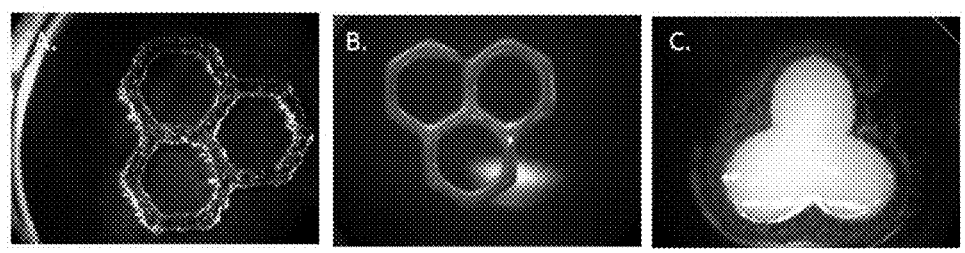
FIG. 11 is a non-limiting example of a co-printed mold (co-mold) comprised of hydrogel (4% gelatin:2% alginate) (A) or bio-ink comprised of non-parenchymal cells and a hydrogel-based extrusion compound (B). The bio-ink co-mold lines contained 150×10$^6$ cells per mL of hydrogel extrusion compound. Addition of HepG2 cells to the co-mold structure and incubation for 24 h, results in a fused, bioprinted liver structure (C). Dissolution of the extrusion compound occurs over time in aqueous media.

Referring to FIG. 11, in a particular embodiment, a co-printed mold containing cells is bio-printed as a border into which parenchymal cells are used as a fill, in this case, HepG2 cells.

Figure 12:
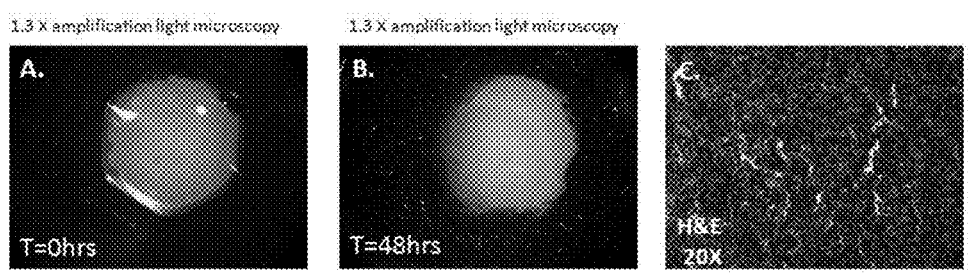
FIG. 12 is a non-limiting example of a dense, cellular liver tissue, fabricated by continuous deposition using two syringe deposition modules (SDM) on the NovoGen MMX Bioprinter. The co-mold lines containing 4% gelatin and 2% alginate were deposited by the first SDM module followed by filling of HepG2 bio-paste with a second SDM. Tissue is shown at t=0 (A), and t=48 hours (B) after printing. Also shown is H&E staining of tissue 48 hours after printing at 20× magnification (C).

Referring to FIG. 12, in a particular embodiment, compartmentalized liver constructs are bioprinted using a non-parenchymal border and a parenchymal fill (A) to achieve a high, tissue-like density (C).

Incubating Multicellular Aggregates

In some embodiments, the multicellular aggregates are incubated. In further embodiments, the incubation allows the multicellular aggregates adhere and/or cohere to form a tissue, such as a liver tissue. In some embodiments, the multicellular aggregates cohere to form a tissue in a cell culture environment (e.g., a Petri dish, cell culture flask, bioreactor, etc.). In further embodiments, the multicellular aggregates cohere to form a tissue in an environment with conditions suitable to facilitate growth of the cell types included in the multicellular aggregates. In one embodiment, the multicellular aggregates are incubated at about 37° C., in a humidified atmosphere containing about 5% $CO_2$, in the presence of cell culture medium containing factors and/or ions to foster adherence and/or coherence. In other embodiments, the multicellular aggregates are maintained in an environment that contains 0.1% to 21% $O_2$.

The incubation, in various embodiments, has any suitable duration. In further various embodiments, the incubation has a duration of about 20, 30, 40, 50, 60, 70, 80, 90, 100, 110, 120, 130, 140, 150, 160, 170, 180, or more minutes, including increments therein. In further various embodiments, the incubation has a duration of about 1, 2, 3, 4, 5, 6, 7, 8, 9, 10, 11, 12, 13, 14, 15, 16, 17, 18, 19, 20, 21, 22, 23, 24, 36, 48, or more hours, including increments therein. In further various embodiments, the incubation has a duration of about 1, 2, 3, 4, 5, 6, 7, 8, 9, 10, 11, 12, 13, 14, 15, 16, 17, 18, 19, 20, or more days, including increments therein. Several factors influence the time required for multicellular aggregates to cohere to form a tissue including, by way of non-limiting examples, cell types, cell type ratios, culture conditions, and the presence of additives such as growth factors.

Additional Steps for Increasing Viability of the Engineered Tissue

In some embodiments, the method further comprises steps for increasing the viability of the engineered tissue. In further embodiments, these steps involve providing direct contact between the tissue and a nutrient medium through a temporary or semi-permanent lattice of confinement material. In some embodiments, the tissue is constrained in a porous or gapped material. Direct access of at least some of the cells of the engineered tissue to nutrients increases the viability of the engineered tissue.

In further embodiments, the additional and optional steps for increasing the viability of the engineered tissue include: 1) optionally dispensing base layer of confinement material prior to placing cohered multicellular aggregates; 2) optionally dispensing a perimeter of confinement material; 3) bioprinting cells of the tissue within a defined geometry; and 4) dispensing elongate bodies (e.g., cylinders, ribbons, etc.) of confinement material overlaying the nascent tissue in a pattern that introduces gaps in the confinement material, such as a lattice, mesh, or grid.

Many confinement materials are suitable for use in the methods described herein. In some embodiments, hydrogels are exemplary confinement materials possessing one or more advantageous properties including: non-adherent, biocompatible, extrudable, bioprintable, non-cellular, of suitable strength, and not soluble in aqueous conditions. In some embodiments, suitable hydrogels are natural polymers. In one embodiment, the confinement material is comprised of NovoGel™. In further embodiments, suitable hydrogels include those derived from surfactant polyols such as Pluronic F-127, collagen, hyaluronate, fibrin, alginate, agarose, chitosan, gelatin, and derivatives or combinations thereof. In other embodiments, suitable hydrogels are synthetic polymers. In further embodiments, suitable hydrogels include those derived from poly(acrylic acid) and derivatives thereof, poly(ethylene oxide) and copolymers thereof, poly(vinyl alcohol), polyphosphazene, and combinations thereof. In various specific embodiments, the confinement material is selected from: hydrogel, NovoGel™, agarose, alginate, gelatin, Matrigel™, hyaluronan, poloxamer, peptide hydrogel, poly(isopropyl n-polyacrylamide), polyethylene glycol diacrylate (PEG-DA), hydroxyethyl methacrylate, polydimethylsiloxane, polyacrylamide, poly(lactic acid), silicon, silk, and combinations thereof.

In some embodiments, the gaps overlaying pattern are distributed uniformly or substantially uniformly around the surface of the tissue. In other embodiments, the gaps are distributed non-uniformly, whereby the cells of the tissue are exposed to nutrients non-uniformly. In non-uniform embodiments, the differential access to nutrients is optionally exploited to influence one or more properties of the tissue. For instance, in some cases, it is desirable to have cells on one surface of a bioprinted tissue proliferate faster than cells on another surface of the bioprinted tissue. In some embodiments, the exposure of various parts of the tissue to nutrients is changed at various times to influence the development of the tissue toward a desired endpoint.

In some embodiments, the confinement material is removed at any suitable time, including but not limited to, immediately after bioprinting (e.g., within 10 minutes), after bioprinting (e.g., after 10 minutes), before the cells are substantially cohered to each other, after the cells are substantially cohered to each other, before the cells produce an extracellular matrix, after the cells produce an extracellular matrix, just prior to use, and the like. In various embodiments, confinement material is removed by any suitable method. For example, in some embodiments, the confinement material is excised, pulled off the cells, digested, or dissolved.

In some embodiments, the methods further comprise the step of subjecting the engineered liver tissue to shear force, caused by fluid flow, agitation, or convective recirculation, on one or more sides.

EXAMPLES

The following specific examples are to be construed as merely illustrative, and not limitative of the remainder of the disclosure in any way whatsoever.

Example 1—Liver Tissue Bioprinted Using Continuous Deposition and Tessellated Functional Unit Structure Engineered liver tissue was bioprinted utilizing a NovoGen MMX Bioprinter™ (Organovo, Inc., San Diego, Calif.) using a continuous deposition mechanism. The three-dimensional structure of the liver tissue was based on a repeating functional unit, in this case, a hexagon. The bio-ink was composed of hepatic stellate cells and endothelial cells encapsulated in an extrusion compound (surfactant polyol—PF-127).

Preparation of 30% PF-127

A 30% PF-127 solution (w/w) was made using PBS. PF-127 powder was mixed with chilled PBS using a magnetic stir plate maintained at 4° C. Complete dissolution occurred in approximately 48 hours.

Cell Preparation and Bioprinting

A cell suspension comprised of 82% stellate cells (SC) and 18% human aortic endothelial cells (HAEC) and human adult dermal fibroblasts (HDFa) was separated into 15 mL tubes in order to achieve three cell concentrations: $50 \times 10^6$ cells/ml, $100 \times 10^6$ cells/ml, and $200 \times 10^6$ cells/mL following centrifugation. Each cell pellet was resuspended in 30% PF-127 and aspirated into a 3 cc reservoir using the bioprinter. With a 510 μm dispense tip, the encapsulated cells were bioprinted onto a PDMS base plate into a single hexagon (see FIG. 6A) or hexagon tessellation configuration (see FIG. 6B). Each construct received approximately 200 μL of media and was incubated for 20 minutes at room temperature to evaluate construct integrity.

Multi-Layer Bioprinting

For hexagon tessellation experiments, up to (4) sequential layers were bioprinted resulting in a taller structure with more cellular material present. Following fabrication, each construct initially received approximately 200 μL of complete media to assess construct integrity. Constructs were incubated for 20 minutes at room temperature and were then submerged in 20 mLs of complete media.

Results

Figure 7:
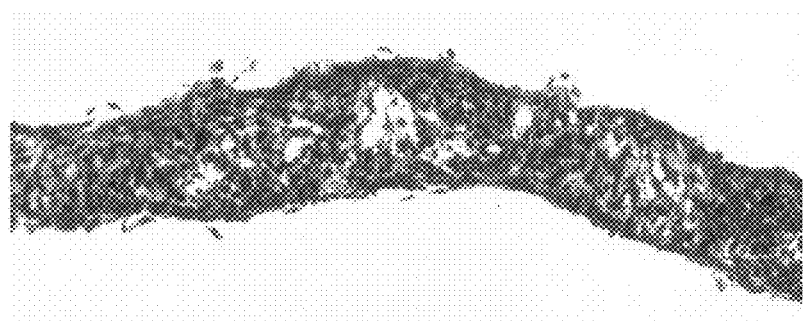
FIG. 7 is a non-limiting photomicrograph of the tessellated construct of FIG. 6, depicting an exemplary "spoke" in the tessellated construct. This photomicrograph demonstrates Hematoxylin and Eosin staining of formalin-fixed paraffin-embedded tissue sections of stellate cells, endothelial cells, and dermal fibroblasts bioprinted by continuous deposition in a multi-layer tessellated hexagonal structure and then cultured for 16 hours.

Following 18 hours of culture in growth media containing 10% fetal bovine serum (which dissolves PF127), cells contained within the bioprinted geometry were cohered to each other sufficiently to generate an intact, contiguous sheet of tissue that retained the geometrical patterning of the original design (see FIG. 6D). Shown in FIG. 7 is H&E staining of a single segment of the tessellated construct, after fixation in 10% neutral buffered formalin. Cells were found to be viable, intact, and confined to their original printed geometry.

Example 2—Forced Layering

Cell populations (homogeneous or heterogeneous) were prepared for bioprinting as either cylindrical bio-ink or as a cell suspension in Pluronic F-127 (Lutrol, BASF). Briefly, for preparation of bio-ink, cells were liberated from standard tissue culture plastic using either recombinant human trypsin (75 μg/mL, Roche) or 0.05% trypsin (Invitrogen). Following enzyme liberation, cells were washed, collected, counted and combined at desired ratios (i.e., 50:50 hepatic stellate cell (hSC):endothelial cell (EC)) and pelleted by centrifugation. Supernatant was then removed from the cell pellet and the cell mixture was aspirated into a glass microcapillary of desired diameter, typically 500 μm or 250 μm, internal diameter. This cylindrical cell preparation was then extruded into a mold, generated from non cell-adherent hydrogel material with channels for bio-ink maturation. The resulting bio-ink cylinders were then cultured in complete cell culture media for an empirically determined amount of time, typically 2 to 24 hours.

Briefly, for hydrogel cell suspension preparation, cells were liberated from standard cell culture vessel using either of the enzyme-mediated protocols described herein. Liberated cells were then washed with serum containing media, collected, counted and centrifuged to form a dense cell pellet. Supernatant was removed from the resulting cell pellet and cells were then resuspended in cold PF-127 (4° C.) at a concentration of 50 to $200 \times 10^6$ cells/mL (ranging from 10 to $300 \times 10^6$ cells/mL). This cell suspension was then aspirated into a syringe, utilizing a NovoGen MMX Bioprinter™ (Organovo, Inc., San Diego, Calif.).

Figure 13:
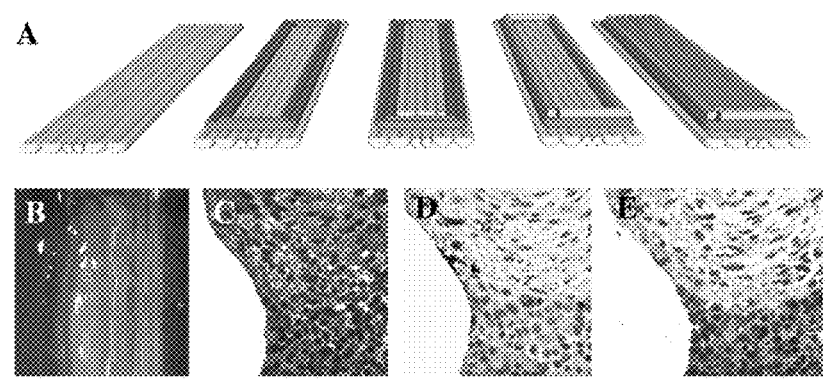
FIG. 13 is a non-limiting example of a bioprinted neotissue with laminar geometry. A NovoGel™ hydrogel base and co-printed confining box were bioprinted, followed by deposition of a first layer comprising liver epithelial cell bio-ink (HepG2 cells), onto which a second layer was bioprinted comprised of hepatic stellate cells and endothelial cells. In this example, the stellate:EC layer was bioprinted via continuous deposition of bio-ink containing a hydrogel extrusion compound (A). Gross images of construct immediately after fabrication demonstrating the two distinct layers of bio-ink (B). Hematoxylin and Eosin staining of sections of formalin-fixed paraffin-embedded constructs (C) following 48 hours of culture reveals distinct morphology of the two layers and establishment of a laminar geometry. CD31-positive cells are restricted to the upper layer of the construct where a suspension of endothelial cells and hepatic stellate cells were bioprinted (D), while IGF-2-positive HepG2 are found only in the bottom layer (E).
Figure 14:
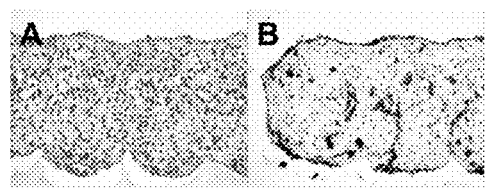
FIG. 14 is a non-limiting example of cell patterning and layering in bioprinted liver tissues. Hematoxylin and Eosin staining of paraffin-embedded tissue sections reveals a contiguous neotissue (A) formed by bioprinting polytypic cell populations containing vascular endothelial cells and hepatic stellate cells. Staining of the tissue sections with antibody directed at CD31 reveals the presence of centrally-located EC-lined microvessels and an external layer of CD31-positive EC (B).

Fabrication of tissue constructs with forced cell patterning, layering, or orientation was then accomplished using the bioprinter. Bioprinting of three-dimensional tissue constructs was performed with cylindrical bio-ink, cellular suspensions in water soluble gels, or combinations thereof. To achieve defined cell patterning or layering, combinations of relevant cell populations were included in the bio-ink or cell suspension preparation and then bioprinted in such a fashion that dissolution of the gel material supporting the cell solution, results in defined cell layering around the deposited bio-ink (see FIG. 13). Cell patterning, organization, or layering was also achieved through the utilization and incorporation of defined, discrete cell populations (e.g., hSC and EC), which resulted in predictable and repeatable organization of cells and cellular structures within the bioprinted tissues (see FIG. 14).

In some experiments, final cellular organization within the bioprinted neotissue was observed after a maturation or culture period. Constructs were maintained in a standard laboratory incubator (37° C., humidified chamber supplemented with 5% $CO_2$) and evaluated over time.

Results

Cell patterning, layering, or arrangement was achieved using bioprinting. By bioprinting with bio-ink containing heterogeneous (i.e., polytypic) cell populations, or by combining bio-ink (homogeneous or heterogeneous cell populations) with high density cell-gel or cell suspensions, distinct cell organization was observed. Maturation of these neotissue constructs in a humidified chamber (incubator) resulted in further establishment of distinct cell arrangement, organization and/or segregation in these bioprinted neotissues.

For example, bioprinting of EC:hSC-laden PF-127 on top of bioprinted bio-ink comprising HepG2 cells results in the establishment of distinct layers of the construct with distinct cell populations and discreet tissue morphology. In the case of bio-ink constructs containing hSC and EC, bioprinted constructs that were matured for more than 3 days in complete media were found to contain a distinct layer of EC at the periphery and organized microvessel networks within the core of the construct. Bioprinted constructs fabricated with bio-ink comprising a homogeneous (i.e., monotypic) population of vascular smooth muscle cell onto which a highly concentrated solution of EC was bioprinted were found to contain a distinct layer of EC at the periphery of the construct.

Example 3—Multi-Well Plates

Cell populations (homogeneous or heterogeneous) were prepared for bioprinting using a variety of bio-ink formats, including cylindrical bio-ink aggregates, suspensions of cellular aggregates, or cell suspensions/pastes, optionally containing extrusion compounds. Briefly, for preparation of cylindrical bio-ink, cells were liberated from standard tissue culture plastic using either recombinant human trypsin (75 µg/mL, Roche) or 0.05% trypsin (Invitrogen). Following enzyme liberation, cells were washed, collected, counted, and combined at desired ratios (i.e., 50:50 hepatic stellate cell (hSC):endothelial cell (EC)) and pelleted by centrifugation. Supernatant was then removed from the cell pellet and the cell mixture was aspirated into a glass microcapillary of desired diameter, typically 500 µm or 250 µm, internal diameter. This cylindrical cell preparation was then extruded into a mold, generated from non cell-adherent hydrogel material with channels for bio-ink maturation. The resulting bio-ink cylinders were then cultured in complete cell culture media for an empirically determined amount of time, typically 2 to 24 hours.

For preparation of a cell suspension or cell paste of cellular aggregates, the cell propagation and liberation protocols described herein were followed. At the time of cell pellet generation, supernatant was removed from the pellet and the pellet was transferred to a custom deposition syringe. This syringe was then mounted to the bioprinter deposition head for direct bioprinting of the cell aggregate solution or paste into multi-well plates.

Replicate tissue constructs were then bioprinted within the wells of either a multi-well tissue culture plate (e.g., 6-well or 24-well) or within a multi-well cell culture insert (i.e., Transwell, BD) and then placed into an appropriate multi-well plate. Following bioprinting, the three-dimensional constructs were matured/conditioned with relevant media for some period of time, typically 3 to 14 days. Following maturation, constructs were harvested, fixed and processed for routine histology and immunohistochemistry.
Results Bioprinted tissues were successfully fabricated within multi-well culture plates or multi-well culture inserts that were then inserted into multi-well plates. This approach allows for generation of replicate bioprinted tissues that are optionally cultured and treated to generate identical or unique culture conditions. This approach results in a significant increase in bioprinting process throughput and sample generation (see FIG. 16).

Example 4—Stimulation of Bioprinted Neotissues

Cylindrical bio-ink comprising relevant heterogeneous (i.e., polytypic) cell populations were prepared. Physiologically-relevant populations (e.g., hepatic stellate cells (hSC) and human aortic endothelial cells (EC)) of cells were combined at specific ratios to generate proper bio-ink. Cells were maintained and propagated under standard laboratory conditions and cells were cultured in media either purchased from the same vendor as the cells, or media comprising components typically found in the primary literature to be conducive to standard cell culture practices for those particular cell types. Cell processing for bio-ink preparation was as follows: briefly, cells were liberated from standard tissue culture plastic by washing with cation-free phosphate buffered saline (PBS) and then exposed to 0.1-0.05% trypsin (Invitrogen). Liberated cells were then washed in serum-containing media, collected, counted, and combined in an appropriate ratio for the stimulation assay or experiment being conducted, and pelleted by centrifugation. Supernatant was then removed and the cell pellet was aspirated into a glass microcapillary, which was then submerged in complete media for approximately 15 to 20 minutes. This cylindrical bio-ink structure was then extruded into a non cell-adherent hydrogel mold, containing linear channels and held for 2 to 18 hours. Cylindrical bio-ink containing hSC:EC was then used to fabricate bioprinted tissue constructs and maintained and/or matured in a humidified chamber. Tissue segments were fabricated with initial dimensions of 1.25 mm×8 mm×0.25 mm (W×L×H). During the post-bioprinting maturation period some constructs were exposed to the cytokine TGF-β1 to elicit a tissue-specific response (see FIG. 15).

For tissue constructs requiring a homogeneous (i.e., monotypic) cell layer, restricted to the upper surface, a secondary cell preparation was utilized containing the relevant cell type. Typically vascular endothelial cells or small airway epithelial cells (for blood vessel wall and human lung tissue models, respectively) were prepared in a highly concentrated cell suspension. Briefly, cells were liberated as described above, collected, enumerated and pelleted by centrifugation. Supernatant was removed and the cell pellet was resuspended in a small volume of complete media, yielding a highly concentrated cell pellet of 1×10$^5$ cells/µL. This cell suspension was then stored at 4° C. until time of use.

The bioprinted neotissues were then submerged in serum-containing complete cell culture media and placed in a standard humidified chamber, supplemented with 5% $CO_2$ for maturation. The bioprinted neotissues were then cultured and stimulated with a relevant cytokine(s) for a predetermined period of time, formalin-fixed, harvested, and processed for standard histology and immunohistochemistry. The bioprinted tissues were evaluated for characteristics such as, but not limited to for tissue morphology, cell organization, extracellular matrix production, cell proliferation, cell viability, and construct integrity.

Cytokine stimulation was conducted by adding cytokine directly to the culture media and incubating the bioprinted tissues with the added protein to provide direct and prolonged cell access to the proper stimulus. Dose-response experiments were conducted at doses typically ranging from 0.1 to 100 ng/mL, dependent on the ED50 of the experimental cytokine. For experiments in which cytokine stimulation was conducted over more than 48 hours, media was changed and fresh cytokine was added every 48 hours.
Results Bioprinted neotissues containing physiologically-relevant populations of cells were successfully stimulated with cytokines that had been previously demonstrated to elicit cellular responses in two-dimensional in vitro systems. The responses observed in the bioprinted three-dimensional tissue constructs were observed to be dose-dependent and unique to the cells within the bioprinted construct (see, e.g., FIG. 15).

Example 5—Bioprinting of Co-Molded Functional Liver Tissue Microstructure with Continuous Deposition Preparation of 30% PF-127

A 30% PF-127 solution (w/w) was made using PBS. PF-127 powder was mixed with chilled PBS using a magnetic stir plate maintained at 4° C. Complete dissolution occurred in approximately 48 hours.

Cell Preparation and Co-Printing of Mold and Fill

Three mL of PF-127 solution was aspirated into a 3 cc reservoir using the bioprinter and with a 510 µm dispense tip, 30% PF-127 solution was bioprinted onto a 6 well Transwell into a single hexagon shape and layered sequentially 6 times.

A cell suspension, comprised of $7.8 \times 10^7$ hepatic cells (HepG2), was centrifuged at 1000 g for 6 minutes to create the cell paste. Five µL of cell paste was extruded through a 510 µm needle to fill each of the triangular molds (see FIG. 5A). The hexagon mold was incubated at room temperature for 15 minutes. Three mL of media (DMEM supplemented with 10% FBS and 1× penicillin, streptomycin and amphotericin B) was added to the well with the Transwell supported above followed by incubation at 37° C. and 5% $CO_2$. Within 45 minutes the PF-127 mold dissolved into the media leaving the molded hepatic bio-ink intact to form a planar geometry of cells and void spaces (see FIG. 5B). To remove residual PF-127 from the media, the Transwell was transferred into a new well containing 3 mL of media and incubated for two hours. This was repeated an additional 2 times for a total media exchange of 9 mL over 6 hours.

Post 6 hours the Transwell was transferred to a new well with no media and a cell suspension of $2 \times 10^6$ cells, at a ratio of human aortic endothelial cells at 90% and 10% hepatic stellate cells, was dispensed to fill the voids created by the dissolution of PF-127 mold. The hepatic constructs were incubated for 15 minutes at room temperature. Following the 15 minute incubation, 4 mL of media containing a ratio of 85% media (DMEM supplemented with 10% FBS and 1× penicillin, streptomycin and amphotericin B, to support the hepatic and stellate cells and 15% M199 supplemented with 2% LSGS, 10% FBS, HEPES and 1× penicillin, streptomycin and amphotericin B, to support the human aortic endothelial cells). The construct was incubated at 37° C. and 5% $CO_2$ for 48 hours to form a contiguous construct, with planar geometry comprising a lobular (triangular) arrangement of hepatic parenchyma with intervening endothelial cell-comprising tissue.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein are suitably employed in practicing the invention.

What is claimed is:

1. An engineered, living, three-dimensional liver tissue construct comprising:
   (a) at least one layer comprising a plurality of cell types spatially arranged relative to each other in a planar geometry; or
   (b) a plurality of layers, at least one layer compositionally or architecturally distinct from at least one other layer in a laminar geometry, wherein the at least one other layer comprises a plurality of cell types spatially arranged relative to each other in a planar geometry;
   wherein the plurality of cell types comprises parenchymal cells in contact with non-parenchymal cells in at least one compartment that comprises an interior comprising the parenchymal cells and a border comprising the non-parenchymal cells,
   wherein the parenchymal cells comprise hepatocytes or hepatocyte-like cells and the non-parenchymal cells comprise endothelial cells, and
   wherein the construct is substantially free of pre-formed scaffold and adherent confinement material at the time of use in an assay, implantation into a subject, or use in extracorporeal support of a subject.

2. The construct of claim 1, wherein at least one component of the construct was bioprinted.

3. The construct of claim 2, further comprising an extrusion compound, the extrusion compound improving the suitability of the cells for bioprinting.

4. The construct of claim 1, wherein the perparenchymal cells are derived from one or more of the following sources: adult mammalian liver tissue; fetal mammalian liver tissue; embryonic stem cells (ESC); ESC-derived hepatocyte-like cells, induced pluripotent stem cells (IPSC); IPSC-derived hepatocyte-like cells; adult stem/progenitor cells derived from the liver; and adult stem/progenitor cells derived from a tissue other than liver.

5. The construct of claim 1, wherein the non-parenchymal cells further comprise one or more of the following cell types: vascular cells, fibroblasts, mesenchymal cells, immune cells, cancer cells, Kupffer cells, stellate cells, biliary epithelial cells, biliary epithelial-like cells, liver-derived stem/progenitor cells, and non-liver-derived stem/progenitor cells.

6. The construct of claim 1, for use in in vitro assays.

7. The construct of claim 6, for use in one or more of: drug discovery; drug testing; preclinical research; toxicity testing; absorption, distribution, metabolism, and excretion testing (ADME); drug metabolism and pharmacokinetics testing (DMPK); disease modeling; infectious disease modeling; host disease modeling; three-dimensional biology studies; and cell-based screening.

8. The construct of claim 1, for use in the augmentation of one or more liver functions in humans.

9. The construct of claim 8, for implantation in a subject at a site of injury, disease, or degeneration.

10. The construct of claim 8, for clinical use in extracorporeal devices designed to augment or restore one or more liver functions.

11. The construct of claim 1, wherein the construct is non-innervated.

12. An array of engineered living, three-dimensional liver tissue constructs, wherein each construct comprises:
   (a) at least one layer comprising a plurality of cell types spatially arranged relative to each other in a planar geometry; or
   (b) a plurality of layers, at least one layer compositionally or architecturally distinct from at least one other layer in a laminar geometry, wherein the at least one other layer comprises a plurality of cell types spatially arranged relative to each other in a planar geometry;
   wherein the plurality of cell types comprises parenchymal cells in contact with non-parenchymal cells in at least one compartment that comprises an interior comprising the parenchymal cells and a border comprising the non-parenchymal cells, wherein the parenchymal cells comprise hepatocytes or hepatocyte-like cells and the non-parenchymal cells comprise endothelial cells, and wherein each construct is substantially free of pre-formed scaffold and adherent confinement material at the time of use in an assay.

13. The array of claim 12, wherein at least one component of each construct was bioprinted.

14. The array of claim 13, wherein each construct further comprises an extrusion compound, the extrusion compound improving the suitability of the cells for bioprinting.

15. The array of claim 12, wherein the perparenchymal cells are derived from one or more of the following sources: adult mammalian liver tissue; fetal mammalian liver tissue; embryonic stem cells (ESC); ESC-derived hepatocyte-like cells, induced pluripotent stem cells (IPSC); IPSC-derived hepatocyte-like cells; adult stem/progenitor cells derived from the liver; and adult stem/progenitor cells derived from a tissue other than liver.

16. The array of claim 12, wherein each construct comprises stem/progenitor cells that were exposed to one or more differentiation signals.

17. The array of claim 16, wherein the differentiation signal comprises one or more of: biomechanical signals, soluble signals, and physical signals.

18. The array of claim 12, wherein the non-parenchymal cells further comprise one or more of the following cell types: vascular cells, fibroblasts, mesenchymal cells, immune cells, cancer cells, Kupffer cells, stellate cells, biliary epithelial cells, biliary epithelial-like cells, liver-derived stem/progenitor cells, and non-liver-derived stem/progenitor cells.

19. The array of claim 12, for use in in vitro assays.

20. The array of claim 19, for use in one or more of: drug discovery; drug testing; preclinical research; toxicity testing; absorption, distribution, metabolism, and excretion testing (ADME); drug metabolism and pharmacokinetics testing (DMPK); disease modeling; infectious disease modeling; host disease modeling; three-dimensional biology studies; and cell-based screening.

* * * * *